(12) United States Patent
Souers et al.

(10) Patent No.: US 8,202,878 B2
(45) Date of Patent: Jun. 19, 2012

(54) INHIBITORS OF DIACYLGLYCEROL O-ACYLTRANSFERASE TYPE 1 ENZYME

(75) Inventors: Andrew J. Souers, Evanston, IL (US); Ju Gao, Southbury, CT (US); Todd M. Hansen, Grayslake, IL (US); Rajesh R. Iyengar, West Newton, MA (US); Philip R. Kym, Libertyville, IL (US); Bo Liu, Waukegan, IL (US); Zhonghua Pei, Burlingame, CA (US); Vince S. Yeh, San Diego, CA (US); Gang Zhao, Northbrook, IL (US); Zhili Xin, Lexington, MA (US)

(73) Assignee: Abbott Laboratories, Abbott Park, IL (US)

( * ) Notice: Subject to any disclaimer, the term of this patent is extended or adjusted under 35 U.S.C. 154(b) by 1049 days.

(21) Appl. No.: 11/947,005

(22) Filed: Nov. 29, 2007

(65) Prior Publication Data

US 2008/0182861 A1 Jul. 31, 2008

Related U.S. Application Data

(60) Provisional application No. 60/867,695, filed on Nov. 29, 2006.

(51) Int. Cl.
C07D 487/04 (2006.01)
A61K 31/519 (2006.01)
A61P 3/04 (2006.01)
A61P 3/10 (2006.01)
C07D 231/20 (2006.01)
A61K 31/4152 (2006.01)

(52) U.S. Cl. .................. 514/259.3; 544/281; 548/366.1; 514/407; 514/406

(58) Field of Classification Search .................. 544/281; 514/259.3
See application file for complete search history.

(56) References Cited

U.S. PATENT DOCUMENTS

| 5,762,826 A | 6/1998 | Shimizu et al. |
| 6,100,077 A | 8/2000 | Sturley et al. |
| 2004/0224997 A1 | 11/2004 | Smith et al. |
| 2009/0247534 A1 | 10/2009 | Serrano-Wu et al. |

FOREIGN PATENT DOCUMENTS

| CA | 2006037 | | 6/1990 |
| EP | 0374849 | | 12/1989 |
| EP | 0718387 | A1 | 6/1996 |
| JP | 59141540 | A | 8/1984 |
| WO | 2004047755 | | 6/2004 |
| WO | 2005/072740 | A2 | 8/2005 |
| WO | 2007126957 | A2 | 11/2007 |

OTHER PUBLICATIONS

Banker, G.S. et al, "Modern Pharmaceutics, 3ed.", Marcel Dekker, New York, 1996, pp. 451 and 596.*
Wolff, Manfred E. "Burger's Medicinal Chemistry, 5ed, Part I", John Wiley & Sons, 1995, pp. 975-977.*
Cases, et al., "Cloning of DGAT2, a Second Mammalian Diacylglycerol Acyltansferase, and Related Family Members", J of Biol Chem, 276(42), 38870-38876 (2001).
Cases, et al., "Indentification of a gene encoding and acyl CoA:diacylglycerol acyltransferase, a key enzyme in triavylglycerol synthesis", Proc Nat Acad Sci USA 95, 13018-13023 (1998).
Chen, et al, Increased insulin an leptin sensitivity in mice lacking acyl CoA:diacylglycerol acyltransferase 1, J Clin Invest 109, 1049-1055 (2002).
Chen, et al. "DGAT and Triglyceride Synthesis: A New Target for Obesity Treatment?", Trens Cardiovasc Med, 10, 188-192 (2002).
Chen, et al., "Inhibition of Triglyceride Synthesis as a Treatment Strategy for Obesity Lessons From DGAT1-Deficient Mice", Arterioscler Thromb Vasc Biol, 25, 482-486 (2005).
Grundy, "Metabolic Complications of Obesity", Endocrine, 13(2), 155-165 (2000).
Lewis, et al., "Disordered Fat Storage and Mobilization in the Pathogenesis of Insulin Resistance and Type 2 Diabetes", Endocrine Reviews 23(2), 201-229 (2002).
Smith, et al., "Obesity resistance and multiple mechanisms of triglyceride synthesis in mice lacking Dgat", Nature Genetics, 25, 87-90 (2000).
Unger, "Minireview: Weapons of Lean Body Mass Destruction: The Role of Ectopic Lipids in the Methabolic Syndrome", Endocrinology, 144(12), 5159-5165 (2003).
Bellec, et al., "Deaminative electrochemical reduction of pyrazolo[1,5-a]pyrimidine-7amines", Can J Chem, 59, 2826-2832, (1981), especially p. 2827, Table 1, Compound 1a.
Supplementary European Search Report from European Application Publication No. EP2117526, dated Jun. 7, 2011.

* cited by examiner

*Primary Examiner* — Susanna Moore
(74) *Attorney, Agent, or Firm* — Lisa V. Mueller; Michael Best & Friedrich LLP

(57) ABSTRACT

The present invention relates to a compound of formula (I), or a pharmaceutically acceptable salt thereof,

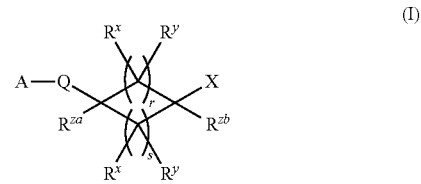

a pharmaceutical composition of formula (I), and related methods for treating or preventing metabolic diseases or conditions.

8 Claims, No Drawings

INHIBITORS OF DIACYLGLYCEROL O-ACYLTRANSFERASE TYPE 1 ENZYME

CROSS-REFERENCE SECTION TO RELATED APPLICATIONS

This application claims priority to U.S. application Ser. No. 60/867,695, filed Nov. 29, 2006, and is incorporated herein by reference in its entirety.

FIELD OF INVENTION

The present invention relates to compounds that are inhibitors of the diacylglycerol O-acyltransferase type 1 (DGAT-1) enzyme. Methods of using such compounds to inhibit the activity of diacylglycerol O-acyltransferase type 1 and pharmaceutical compositions including such compounds are also encompassed.

BACKGROUND OF THE INVENTION

Triacylglycerides represent the major form of energy storage in eukaryotes, and disorders or imbalance in triacylglyceride metabolism are implicated in the pathogenesis and increased risk for obesity, insulin resistance, type II diabetes, nonalcoholic fatty liver disease and coronary heart disease (Lewis, et al., Endocrine Reviews 23:201, 2002). Storage of excess triacylglycerides in lean tissues, such as liver, muscle, and other peripheral tissues, leads to lipid-induced dysfunction in those tissues; thus, reducing fat accumulation in nonadipose sites appears to be of benefit in the treatment of lipotoxicity (Unger, R. H. Endocrinology, 144: 5159-5165, 2003). Accumulation of excess triacylglycerides in white adipose tissue (WAT) leads to obesity, a condition that is associated with decreased life span, type II diabetes, coronary artery disease, hypertension, stroke, and the development of some cancers (Grundy, S. M. Endocrine 13(2): 155-165, 2000). Obesity is a chronic disease that is highly prevalent in modern society and current pharmacological treatment options are limited, creating a need to develop pharmaceutical agents for the treatment of obesity that are safe and effective.

Diacylglycerol O-acyltransferases (DGATs) are membrane-bound enzymes that catalyze the terminal step of triacylglycerides biosynthesis. Two enzymes that display DGAT activity have been characterized: DGAT-1 (diacylglycerol O-acyltransferase type 1) (U.S. Pat. No. 6,100,077; Cases, et al., Proc. Nat. Acad. Sci. 95:13018-13023, 1998) and DGAT-2 (diacylglycerol O-acyltransferase type 2) (Cases, et al., J. Biol. Chem. 276:38870-38876, 2001). DGAT-1 and DGAT-2 share only 12% sequence identity. Significantly, DGAT-1 null mice are resistant to diet-induced obesity and have increased sensitivity to insulin and leptin (Smith, et al., Nature Genetics 25:87-90, 2000: Chen and Farese, Trends Cardiovasc Med. 10:188, 2000: Chen et al. J. Clin. Invest. 109:10049, 2002). DGAT-1 deficient mice are protected against hepatic steatosis, demonstrate increased energy expenditure, and decreased levels of tissue triacylglycerides. In addition to improved triacylglycerides metabolism, DGAT-1 deficient mice also have improved glucose metabolism, with lower glucose and insulin levels following a glucose load, in comparison to wild-type mice. Partial DGAT-1 deficiency in heterozygous DGAT-1+/−animals is sufficient to deliver an intermediate phenotype on body weight, adiposity, and insulin and glucose metabolism when compared to wild type and homozygous littermates (Chen and Farese, Arterioscler. Thromb. Vase. Biol. 25:482-486, 2005), and small molecule DGAT-1 inhibitors have been reported to induce weight loss in diet-induced obese (DIO) mice (US 2004/0224997). The phenotypes of DGAT-1 deficient mice, and the pharmacological activity reported with DGAT-1 inhibitors suggests that the discovery of small molecules that effectively block the conversion of diacylglycerol to triacylglycerides by inhibiting the DGAT-1 enzyme can have utility in the treatment of obesity and other diseases associated with triacylglycerides imbalance.

SUMMARY OF THE INVENTION

One aspect of the invention is directed towards compounds of formula (I), or a pharmaceutically acceptable salt, prodrug, salt of a prodrug, or a combination thereof.

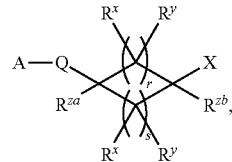

(I)

wherein:

Q is phenyl or a monocyclic heteroaryl, optionally substituted with 1, 2 or 3 substituents as represented by T, wherein each T is independently alkyl, alkenyl, alkynyl, halogen, —CN, —NO$_2$, —OR$^1$, —OC(O)(R$^2$), —N(R$^w$)(R$^1$), —N(R$^w$)—C(O)(R$^1$), —N(R$^w$—C(O)O(R$^1$), —N(R$^w$)—C(O)N(R$^1$)$_2$, —N(R$^w$)—S(O)$_2$(R$^2$), —C(O)O(R$^1$), —C(O)N(R$^w$)(R$^1$), —C(O)R$^1$, —SR$^1$, —S(O)R$^2$, —S(O)$_2$R$^2$, —S(O)$_2$N(R$^w$)(R$^1$), —(CR$^g$R$^h$)$_t$—CN, —(CR$^g$R$^h$)$_t$—NO$_2$, —(CR$^g$R$^h$)$_t$—OR$^1$, —(CR$^g$R$^h$)$_t$—OC(O)(R$^2$), —(CR$^g$R$^h$)$_t$—N(R$^w$)(R$^1$), —(CR$^g$R$^h$)$_t$—N(R$^w$)—C(O)(R$^1$), —(CR$^g$R$^h$)$_t$—N(R$^w$)—C(O)O(R$^1$), —(CR$^g$R$^h$)$_t$—N(R$^w$)—C(O)N(R$^1$)$_2$, —(CR$^g$R$^h$)$_t$—N(R$^w$)—S(O)$_2$(R$^2$), —(CR$^g$R$^h$)$_t$—C(O)O(R$^1$), —(CR$^g$R$^h$)$_t$—C(O)N(R$^w$)(R$^1$), —(CR$^g$R$^h$)$_t$—C(O)R$^1$, —(CR$^g$R$^h$)$_t$—SR$^1$, —(CR$^g$R$^h$)$_t$—S(O)R$^2$, —(CR$^g$R$^h$)$_t$—S(O)$_2$R$^2$, —(CR$^g$R$^h$)$_t$—S(O)$_2$N(R$^w$)(R$^1$) or haloalkyl; alternatively, two of the adjacent T substituents, together with the carbon atoms to which they are attached, form a monocyclic ring selected from the group consisting of phenyl, heterocycle and heteroaryl, wherein each ring is optionally further substituted with 1, 2 or 3 substituents selected form the group consisting of oxo, alkyl, alkenyl, alkynyl, halogen, —CN, —NO$_2$, —OR$^1$, —OC(O)(R$^2$), —N(R$^w$)(R$^1$), —N(R$^w$)C(O)(R$^1$), —N(R$^w$)—C(O)O(R$^1$), —N(R$^w$)—C(O)N(R$^1$)$_2$, —N(R$^w$)—S(O)$_2$(R$^2$), —C(O)O(R$^1$), —C(O)N(R$^w$)(R$^1$), —C(O)R$^1$, —SR$^1$, —S(O)R$^2$, —S(O)$_2$R$^2$, —S(O)$_2$N(R$^w$)(R$^1$)—, —(CR$^g$R$^h$)$_t$—CN, —(CR$^g$R$^h$)$_t$—NO$_2$, —(CR$^g$R$^h$)$_t$—OR$^1$, —(CR$^g$R$^h$)$_t$—OC(O)(R$^2$), —(CR$^g$R$^h$)$_t$—N(R$^w$)(R$^1$), —(CR$^g$R$^h$)$_t$—N(R$^w$)—C(O)(R$^1$), —(CR$^g$R$^h$)$_t$—N(R$^w$)—C(O)O(R$^1$), —(CR$^g$R$^h$)$_t$—N(R$^w$)—C(O)N(R$^1$)$_2$, —(CR$^g$R$^h$)$_t$—N(R$^w$)—S(O)$_2$(R$^2$), —(CR$^g$R$^h$)$_t$—C(O)O(R$^1$), —(CR$^g$R$^h$)$_t$—C(O)N(R$^w$)(R$^1$), —(CR$^g$R$^h$)$_t$—C(O)R$^1$, —(CR$^g$R$^h$)$_t$—SR$^1$, —(CR$^g$R$^h$)$_t$—S(O)R$^2$, —(CR$^g$R$^h$)$_t$—S(O)$_2$R$^2$, —(CR$^g$R$^h$)$_t$—S(O)$_2$N(R$^w$)(R$^1$), and haloalkyl;

A is phenyl, or a 4-, 5-, 6- or 7-membered monocyclic ring selected from the group consisting of heteroaryl and heterocycle, wherein each A is independently further unsubstituted or substituted with 1, 2, 3, 4 or 5 substitutents represented by R$^a$, and R$^a$ is selected from the group consisting of oxo, —N(R$^w$)C(O)H, alkyl, alkenyl, alkynyl, halogen, —NO$_2$, —CN, haloalkyl, G$^1$, —(CR$^e$R$^f$)$_q$-G$^1$, —Y$^1$—Y$^3$, —Y$^1$—

$(CR^eR^f)_q$—Y³, —Y¹—$(CR^eR^f)_q$—Y²—Y³, and —Y¹—$(CR^eR^f)_q$—Y²—$(CR^eR^f)_q$—Y³; or A is formula (a)

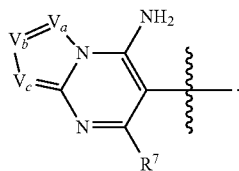

(a)

wherein:
$V_a$ is $C(R^4)$, $V_b$ is N or $C(R^5)$ and $V_c$ is N, or
$V_a$ is N, $V_b$ is $C(R^5)$, and $V_c$ is N or $C(R^6)$;

R⁴ is hydrogen, halogen, alkyl, haloalkyl, —CN, —OR^b, —SR^b, —S(O)R^c, —S(O)₂R^c, —N(R^b)(R^d), or heterocycle, R⁵ is hydrogen, alkyl, halogen, haloalkyl, —CN, —OR^b, —SR^b, —S(O)R^c, —S(O)₂R^c, aryl, heteroaryl, cycloalkyl, cycloalkenyl, or heterocycle;

R⁶ is hydrogen, alkyl, halogen, haloalkyl, aryl, heteroaryl, cycloalkyl, cycloalkenyl, or heterocycle; or R⁴ and R⁵, together with the carbon atoms to which they are attached, form a phenyl ring which is further unsubstituted or substituted with 1, 2, 3 or 4 substituents selected from the group consisting of alkyl, halogen, —CN, —OR^b, —SR^b, and haloalkyl;

R⁷ is hydrogen, alkyl, halogen, —CN, or haloalkyl;

G¹ is cycloalkyl, cycloalkenyl, heterocycle, heteroaryl, or aryl;

Y¹ and Y², at each occurrence, are each independently O, S, S(O), S(O)₂, N(R^w), —C(O), —OC(O)—, —N(R^w)C(O)—, —N(R^w)S(O)₂—, —N(R^w)C(O)N(R^w)—, —OC(O)N(R^w)—, —N(R^w)C(O)O—, —C(O)O—, —C(O)N(R^w)—, or —S(O)₂N(R^w)—; wherein the right side of the —OC(O)—, —N(R^w)C(O)—, —N(R^w)S(O)₂—, —N(R^w)C(O)N(R^w)—, —OC(O)N(R^w)—, —N(R^w)C(O)O—, —C(O)O—, —C(O)N(R^w)—, and —S(O)₂N(R^w)— moieties are connected to —$(CR^eR^f)_q$— or Y³;

Y³ at each occurrence is independently hydrogen, alkyl, haloalkyl, cycloalkyl, cycloalkenyl, heterocycle, heteroaryl, or aryl;

r and s are independently 1 or 2;

X is X¹, —$(CR^kR^m)_u$—X¹, —$(CR^kR^m)_u$—C(O)—X², or —C(O)—X²,

X¹ at each occurrence is independently heterocycle, or heteroaryl;

X² at each occurrence is independently heteroaryl, heterocycle, —OR¹¹, —N(R^w)(R³), —N(R^w)—$(CR''R^q)_w$—C(O)OR¹¹, —N(R^w)—$(CR''R^q)_w$—OR¹¹, or —N(R^w)—$(CR''R^q)_w$—S(O)₂R¹²;

R¹¹, at each occurrence, is independently hydrogen, alkyl, haloalkyl, arylalkyl, or heteroarylalkyl;

R¹², at each occurrence, is alkyl, haloalkyl, arylalkyl, or heteroarylalkyl, wherein the cycloalkenyl, cycloalkyl, heterocycle, heteroaryl, aryl, the aryl moiety of the arylalkyl, and the heteroaryl moiety of the heteroarylalkyl as represented by G¹, Y³, X¹, X², R⁴, R⁵, R⁶, R¹¹ and R¹², are each optionally further substituted with 1, 2, 3, 4 or 5 substituents selected from the group consisting of alkyl, alkenyl, alkynyl, halogen, oxo, ethylenedioxy, methylenedioxy, —CN, —NO₂, —OR¹, —OC(O)(R²), —N(R^w)(R¹), —N(R^w)—C(O)(R¹), —N(R^w)—C(O)O(R¹), —N(R^w)—S(O)₂(R²), —C(O)O(R¹), —C(O)N(R^w)(R¹), —C(O)R¹, —SR¹, —S(O)R², —S(O)₂R², —S(O)₂N(R^w)(R¹), haloalkyl, —$(CR^gR^h)_v$—CN, —$(CR^gR^h)_v$—NO₂, —$(CR^gR^h)_v$—OR¹, —$(CR^gR^h)_v$—OC(O)(R²), —$(CR^gR^h)_v$—N(R^w)(R¹), —$(CR^gR^h)_v$—N(R^w)C(O)(R¹), —$(CR^gR^h)_v$—N(R^w)—C(O)O(R¹), —$(CR^gR^h)_v$—N(R^w)—S(O)₂(R²), —$(CR^gR^h)_v$—C(O)O(R¹), —$(CR^gR^h)_v$—C(O)N(R^w)(R¹), —$(CR^gR^h)_v$—C(O)R¹, —$(CR^gR^h)_v$—SR¹, —$(CR^gR^h)_v$—S(O)R², —$(CR^gR^h)_v$—S(O)₂R²—$(CR^gR^h)_v$—S(O)₂N(R^w)(R¹), and haloalkyl;

q, t, u, v and w, at each occurrence, are each independently 1, 2, 3, 4, 5, or 6;

R³ is hydrogen, alkyl, haloalkyl, —OH, —S(O)₂R¹, —C(O)OR¹, heterocycle or heteroaryl, wherein the heteroaryl is connected to the nitrogen atom through the ring carbon atom, and the heterocycle and heteroaryl are optionally further substituted with 1 or 2 substituents selected from the group consisting of alkyl, halogen, haloalkyl, —C(O)OR¹, —OR¹ and —N(R^w)(R¹);

R^b, R^d, R^x, R^y, R^{za}, R^{zb}, R^w, R^e, R^g, R^h, R^k, R^m, R''R^q and R¹, at each occurrence, are independently hydrogen, alkyl, or haloalkyl, R^e and R², at each occurrence, are independently alkyl or haloalkyl; and R^f, at each occurrence, is independently hydrogen, alkyl, halogen, haloalkyl, —OH, —O(alkyl), or —O(haloalkyl).

Another aspect of the invention provides methods of treating various diseases or conditions in a mammal, such as a human, wherein the methods include administering to the mammal in need thereof a compound of the invention as set forth herein, or a pharmaceutically acceptable salt thereof, or a pharmaceutical composition including a compound of the invention described herein or salt of the compound, and a pharmaceutically acceptable carrier. In another aspect, the invention provides methods of preventing or treating a disease or condition related to elevated lipid levels, such as plasma lipid levels or elevated triglycerides levels, in a mammal afflicted with such elevated levels. The invention also relates to novel compounds having therapeutic ability to reduce lipid levels in a mammal such as triglycerides levels. In another aspect, the invention provides pharmaceutical compositions including the compound of the invention as set forth herein, a pharmaceutically acceptable salt, or a prodrug thereof, and a pharmaceutically acceptable carrier. Further, the present invention provides various methods of treating various conditions in a patient including the step of administering to the patient a pharmaceutical composition including a compound of the invention, a pharmaceutically acceptable salt, or a prodrug thereof, and a pharmaceutically acceptable carrier.

DETAILED DESCRIPTION OF THE INVENTION

For a variable that occurs more than one time in any substituent, its definition on each occurrence is independent of its definition at every other occurrence. Combinations of substituents are permissible only it such combinations result in stable compounds. Stable compounds are compounds, which can be isolated in a useful degree of purity from a reaction mixture.

As used in the specification and the appended claims, unless specified to the contrary, the following terms have the meaning indicated below.

The term "alkenyl" as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkyl" as used herein, means a straight or branched chain hydrocarbon containing from 1 to 10 carbon atoms, preferably having 1 to 6 carbon atoms. The term "lower alkyl" or "$C_{1-6}$ alkyl" means a straight or branched chain hydrocarbon containing 1 to 6 carbon atoms. The term "$C_{1-3}$ alkyl" means a straight or branched chain hydrocarbon containing 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylene" denotes a divalent group derived from a straight or branched chain hydrocarbon of from 1 to 10 carbon atoms. Representative examples of alkylene include, but are not limited to, —$CH_2$—, —$CH_2CH_2$—, —$CH_2CH_2CH_2$—, —$CH_2CH_2CH_2CH_2$—, and —$CH_2CH(CH_3)CH_2$—.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl" as used herein, means phenyl or a bicyclic aryl. The bicyclic aryl is naphthyl, or a phenyl fused to a monocyclic cycloalkyl, or a phenyl fused to a monocyclic cycloalkenyl. The phenyl and the bicyclic aryl groups of the present invention are unsubstituted or substituted. The bicyclic aryl is attached to the parent molecular moiety through any carbon atom contained within the bicyclic aryl. Representative examples of the aryl groups include, but are not limited to, dihydroindenyl, indenyl, naphthyl, dihydronaphthalenyl, and 5,6,7,8-tetrahydronaphthalenyl.

The term "arylalkyl" as used herein, means an aryl group as defined herein, attached to the parent moiety through an alkyl group, as defined herein.

The term "cycloalkyl" or "cycloalkane" as used herein, means a monocyclic or bicyclic cycloalkyl. The monocyclic cycloalkyl has three to eight carbon atoms, zero heteroatom and zero double bond. The monocyclic cycloalkyl can be attached to the parent molecular moiety through any substitutable atom contained within the monocyclic cycloalkyl. Examples of monocyclic ring systems include cyclopropyl, cyclobutyl, cyclopentyl, cyclohexyl, cycloheptyl, and cyclooctyl. The bicyclic cycloalkyl is a monocyclic cycloalkyl fused to a monocyclic cycloalkyl, or a monocyclic cycloalkyl in which two non-adjacent carbon atoms of the monocyclic cycloalkyl are linked by an alkylene bridge of one, two, three or four carbon atoms. The bicyclic cycloalkyl can be attached to the parent molecular moiety through any substitutable atom contained within the bicyclic cycloalkyl ring and can contain an additional alkylene bridge of one, two, three or four carbon atoms linking two non adjacent carbon atoms (of the same or different rings). Representative examples of bicyclic cycloalkyl include, but not limited to, adamantyl. The monocyclic and bicyclic cycloalkyl groups of the present invention can be unsubstituted or substituted.

The term "cycloalkenyl" or "cycloalkene" as used herein, means a monocyclic or a bicyclic hydrocarbon ring system. The monocyclic cycloalkenyl has four-, five-, six-, seven- or eight carbon atoms and zero heteroatom. The four-membered ring systems have one double bond, the five- or six-membered ring systems have one or two double bonds, and the seven- or eight-membered ring systems have one, two or three double bonds. The monocyclic cycloalkenyl can be attached to the parent molecular moiety through any substitutable atom contained within the monocyclic cycloalkenyl. Representative examples of monocyclic cycloalkenyl groups include, but are not limited to, cyclobutenyl, cyclopentenyl, cyclohexenyl, cycloheptenyl and cyclooctenyl. The bicyclic cycloalkenyl is a monocyclic cycloalkenyl fused to a monocyclic cycloalkyl group, or a monocyclic cycloalkenyl fused to a monocyclic cycloalkenyl group, or a monocyclic cycloalkenyl in which two non-adjacent carbon atoms of the monocyclic cycloalkenyl are linked by an alkylene bridge of one, two, three or four carbon atoms. The bicyclic cycloalkenyl can be attached to the parent molecular moiety through any substitutable atom contained within the bicyclic cycloalkenyl. Representative examples of the bicyclic cycloalkenyl groups include, but are not limited to, 4,5,6,7-tetrahydro-3aH-indene, octahydronaphthalenyl and 1,6-dihydro-pentalene. The monocyclic and bicyclic cycloalkenyl groups of the present invention can be unsubstituted or substituted.

The term "halo" and "halogen" as used herein, means —Cl, —Br, —I or —F.

The term "haloalkyl" as used herein, means an alkyl group, as defined herein, in which one, two, three, tour, live or six hydrogen atoms are replaced by halogen. Representative examples of haloalkyl include, but are not limited to, chloromethyl, difluoromethyl, 2-fluoroethyl, trifluoromethyl, pentafluoroethyl, and 2-chloro-3-fluoropentyl.

The term "heterocycle" or "heterocyclic" as used herein, means a monocyclic heterocycle, or a bicyclic heterocycle. The monocyclic heterocycle is a three-, four-, five-, six-, or seven-membered ring containing at least one heteroatom independently selected from the group consisting of O, N, and S. The three- or four-membered ring contains zero or one double bond, and one heteroatom selected from the group consisting of O, N and S. The five-membered ring contains zero or one double bond and one, two or three heteroatoms selected from the group consisting of O, N and S. The six-membered ring contains zero, one or two double bonds and one, two or three heteroatoms selected from the group consisting of O, N and S. The seven-membered ring contains zero, one, two, or three double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 2,5-dihydro-1H-pyrazolyl (including 2,5-dihydro-1H-pyrazol-3-yl), 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl (including tetrahydrofuran-2-yl), tetrahydrothienyl, tetrahydropyranyl (including tetrahydro-2H-pyran-2-yl, tetrahydro-2H-pyran-4-yl), thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, a monocyclic heterocycle fused to a monocyclic heterocycle. The bicyclic heterocycle is connected to the parent molecular moiety through any carbon atom or any nitrogen atom contained within the bicyclic heterocycle. The monocyclic and bicyclic heterocycle of the present invention can be unsubstituted or substituted. Representative examples of bicyclic heterocycle include, but are not limited to, 2,3-dihydro-1,4-benzodioxinyl (including 2,3-dihydro-1,4-benzodioxin-2-yl), 1,3-benzodithiolyl, benzopyranyl, benzothiopyranyl, 2H-chromen-2-yl, 2H-chromen-3-yl, 2H-chromen-4-yl, 2,3-dihydrobenzofuranyl, 2,3-dihydrobenzothienyl, 2,3-dihydro-1H-indolyl, 2,3-dihydroisoindol-2-yl, 2,3-dihydroisoindol-3-yl, 1,3-dioxo-1H-isoindolyl, and 1,2,3,4-tetrahydroquinolinyl.

The term "heteroaryl" as used herein, means a monocyclic heteroaryl, or a bicyclic heteroaryl. The monocyclic heteroaryl is a five- or six-membered ring. The five-membered ring includes two double bonds, and one, two, three or four nitrogen atoms and optionally one oxygen or sulfur atom. The six-membered ring includes three double bonds and one, two, three or four nitrogen atoms. Representative examples of monocyclic heteroaryl include, but are not limited to, furanyl (including furan-2-yl), imidazolyl, isoxazolyl (including isoxazol-3-yl), isothiazolyl, oxadiazolyl, oxazolyl (including 1,3-oxazol-4-yl), pyridinyl (including pyridin-2-yl, pyridin-3-yl, pyridin-4-yl), pyridazinyl, pyrimidinyl, pyrazinyl (including pyrazin-2-yl), pyrazolyl (including 1H-pyrazol-3-yl, 1H-pyrazol-5-yl), pyrrolyl, tetrazolyl (including 2H-tetrazol-5-yl), thiadiazolyl, thiazolyl (including 1,3-thiazol-4-yl), (including 1,3-thiazol-4-yl), thienyl (including thien-2-yl), triazolyl (including 1,2,4-triazol-5-yl), and triazinyl. The bicyclic heteroaryl includes a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. The monocyclic and bicyclic heteroaryl groups of the present invention can be substituted or unsubstituted. The monocyclic and the bicyclic heteroaryl are connected to the parent molecular moiety through any carbon atom or any nitrogen atom contained within the group. Representative examples of bicyclic heteroaryl groups include, but not limited to, benzofuranyl, benzothienyl, benzoxazolyl, benzimidazolyl, benzoxadiazolyl, 6,7-dihydro-1,3-benzothiazolyl, imidazo[1,2-a]pyridinyl, indazolyl, indolyl, isoindolyl, isoquinolinyl, naphthyridinyl, pyridoimidazolyl, quinolinyl, thiazolo[5,4-b]pyridin-2-yl, thiazolo[5,4-d]pyrimidin-2-yl, and 5,6,7,8-tetrahydroquinolin-5-yl.

The term "heteroarylalkyl" as used herein, means a heteroaryl group as defined herein, attached to the parent moiety through an alkyl group, as defined herein.

The term "heteroatom" as used herein, means a nitrogen, oxygen or sulfur atom.

Preferable values of variable groups in compounds of formula (I) are as follows. Such values can be used where appropriate with any of the other values, definitions, claims or embodiments defined hereinbefore or hereinafter.

In one embodiment, Q is phenyl, unsubstituted or further substituted as described in the summary section. In another embodiment, Q is a monocyclic heteroaryl, optionally further substituted as described in the summary section. An example of Q is pyridinyl. When Q is phenyl or a 6-membered heteroaryl, it is preferred that A is located on the 4-position of the ring Q, relative to the point of attachment between Q and the cycloalkyl ring of formula (I).

The optional substituents of Q as represented by T have values as described in the Summary section. For example, T is halogen.

In a further embodiment, A is phenyl, unsubstituted or further substituted as described in the summary section. Alternatively, A is a 4-, 5-, 6- or 7-membered monocyclic ring selected from the group consisting of heteroaryl and heterocycle, each of which is independently unsubstituted or further substituted as described in the summary section.

In another embodiment, A is a 5- or 6-membered monocyclic heteroaryl, unsubstituted or further substituted as stated in the summary. Examples of A as a heteroaryl ring include, but are not limited to, furanyl, imidazolyl, isoxazolyl, isothiazolyl, oxadiazolyl, oxazolyl, pyridinyl, pyridazinyl, pyrimidinyl, pyrazinyl, pyrazolyl, pyrroyl, tetrazolyl, thiadiazolyl, thiazolyl, thienyl, triazolyl, and triazinyl. Preferably, A is pyrazolyl, triazolyl, thiazolyl, oxazolyl, or pyrazinyl. More preferably, A is pyrazolyl (e.g. 1H-pyrazol-3-yl, 1H-pyrazol-5-yl) or triazolyl (e.g. 1,2,4-triazol-5-y). Each example of A is independently further unsubstituted or substituted as described in the summary.

In yet another embodiment, A is an optionally substituted monocyclic heterocycle ring.

For example, A is optionally substituted 2,5-dihydro-1H-pyrazol-3-yl.

A can be unsubstituted or further substituted with 1, 2, 3, 4 or 5 substituents as described in the summary section. Preferably, A is optionally substituted with 1, 2 or 3 substituents. Examples of substituents of A include, but are not limited to, oxo. $N(R^w)C(O)H$, halogen, alkyl (for example $C_{1-6}$ alkyl such as methyl, ethyl, isopropyl, n-propyl, n-butyl and the like), haloalkyl (for example $C_{1-6}$ haloalkyl such as difluoromethyl or trifluoromethyl), —$(CR^eR^f)_q$-$G^1$, —$Y^1$—$Y^3$, —$Y^1$—$(CR^eR^f)_q$—$Y^3$, and —$Y^1$—$(CR^eR^f)_q$—$Y^2$—$Y^3$.

In one embodiment, where A is substituted with —$(CR^eR^f)_q$-$G^1$, q is 1 or 2, $R^e$ and $R^f$ are hydrogen or alkyl such as $C_{1-6}$ alkyl (preferably methyl), and $G^1$ is as described in the Summary. Preferably, $R^e$ and $R^f$ are hydrogen, and $G^1$ is cycloalkyl (for example, cyclopropyl, cyclobutyl, cyclopentyl, cyclohexyl), aryl (for example, phenyl) or heteroaryl such as, but not limited to, furanyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl, preferably furanyl, wherein each $G^1$ is independently unsubstituted or further substituted as described in the summary section. For example, $G^1$ is phenyl, cyclobutyl or furanyl, wherein each ring is independently unsubstituted or further substituted as described in the summary. Examples of the substituents on $G^1$ include, but are not limited to, alkyl (for example methyl, ethyl), halogen, haloalkyl (for example difluoromethyl, trifluoromethyl, and the like), and —$OR^1$ (wherein $R^1$ is hydrogen, methyl, ethyl, difluoromethyl, or trifluoromethyl). Preferably, each $G^1$ is independently unsubstituted or substituted with 1, 2, or 3 substituents selected from the group consisting of trifluoromethyl and trifluoromethoxy.

In another embodiment, where A is substituted with —$Y^1$—$Y^3$, $Y^1$ is O, $N(R^w)$, —$N(R^w)C(O)$—, —$N(R^w)C(O)N(R^w)$—, or —$C(O)O$—, wherein the right side of the —$N(R^w)C(O)$—, and —$C(O)O$— moieties are connected to $Y^3$, $R^w$ is hydrogen, and $Y^3$ is hydrogen, alkyl, cycloalkyl, heteroaryl such as furanyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl, heterocycle or aryl. Examples of $Y^3$ include, but are not limited to, hydrogen. $C_{1-6}$ alkyl, cycloalkyl, furanyl, isoxazolyl, pyridinyl, phenyl or heterocycle such as 2,3-dihydro-1,4-benzodioxin-2-yl, 2H-chromen-4-yl, tetrahydrofuranyl or tetrahydropyranyl. Preferably, $Y^3$ is hydrogen, methyl, ethyl, adamentyl, cyclobutyl, cyclopentyl, cyclohexyl, phenyl, tetrahydrofuranyl, or tetrahydropyranyl. Each ring as represented by $Y^3$ is independently unsubstituted or further substituted as described in the summary section. Examples of the substituents of $Y^3$ include, but are not limited to, oxo, —OR$^1$ (wherein R$^1$ is hydrogen, C$_{1-6}$ alkyl or C$_{1-6}$ haloalkyl), haloalkyl (for example, trifluoromethyl, difluoromethyl), halogen, and alkyl such as C$_{1-6}$ alkyl. In one embodiment, each ring as represented by $Y^3$ is independently unsubstituted or further substituted with one, two, or three substituents selected from the group consisting of oxo, —OH, —O(methyl), —O(ethyl), —O(difluoromethyl), —O(trifluoromethyl), difluoromethyl, trifluoromethyl, Cl, Br, F, I, methyl, and ethyl.

A further embodiment is directed towards compounds where A is substituted with —Y$^1$—(CR$^e$R$^f$)$_q$—Y$^3$, Y$^1$ is O, R$^e$ is hydrogen or alkyl such as C$_{1-6}$ alkyl (preferably methyl), R$^f$ is hydrogen, alkyl such C$_{1-6}$ alkyl (preferably methyl), or —OH; q is 1, 2, 3, or 4, preferably, q is 1 or 2a, and $Y^3$ is cycloalkyl, heterocycle, heteroaryl, or aryl, each of which is independently unsubstituted or substituted as described in the summary section. Examples of $Y^3$ include, but are not limited to, adamentyl, C$_{1-6}$ cycloalkyl, heterocycle, heteroaryl such as furanyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl, or phenyl. Preferably, $Y^3$ is adamantyl, phenyl, furanyl, pyridinyl, isoxazolyl, cyclopropyl, cyclobutyl, cyclopentyl, cyclohexyl, 2,3-dihydro-1,4-benzodioxin-2-yl, 2H-chromen-4-yl, tetrahydrofuranyl or tetrahydro-2H-pyranyl, wherein each ring can be unsubstituted or further substituted as described in the summary section. Examples of the substituents of $Y^3$ include, but are not limited to, oxo, —OR$^1$ (wherein R$^1$ is hydrogen, C$_{1-6}$ alkyl or C$_{1-6}$ haloalkyl), haloalkyl (for example, C$_{1-6}$ haloalkyl such as difluoromethyl, trifluoromethyl), halogen, and alkyl such as C$_{1-6}$ alkyl. For example, each ring as represented by $Y^3$ is independently unsubstituted or further substituted with one, two, or three substituents selected from the group consisting of oxo, —OH, —O(methyl), —O(ethyl), —O(difluoromethyl), —O(trifluoromethyl), difluoromethyl, trifluoromethyl, Cl, Br, F, I, methyl, and ethyl.

In another embodiment, where A is substituted with —Y$^1$—(CR$^e$R$^f$)$_q$—Y$^2$—Y$^3$, q is 1, 2, 3 or 4, R$^e$ is hydrogen or alkyl such as C$_{1-6}$ alkyl (preferably methyl), and R$^f$ is hydrogen, alkyl such as C$_{1-6}$ alkyl (e.g. methyl), or —OH, Y$^1$ is O, Y$^2$ is O or C(O), and $Y^3$ is hydrogen, alkyl such as C$_{1-6}$ alkyl, cycloalkyl, heterocycle, heteroaryl or aryl, each ring as represented by $Y^3$ is independently unsubstituted or substituted as described in the summary section. Examples of $Y^3$ include, but are not limited to, hydrogen, C$_{1-6}$ alkyl, adamentyl. Cue cycloalkyl, heterocycle, heteroaryl such as furanyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl, or phenyl. Preferably, $Y^3$ is hydrogen, methyl, ethyl, adamantyl, phenyl, furanyl, pyridinyl, isoxazolyl, cyclopropyl, cyclobutyl, cyclopentyl, cyclohexyl, 2,3-dihydro-1,4-benzodioxin-2-yl, 2H-chromen-4-yl, tetrahydrofuranyl or tetrahydro-2H-pyranyl, wherein each ring is independently unsubstituted or further substituted as described in the summary section. Examples of the substituents of $Y^3$ include, but are not limited to, oxo, —OR$^1$ (wherein R$^1$ is hydrogen, C$_{1-6}$ alkyl or C$_{1-6}$ haloalkyl), haloalkyl (for example, C$_{1-6}$ haloalkyl such as difluoromethyl, trifluoromethyl, and the like), halogen, and alkyl such as C$_{1-6}$ alkyl. Each ring as represented by $Y^3$ can be unsubstituted or substituted wraith one, two, or three substituents selected from the group consisting of oxo, —OH, —O(methyl), —O(ethyl), —O(difluoromethyl), —O(trifluoromethyl), difluoromethyl, trifluoromethyl, Cl, Br, F, I, methyl, and ethyl.

In one embodiment, A is unsubstituted.
In yet another embodiment, A is formula (a)

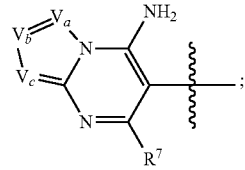

wherein V$_a$, V$_b$, V$_c$, and R$_7$ are as defined in the summary section. In one embodiment, V$_a$ is N, V$_b$ is C(R$^5$), and V$_c$ is C(R$^6$). In another embodiment, V$_a$ is N, V$_b$ is C(R$^5$), and V$_c$ is N. In yet another embodiment, V$_a$ is C(R$^4$), V$_b$ is C(R$^5$), and V$_c$ is N. Examples of R$^4$ include, but are not limited to, hydrogen and heterocycle such as morpholinyl. Examples of R$^5$ include, but are not limited to, hydrogen, C$_{1-6}$ alkyl such as methyl, —OR$^b$ such as —OH and —O(C$_{1-6}$ alkyl), —SR$^b$ (wherein R$^b$ is C$_{1-6}$ alkyl such as methyl), aryl such as phenyl, heteroaryl such as thienyl, and cycloalkyl such as cyclopropyl. Examples of R$^6$ include, but are not limited to, hydrogen and aryl such as phenyl. Examples of R$^7$ include, but are not limited to, hydrogen and C$_{1-6}$ alkyl (for example methyl, ethyl). Alternatively, R$^4$ and R$^5$ together with the carbon atoms to which they are attached form a phenyl ring, unsubstituted or substituted as described in the summary. Each of the aryl, cycloalkyl, heterocycle and heteroaryl of R$^4$, R$^5$ and R$^6$ are independently further optionally substituted as described in the summary. Examples of the optional substituents include, but are not limited to, C$_{1-6}$ alkyl (for example, methyl), halogen, C$_{1-6}$ haloalkyl (e.g. trifluoromethyl, difluoromethyl), OH, —O(methyl), —O(trifluoromethyl), and —O(difluoromethyl).

R$^x$, R$^y$, R$^{za}$ and R$^{zb}$, at each occurrence, are independently hydrogen, alkyl, or haloalkyl. In one embodiment, R$^x$, R$^y$, R$^{za}$ and R$^{zb}$ are hydrogen or C$_{1-6}$ alkyl (for example, methyl). In yet another embodiment, R$^{za}$ is hydrogen and R$^x$, R$^y$ and R$^{zb}$ are hydrogen or methyl. In a further embodiment, R$^x$, R$^y$, R$^{za}$ and R$^{zb}$ are hydrogen.

r and s are independently 1 or 2. In one embodiment, r and s are 2. Accordingly, one embodiment of the invention is directed to compounds of formula (Ia) or pharmaceutically acceptable salt thereof,

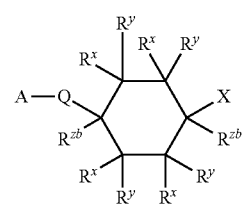

wherein A, Q, R$^x$, R$^y$, X, R$^{za}$, and R$^{zb}$ have values as described in the Summary and the Detailed Description sections.

X is X$^1$, —CR$^k$R$^m$)$_u$—X$^1$, —(CR$^k$R$^m$)$_u$—C(O)—X$^2$ or —C(O)—X$^2$, wherein R$^k$R$^m$, u, X$^1$ and X$^2$ are as set forth in the summary section.

In one embodiment, X is X$^1$ or —(CR$^k$R$^m$)$_u$—X$^1$, wherein u, R$^k$ and R$^m$, and X$^1$ are as described in the summary section. Preferably, u is 1 or 2, R$^k$ and R$^m$, at each occurrence, are independently hydrogen, alkyl such as $C_{1-6}$ alkyl, or haloalkyl such as $C_{1-6}$ haloalkyl, preferably. $R^k$ and $R^m$ are hydrogen or methyl. $X^1$ is heteroaryl such as furanyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. For example, $X^1$ is tetrazolyl, oxazolyl, or oxadiazolyl (including 1,2,4-oxadiazolyl, 1,3,4-oxadiazolyl). Each ring as represented by $X^1$ is optionally substituted as described in the summary section.

In another embodiment, X is $—(CR^kR^m)_u—C(O)—X^2$, wherein u is 1 or 2, $R^k$ and $R^m$, at each occurrence, are independently hydrogen, alkyl such as $C_{1-6}$ alkyl (for example, methyl), or haloalkyl such as $C_{1-6}$ haloalkyl. Examples of $R^k$ and $R^m$ include, but are not limited to, hydrogen and methyl. Preferably, $R^k$ and $R^m$ are hydrogen. $X^2$ is $—OR^{11}$ (wherein $R^{11}$ is hydrogen, $C_{1-6}$ alkyl, $C_{1-6}$ haloalkyl, arylalkyl or heteroarylalkyl, for example, $R^{11}$ is hydrogen, methyl, ethyl, n-propyl, isopropyl, tert-butyl, trifluoromethyl, or benzyl), $—N(R^w)—(CR''R^q)_w—C(O)OR^{11}$ (wherein $R^w$, $R''$, and $R^q$ are each independently hydrogen or methyl, w is 1 and $R^{11}$ is hydrogen, $C_{1-6}$ alkyl, $C_{1-6}$ haloalkyl, arylalkyl or heteroarylalkyl, for example, $R^{11}$ is hydrogen, methyl, ethyl, n-propyl, isopropyl, tert-butyl, trifluoromethyl or benzyl), heterocycle (such as pyrrolidinyl substituted with one substituent selected from the group consisting of $—C(O)NH_2$ and $—C(O)OR^1$ wherein $R^1$ is hydrogen, methyl, ethyl, n-propyl, isopropyl or tert-butyl), or $—N(R^w)(R^3)$ (wherein $R^w$ is hydrogen or methyl, $R^3$ is hydrogen, $C_{1-6}$ alkyl such as methyl, ethyl, n-propyl, or isopropyl, $—OH$, heteroaryl such as tetrazolyl which is unsubstituted or substituted as described in the summary section, or $—S(O)_2R^1$ wherein $R^1$ is $C_{1-6}$ alkyl such as methyl, ethyl, n-propyl or isopropyl, preferably. $R^1$ is methyl).

In yet another embodiment, X is $—CH_2C(O)OH$.

In another embodiment, X is $—C(O)—X^2$, wherein $X^2$ is $—OR^{11}$ and $R^{11}$ is as defined in the summary. Examples of $R^{11}$ include, but are not limited to, hydrogen, $C_{1-6}$ alkyl such as methyl, ethyl, n-propyl, isopropyl and tert-butyl, arylalkyl such as benzyl, and heteroarylalkyl. Preferably, $R^{11}$ is hydrogen.

In another embodiment, X is $—C(O)—X^2$, wherein $X^2$ is $—N(R^w)(R^3)$ and $R^w$ and $R^3$ are as described in the summary. Examples of $R^w$ and $R^3$ include, but are not limited to, hydrogen, and $C_{1-6}$ alkyl such methyl or ethyl.

It is appreciated that the present invention contemplates compounds of formula (I) having combinations of the above embodiments, including preferable and more preferable embodiments.

Accordingly, one aspect of the invention relates to compounds of formula (I), or a pharmaceutically acceptable salt, prodrug, salt of a prodrug, or a combination thereof, are those wherein X is $—(CR^kR^m)_u—C(O)—X^2$ or $C(O)—X^2$, and u, $R^k$, $R^k$, $R^m$, $X^2$ A, Q, $R^x$, $R^w$, $R^y$, $R^{za}$, $R^{zb}$, r, and s are as described in the Summary and the Detailed Description sections. $R^k$ and $R^m$ are, for example, independently hydrogen or $C_{1-6}$ alkyl (for example, methyl). Preferably, u is 1 or 2. $X^2$, for example, is $—OR^{11}$, heterocycle (unsubstituted or substituted as described in the summary section), $—N(R^w)(R^3)$, or $—N(R^w)—(CR''R^q)_w—(O)OR^{11}$ wherein w is 1, $R^w$, $R''$ and $R^q$ are each independently hydrogen or methyl. $R^3$ is hydrogen, $C_{1-6}$ alkyl such as methyl, ethyl, n-propy, or isopropy, $—OH$, heteroaryl (unsubstituted or substituted as described in the summary section), or $—S(O)_2R^1$ wherein $R^1$ is $C_{1-6}$ alkyl, and $R^{11}$ is hydrogen, $C_{1-6}$ alkyl, $C_{1-6}$ haloalkyl, arylalkyl, or heteroarylalkyl. More preferably, u is 1 or 2, $X^2$ is $—OR^{11}$, pyrrolidinyl (unsubstituted or substituted as described in the Summary section), $—N(R^w)(R^3)$, or $—N(R^w)—(CR''R^q)_w—C(O)OR^{11}$, wherein w is 1, $R^w$, $R''$, and $R^q$ are each independently hydrogen or methyl, $R^3$ is hydrogen, $C_{1-6}$ alkyl such as methyl or ethyl, $—OH$, tetrazolyl (unsubstituted or substituted as described in the summary section), or $—S(O)_2R^1$ wherein $R^1$ is methyl, and $R^{11}$ is hydrogen, methyl, ethyl, n-propyl, isopropyl, tert-butyl, or benzyl. In one embodiment, X is $—(CR^kR^m)_u—C(O)—X^2$ or $C(O)—X^2$ wherein u is 1 or 2, $R^k$ and $R^m$ are independently hydrogen or methyl, and $X^2$ is $—OR^{11}$ wherein $R^{11}$ is hydrogen.

Another aspect of the invention is related to a group of compounds of formula (I), or a pharmaceutically acceptable salt, prodrug, salt of a prodrug, or a combination thereof, wherein X is $—CR^kR^m)_u—C(O)—X^2$, Q is phenyl, optionally substituted with 1, 2 or 3 T, and u, $R^k$, $R^m$, $X^2$, A, T, $R^x$, $R^y$, $R^{za}$, $R^{zb}$, r, and s are as described in the Summary and the Detailed Description sections. For example Q is phenyl, unsubstituted or substituted with 1, 2, or 3 halogen. Preferably, u is 1 or 2. Examples of $X^2$ include, but are not limited to, $—OR^{11}$, heterocycle (unsubstituted or substituted as described in the summary section), $—N(R^w)(R^3)$ or $—N(R^w)—(CR''R^q)_w—C(O)OR^{11}$ wherein w is 1, $R^w$, $R''$, and $R^q$ are each independently hydrogen or methyl, $R^3$ is hydrogen. $C_{1-6}$ alkyl such as methyl, ethyl, n-propyl, or isopropyl, $—OH$, heteroaryl (unsubstituted or substituted as described in the summary section), or $—S(O)_2R^1$ wherein $R^1$ is $C_{1-6}$ alkyl, and $R^{11}$ is hydrogen, $C_{1-6}$ alkyl, $C_{1-6}$ haloalkyl, arylalkyl or heteroarylalkyl. More preferably, u is 1 or 2, $X^2$ is $—OR^{11}$, pyrrolidinyl (unsubstituted or substituted as described in the summary section), $—N(R^w)(R^3)$, or $—N(R^w)—(CR''R^q)_w—C(O)OR^{11}$ wherein w is 1, $R^w$, $R''$, and $R^q$ are each independently hydrogen or methyl, $R^3$ is hydrogen, methyl, ethyl, $—OH$, tetrazolyl (unsubstituted or substituted as described in the summary section), or $—S(O)_2 R^1$ wherein $R^1$ is methyl, and $R^{11}$ is hydrogen, methyl, ethyl, n-propyl, isopropyl, tert-butyl, or benzyl. In one embodiment, X is $—(CR^kR^m)_u—C(O)—X^2$ wherein u is 1 or 2, $R^k$ and $R^m$ are independently hydrogen or methyl, and $X^2$ is $—OR^{11}$ wherein $R^{11}$ is hydrogen.

Within this group of compounds. A, $R^x$, $R^y$, $R^{za}$ and $R^{zb}$ are as described in the Summary and the Detailed Description sections. Examples of $R^x$, $R^y$, $R^{za}$ and $R^{zb}$ include, but are not limited to, hydrogen or $C_{1-6}$ alkyl (for example, methyl). In one embodiment, A is optionally substituted phenyl. In another embodiment, A is an optionally substituted monocyclic heterocycle ring. For example, A is optionally substituted 2,5-dihydro-1H-pyrazol-3-yl. In yet another embodiment, A is an optionally substituted 5- or 6-membered monocyclic heteroaryl. Examples of A as a heteroaryl ring include, but are not limited to, furanyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. Preferably, A is pyrazolyl, triazolyl, thiazolyl, oxazolyl, or pyrazinyl. More preferably, A is pyrazolyl or triazolyl. Each A is optionally further substituted as described hereinabove. In a further embodiment, A is formula (a) wherein $V_a$, $V_b$, $V_c$, and $R_7$ are as defined in the summary section. In one embodiment, $V_a$ is N, $V_b$ is $C(R^5)$, and $V_c$ is $C(R^6)$. In another embodiment, $V_a$ is N, $V_b$ is $C(R^5)$, and $V_c$ is N. In yet another embodiment, $V_a$ is $C(R^4)$, $V_b$ is $C(R^5)$, and $V_c$ is N. Examples of $R^4$ include, but are not limited to, hydrogen and heterocycle such as morpholinyl. Examples of $R^5$ include, but are not limited to, hydrogen. $C_{1-6}$ alkyl such as methyl, $—OR^b$ such as $—OH$ and $—O(C_{1-6}$ alkyl), $—SR^b$ (wherein $R^b$ is $C_{1-6}$ alkyl such as methyl), aryl such as phenyl, heteroaryl such as thienyl, and cycloalkyl such as cyclopropyl. Examples of $R^6$ include, but are not limited to, hydrogen and aryl such as phenyl. Examples of $R^7$ include, but are not limited to, hydrogen and $C_{1-6}$ alkyl (for example methyl, ethyl). Alternatively, $R^4$ and $R^5$ together with the carbon atoms to which they are attached form a phenyl ring, unsubstituted or substituted as described in the summary. Each of the aryl, cycloalkyl, heterocycle, and heteroaryl of $R^4$, $R^5$ and $R^6$ are independently further optionally substituted as described in the summary and the Detailed Description sections.

Of this group of compounds, examples of a subgroup include those wherein r is 2 and s is 2.

Of this group of compounds, examples of a subgroup include those wherein r is 2 and s is 1.

Of this group of compounds, examples of a subgroup include those wherein r is 1 and s is 2.

In another aspect of the invention, there are provided compounds of formula (I), or a pharmaceutically acceptable salt, prodrug, salt of a prodrug, or a combination thereof, wherein X is —$(CR^kR^m)_u$—C(O)—$X^2$, Q is monocyclic heteroaryl optionally further substituted with 1, 2, or 3 substituents as represented by T, and u, $R^k$, $R^m$, $X^2$, A, T, $R^x$, $R^y$, $R^{za}$, $R^{zb}$, r, and s are as described in the Summary and the Detailed Description sections. For example, Q is pyridinyl, unsubstituted or further substituted with 1, 2, or 3 halogens. $R^k$ and $R^m$ are, for example, independently hydrogen or $C_{1-6}$ alkyl (for example, methyl). Preferably, u is 1 or 2. Examples of $X^2$ include, but are not limited to, —$OR^{11}$, heterocycle (unsubstituted or substituted as described in the summary section), —$N(R^w)(R^3)$, or —$N(R^w)$—$(CR''R^q)$—$C(O)OR^{11}$ wherein w is 1, $R^w$, $R''$, and $R^q$ are independently hydrogen or methyl, $R^3$ is hydrogen, $C_{1-6}$ alkyl such as methyl, ethyl, n-propyl, or isopropyl, —OH, heteroaryl (unsubstituted or substituted as described in the summary section), or —$S(O)_2R^1$ wherein $R^1$ is $C_{1-6}$ alkyl, and $R^{11}$ is hydrogen, $C_{1-6}$ alkyl, $C_{1-6}$ haloalkyl, arylalkyl, or heteroarylalkyl. More preferably, u is 1 or 2, $X^2$ is —$OR^{11}$, pyrrolidinyl (unsubstituted or substituted as described in the summary section), —$N(R^w)(R^3)$ or —$N(R^w)$—$(CR''R^q)_w$—$C(O)OR^{11}$ wherein w is 1, $R^w$, $R''$, and $R^q$ are independently hydrogen or methyl. $R^3$ is hydrogen, methyl, ethyl, —OH, tetrazolyl (unsubstituted or substituted as described in the summary section), or —$S(O)_2R^1$ wherein $R^1$ is methyl, and $R^{11}$ is hydrogen, methyl, ethyl, n-propyl, isopropyl, tert-butyl, or benzyl. In one embodiment, X is —$(CR^kR^m)_u$—C(O)—$X^2$ wherein u is 1 or 2, $R^k$ and $R^m$ are independently hydrogen or methyl, and $X^2$ is —$OR^{11}$ wherein $R^{11}$ is hydrogen.

Within this group of compounds, A, $R^x$, $R^y$, $R^{za}$ and $R^{zb}$ are as defined in the summary. Examples of $R^x$, $R^y$, $R^{za}$ and $R^{zb}$ include, but are not limited to, hydrogen or $C_{1-6}$ alkyl (for example, methyl). In one embodiment, A is optionally substituted phenyl. In another embodiment, A is an optionally substituted monocyclic heterocycle ring. For example, A is optionally substituted 2,5-dihydro-1H-pyrazol-3-yl. In yet another embodiment, A is an optionally substituted 5- or 6-membered monocyclic heteroaryl. Examples of A as a heteroaryl ring include, but are not limited to, furanyl, imidazolyl, isoxazolyl, isothiazolyl, oxadiazolyl, oxazolyl, pyridinyl, pyridazinyl, pyrimidinyl, pyrazinyl, pyrazolyl pyrrolyl, tetrazolyl, thiadiazolyl, thiazolyl, thienyl, triazolyl, and triazinyl. Preferably, A is pyrazolyl, triazolyl, thiazolyl, oxazolyl, or pyrazinyl. More preferably, A is pyrazolyl or triazolyl. Each A is optionally further substituted as described in the Summary and the Detailed Description sections. In a further embodiment, A is formula (a) wherein $V_a$, $V_b$, $V_c$, and $R_7$ are as defined in the summary section. In one embodiment, $V_a$ is N, $V_b$ is $C(R^5)$, and $V_c$ is $C(R^6)$. In another embodiment, $V_a$ is N, $V_b$ is $C(R^5)$, and $V_c$ is N. In yet another embodiment, $V_a$ is $C(R^4)$, $V_b$ is $C(R^5)$, and $V_c$ is N. Examples of $R^4$ include, but are not limited to, hydrogen and heterocycle such as morpholinyl. Examples of $R^5$ include, but are not limited to, hydrogen, $C_{1-6}$ alkyl such as methyl, —$OR^b$ such as —OH and —$O(C_{1-6}$ alkyl), —$SR^b$ (wherein $R^b$ is $C_{1-6}$ alkyl such as methyl), aryl such as phenyl, heteroaryl such as thienyl, and cycloalkyl such as cyclopropyl. Examples of $R^6$ include, but are not limited to, hydrogen and aryl such as phenyl. Examples of $R^7$ include, but are not limited to, hydrogen and $C_{1-6}$ alkyl (for example methyl, ethyl). Alternatively, $R^4$ and $R^5$ together with the carbon atoms to which they are attached form a phenyl ring, unsubstituted or substituted as described in the summary. Each of the aryl, cycloalkyl, heterocycle and heteroaryl of $R^4$, $R^5$ and $R^6$ are independently further optionally substituted as described in the summary and the Detailed Description sections.

Of this group of compounds, examples of a subgroup include those wherein r is 2 and s is 2.

Of this group of compounds, examples of a subgroup include those wherein r is 2 and s is 1.

Of this group of compounds, examples of a subgroup include those wherein r is 1 and s is 2.

Yet another aspect of the invention provides compounds of formula (I) wherein X is —C(O)—$X^2$, Q is phenyl optionally further substituted with 1, 2, or 3 T, and $X^2$, r, s, T, $R^x$, $R^y$, $R^{za}$, $R^{zb}$, and A are as described in the Summary and the Detailed Description sections. For example, Q is phenyl, unsubstituted or substituted with 1, 2 or 3 halogen. For example, $X^2$ is —$OR^{11}$ or $N(R^w)(R^3)$ wherein $R^{11}$, $R^w$, and $R^3$ are as disclosed in the Summary and the Detailed Description sections. Examples of $R^{11}$ include, but are not limited to, hydrogen, $C_{1-6}$ alkyl such as methyl, ethyl, n-propyl, isopropyl, and tert-butyl, or arylalkyl such as benzyl. Preferably, $R^{11}$ is hydrogen Examples of $R^w$ and $R^3$ include, but are not limited to, hydrogen and $C_{1-6}$ alkyl such as, but are not limited to, methyl and ethyl.

Within this group of compounds. A, $R^x$, $R^y$, $R^{za}$ and $R^{zb}$ are as defined in the summary. Examples of $R^x$, $R^y$, $R^{za}$ and $R^{zb}$ include, but are not limited to, hydrogen or $C_{1-6}$ alkyl (for example, methyl). In one embodiment, A is optionally substituted phenyl. In another embodiment, A is an optionally substituted monocyclic heterocycle ring. For example, A is optionally substituted 2,5-dihydro-1H-pyrazol-3-yl. In yet another embodiment, A is an optionally substituted 5- or 6-membered monocyclic heteroaryl. Examples of A as a heteroaryl ring include, but are not limited to, furanyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. Preferably, A is pyrazolyl, triazolyl, thiazolyl, oxazolyl, or pyrazinyl. More preferably, A is pyrazolyl or triazolyl. Each A is optionally further substituted as described in the Summary and the Detailed Description sections. In a further embodiment, A is formula (a) wherein $V_a$, $V_b$, $V_c$, and $R_7$ are as defined in the summary section. In one embodiment, $V_a$ is N, $V_b$ is $C(R^5)$, and $V_c$ is $C(R^6)$. In another embodiment, $V_a$ is N, $V_b$ is $C(R^5)$, and $V_c$ is N. In yet another embodiment, $V_a$ is $C(R^4)$, $V_b$ is $C(R^5)$, and $V_c$ is N. Examples of $R^4$ include, but are not limited to, hydrogen and heterocycle such as morpholinyl. Examples of $R^5$ include, but are not limited to, hydrogen, $C_{1-6}$ alkyl such as methyl, —$OR^b$ such as —OH and —$O(C_{1-6}$ alkyl), —$SR^b$ (wherein $R^b$ is $C_{1-6}$ alkyl such as methyl), aryl such as phenyl, heteroaryl such as thienyl, and cycloalkyl such as cyclopropyl. Examples of $R^6$ include, but are not limited to, hydrogen and aryl such as phenyl. Examples of $R^7$ include, but are not limited to, hydrogen and $C_{1-6}$ alkyl (for example methyl, ethyl). Alternatively, $R^4$ and $R^5$ together with the carbon atoms to which they are attached form a phenyl ring, unsubstituted or substituted as described in the summary. Each of the aryl, cycloalkyl, heterocycle and heteroaryl of $R^4$, $R^5$ and $R^6$ are independently further optionally substituted as described in the summary and the Detailed Description sections.

Of this group of compounds, examples of a subgroup include those wherein r is 2 and s is 2.

Of this group of compounds, examples of a subgroup include those wherein r is 2 and s is 1.

Of this group of compounds, examples of a subgroup include those wherein r is 1 and s is 2.

In another aspect of the invention, there are provided compounds of formula (I), or a pharmaceutically acceptable salt, prodrug, salt of a prodrug, or a combination thereof, wherein X is —C(O)—$X^2$, Q is monocyclic heteroaryl, optionally substituted with 1, 2, or 3 substituents as represented by T, and $X^2$, A, T, $R^x$, $R^y$, $R^{za}$, $R^{zb}$, r, and s are as described in the summary and the Detailed Description sections. For example, Q is pyridinyl, unsubstituted or substituted with 1, 2, or 3 halogen. For example, $X^2$ is —$OR^{11}$ or $N(R^w)(R^3)$ wherein $R^{11}$, $R^w$, and $R^3$ are as disclosed in the Summary and Detailed Description sections. Examples of $R^{11}$ include, but are not limited to, hydrogen, $C_{1-6}$ alkyl such as methyl, ethyl, n-propyl, isopropyl or tert-butyl, or arylalkyl such as benzyl. Preferably, $R^{11}$ is hydrogen. Examples of $R^w$ and $R^3$ include, but are not limited to, hydrogen, and $C_{1-6}$ alkyl such as, but not limited to, methyl and ethyl.

Within this group of compounds, A, $R^x$, $R^y$, $R^{za}$ and $R^{zb}$ are as defined in the summary. Examples of $R^x$, $R^y$, $R^{za}$ and $R^{zb}$ include, but are not limited to, hydrogen or $C_{1-6}$ alkyl (for example, methyl). In one embodiment, A is optionally substituted phenyl. In another embodiment, A is an optionally substituted monocyclic heterocycle ring. For example, A is optionally substituted 2,5-dihydro-1H-pyrazol-3-yl. In yet another embodiment, A is an optionally substituted 5- or 6-membered monocyclic heteroaryl. Examples of A as a heteroaryl ring include, but are not limited to, furanyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. Preferably, A is pyrazolyl, triazolyl, thiazolyl, oxazolyl, or pyrazinyl. More preferably, A is pyrazolyl or triazolyl. Each A is optionally further substituted as described in the Summary and the Detailed Description sections. In a further embodiment, A is formula (a) wherein $V_a$, $V_b$, $V_c$, and $R_7$ are as defined in the summary section. In one embodiment, $V_a$ is N, $V_b$ is $C(R^5)$, and $V_c$ is $C(R^6)$. In another embodiment, $V_a$ is N, $V_b$ is $C(R^5)$, and $V_c$ is N. In yet another embodiment, $V_a$, is $C(R^4)$, $V_b$ is $C(R^5)$, and $V_c$ is N. Examples of $R^4$ include, but are not limited to, hydrogen and heterocycle such as morpholinyl. Examples of $R^5$ include, but are not limited to, hydrogen, $C_{1-6}$ alkyl such as methyl, —$OR^b$ such as —OH and —$O(C_{1-6}$ alkyl), —$SR^b$ (wherein $R^h$ is $C_{1-6}$ alkyl such as methyl), aryl such as phenyl, heteroaryl such as thienyl, and cycloalkyl such as cyclopropyl. Examples of $R^6$ include, but are not limited to, hydrogen and aryl such as phenyl. Examples of $R^7$ include, but are not limited to, hydrogen and $C_{1-6}$ alkyl (for example methyl, ethyl). Alternatively, $R^4$ and $R^5$ together with the carbon atoms to which they are attached form a phenyl ring, unsubstituted or substituted as described in the summary. Each of the aryl, cycloalkyl, heterocycle and heteroaryl of $R^4$, $R^5$ and $R^6$ are independently further optionally substituted as described in the summary and the Detailed Description sections.

Of this group of compounds, examples of a subgroup include those wherein r is 2 and s is 2.

Of this group of compounds, examples of a subgroup include those wherein r is 2 and s is 1.

Of this group of compounds, examples of a subgroup include those wherein r is 1 and s is 2.

A further aspect of the invention is related to compounds of formula (Ia), or a pharmaceutically acceptable salt, prodrug, salt of a prodrug thereof, wherein A, Q, T, $R^x$, $R^y$, $R^{za}$, $R^{zb}$, and X in formula (Ia) are as described in formula (I). One embodiment is directed to compounds of formula (Ia) wherein Q is phenyl. Such compounds can exist as the cis isomers or the trans isomers. Thus, one embodiment of the invention is directed to the trans isomers as represented by formula (Ib), it is understood that the structural drawing of (Ib) encompasses not only one trans isomer as depicted in (Ib), but also other trans isomers (for example, (Ic)), and mixtures (including racemates) thereof.

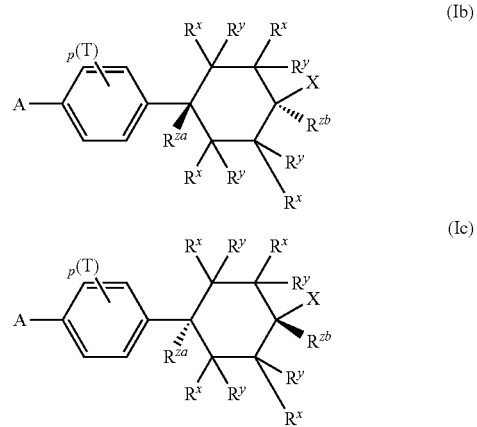

wherein p is 0.1, 2, or 3, and A, T, $R^x$, $R^y$, $R^{za}$, $R^{zb}$, and X in formula (Ib) and (Ic) are as described in formula (I). It is understood that embodiments of the variables, and combinations of embodiments, including preferable, and more preferable embodiments as described in formula (I) are also contemplated for compounds of formulae (Ia), (Ib), and (Ic).

Thus, examples of a group of compounds having formula (Ia) or (Ib), or a pharmaceutically acceptable salt, prodrug, salt of a prodrug, or a combination thereof, include those wherein X is —$(CR^kR^m)_u$—C(O)—$X^2$ or C(O)—$X^2$ and u, T, $R^k$, $R^m$, $X^2$, A, $R^x$, $R^y$, $R^{za}$ and $R^{zb}$ are as described in the Summary and the Detailed Description sections. For example, T is halogen. Preferably, u is 1 or 2, $R^k$, $R^m$, $R^x$, $R^y$, $R^{za}$, and $R^{zb}$, are, for example, each independently hydrogen or $C_{1-6}$ alkyl (e.g. methyl). Examples of $X^2$ include, but not limited to, —$OR^{11}$, heterocycle (unsubstituted or substituted as described in the summary section), —$N(R^w)(R^3)$, and —$N(R^w)$—$(CR''R^q)_w$—$C(O)OR^{11}$ wherein w is 1, $R^w$, $R''$, and $R^q$ are each independently hydrogen or methyl, $R^3$ is hydrogen, $C_{1-6}$ alkyl such as, but not limited to, methyl, ethyl, n-propyl, or isopropyl, —OH, heteroaryl (unsubstituted or substituted as described in the summary section), or —$S(O)_2 R^1$ wherein $R^1$ is $C_{1-6}$ alkyl; and $R^{11}$ is hydrogen, $C_{1-6}$ alkyl, $C_{1-6}$ haloalkyl, arylalkyl or heteroarylalkyl. More preferably, u is 1 or 2, $X^2$ is —$OR^{11}$, pyrrolidinyl (unsubstituted or substituted as described in the summary section), —$N(R^w)$ ($R^3$), or —$N(R^w)$—$(CR''R^q)_w$—$C(O)OR^{11}$, wherein w is 1, $R^w$, $R''$, and $R^q$ are each independently hydrogen or methyl. $R^3$ is hydrogen, $C_{1-6}$ alkyl such as, but not limited to, methyl, ethyl, n-propyl, or isopropyl, —OH, tetrazolyl (unsubstituted or substituted as described in the summary section), or —S(O)$_2$R$^1$ wherein R$^1$ is methyl, and R$^{11}$ is hydrogen, methyl, ethyl, n-propyl, isopropyl, tert-butyl, or benzyl. In one embodiment, X is —(CR$^k$R$^m$)$_u$—C(O)—X$^2$ or C(O)—X$^2$ wherein u is 1 or 2, R$^k$ and R$^m$ are independently hydrogen or methyl, and X$^2$ is —OR$^{11}$ wherein R$^{11}$ is hydrogen.

Within this group of compounds of formula (Ia) or (Ib), examples of a subgroup include those wherein A is phenyl, optionally substituted as described in the Summary and the Detailed Description sections.

Examples of another subgroup include those wherein A is an optionally substituted 5- or 6-membered monocyclic heteroaryl ring. Examples of the monocyclic heteroaryl ring and its optional substituents are described in the Summary and the Detailed Description sections.

Examples of another subgroup include those wherein A is an optionally substituted 5- or 6-membered monocyclic heterocycle ring. Examples of monocyclic heterocycle ring and its optional substituents are described in the Summary and the Detailed Description sections.

Examples of yet another subgroup include those wherein A is formula (a) wherein V$_a$, V$_b$, V$_c$, and R$^7$ are as described in the Summary and the Detailed Description sections. In one embodiment, V$_a$ is N, V$_b$ is C(R$^5$), and V$_c$ is C(R$^6$). In another embodiment, V$_a$ is N, V$_b$ is C(R$^5$), and V$_c$ is N. In yet another embodiment, V$_a$ is C(R$^4$), V$_b$ is C(R$^5$), and V$_c$ is N. Examples of R$^4$ include, but are not limited to, hydrogen and heterocycle such as morpholinyl. Examples of R$^5$ include, but are not limited to, hydrogen, C$_{1-6}$ alkyl such as methyl, —OR$^b$ such as —OH and —O(C$_{1-6}$ alkyl), —SR$^b$ (wherein R$^b$ is C$_{1-6}$ alkyl such as methyl), aryl such as phenyl, heteroaryl such as thienyl, and cycloalkyl such as cyclopropyl. Examples of R$^6$ include, but are not limited to, hydrogen and aryl such as phenyl. Examples of R$^7$ include, but are not limited to, hydrogen and C$_{1-6}$ alkyl (for example methyl, ethyl). Alternatively, R$^4$ and R$^5$ together with the carbon atoms to which they are attached form a phenyl ring, unsubstituted or substituted as described in the summary. Each of the aryl, cycloalkyl, heterocycle and heteroaryl of R$^4$, R$^5$ and R$^6$ are independently further optionally substituted as described in the summary and the Detailed Description sections.

Another aspect of the present invention is directed to compounds of formula (I) wherein A is formula (a), Q is phenyl, r and s are 2. Accordingly, one embodiment of the present invention provides compounds of formula (II) or pharmaceutically acceptable salt thereof

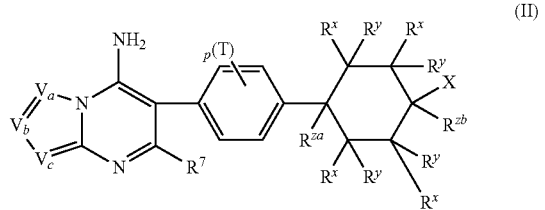

(II)

wherein p is 0, 1, 2, or 3, and V$_a$, V$_b$, V$_c$, R$^7$, T, R$^x$, R$^y$, R$^{za}$, R$^{zb}$, and X are as described in the Summary and the Detailed Description sections for formula (I). It is appreciated that such compounds can be in the form or cis or trans isomer. One embodiment is directed to the trans isomer of such compounds as depicted in formula (IIa). It is understood that the structural drawing of (IIa) encompasses not only one trans isomer as depicted in (IIa), but also other trans isomers (for example, (IIb)), and mixtures (including racemate) thereof.

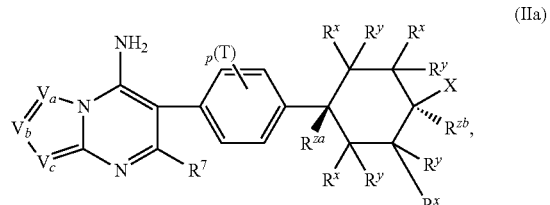

(IIa)

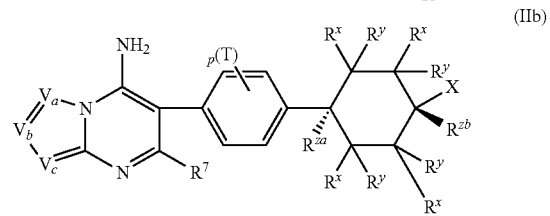

(IIb)

wherein p is 0, 1, 2, or 3, and V$_a$, V$_b$, V$_c$, R$^7$, T, R$^x$, R$^y$, R$^{za}$, R$^{zb}$, and X in formula (IIa) and (IIb) are as described in formula (I). It is understood that embodiments of V$_a$, V$_b$, V$_c$, R$^7$, T, R$^x$, R$^y$, R$^{za}$, R$^{zb}$, and X and combinations of embodiments, including preferable, and more preferable embodiments as described in formula (I) are also contemplated for compounds of formulae (II), (IIa) and (IIb).

Accordingly, examples of a group of compounds having formula (II) or (IIa), or a pharmaceutically acceptable salt, prodrug, salt of a prodrug, or a combination thereof, are those wherein X is —(CR$^k$R$^m$)$_u$—C(O)—X$^2$ or C(O)—X$^2$ and u, R$^k$, R$^m$, X$^2$, V$_a$, V$_b$, V$_c$, R$^7$, R$^x$, R$^y$, R$^{za}$, and R$^{zb}$ are as described in the Summary and the Detailed Description sections. R$^7$, R$^x$, R$^y$, R$^{za}$, and R$^{zb}$, for example, are each independently hydrogen or C$_{1-6}$ alkyl (e.g. methyl). T, for example, is halogen. Preferably, u is 1 or 2. Examples of X$^2$ include —OR$^{11}$, heterocycle (unsubstituted or substituted as described in the summary section), —N(R$^w$)(R$^3$), and —N(R$^w$)—(CR$^n$R$^q$)$_w$—C(O)OR$^{11}$ wherein w is 1, R$^w$, R$^n$, and R$^q$ are each independently hydrogen or methyl, R$^3$ is hydrogen, C$_{1-6}$ alkyl such as, but not limited to, methyl, ethyl, n-propyl, or isopropyl, —OH, heteroaryl (unsubstituted or substituted as described in the summary section), or —S(O)$_2$R$^1$ wherein R$^1$ is C$_{1-6}$ alkyl, and R$^{11}$ is hydrogen, C$_{1-6}$ alkyl, C$_{1-6}$ haloalkyl, arylalkyl or heteroarylalkyl. More preferably, u is 1 or 2, X$^2$ is —OR$^{11}$, pyrrolidinyl (unsubstituted or substituted as described in the summary section), —N(R$^w$)(R$^3$), or —N(R$^w$)—(CR$^n$R$^q$)$_w$—C(O)OR$^{11}$, wherein w is 1, R$^w$, R$^n$, and R$^q$ are each independently hydrogen or methyl, R$^3$ is hydrogen, C$_{1-6}$ alkyl such as, but not limited to, methyl, ethyl, n-propyl, or isopropyl, —OH, tetrazolyl (unsubstituted or substituted as described in the summary section), or —S(O)$_2$R$^1$ wherein R$^1$ is methyl, and R$^{11}$ is hydrogen, methyl, ethyl, n-propyl, isopropyl, tert-butyl, or benzyl. In one embodiment, X is —(CR$^k$R$^m$)$_u$—C(O)—X$^2$ or C(O)—X$^2$ wherein u is 1 or 2, R$^k$ and R$^m$ are independently hydrogen or methyl, and X$^2$ is —OR$^{11}$ wherein R$^{11}$ is hydrogen.

Examples of another group of compounds of formula (II) or (IIa) include those wherein X is —(CR$^k$R$^m$)$_u$—X$^1$ wherein R$^k$, R$^m$, u, and X$^1$ are as described in the Summary and the Detailed Description sections. For example, R$^k$ and R$^m$ are hydrogen. For example, u is 1 or 2, X$^1$ is, for example, optionally substituted heteroaryl such as, but not limited to, optionally substituted 1,2,4-oxadiazolyl or 1,3,4-oxadiazolyl.

Examples of the optional substituents of $X^1$ are as described in the Detailed Description section.

Within these two groups of compounds of formula (II) or (IIa), examples of a subgroup include those wherein $V_a$ is N, $V_b$ is $C(R^5)$, and $V_c$ is $C(R^6)$, wherein $R^5$ and $R^6$ have values as set forth in the Summary and the Detailed Description sections.

Examples of another subgroup include those wherein $V_a$ is N, $V_b$ is $C(R^5)$, and $V_c$ is N, wherein $R^5$ has values as set forth in the Summary and the Detailed Description sections.

Yet other examples of a subgroup include those wherein $V_a$ is $C(R^4)$, $V_b$ is $C(R^5)$, and $V_c$ is, wherein $R^4$ and $R^5$ have values as set forth in the Summary and the Detailed Description sections.

Exemplary compounds include, but are not limited to,

Trans [4-(4-{3-[2-(1-adamantyl)-2-hydroxyethoxy]-1H-pyrazol-5-yl}phenyl)cyclohexyl]acetic acid;

Trans [4-(4-{3-[2-(1-adamantyl)-2-oxoethoxy]-1H-pyrazol-5-yl}phenyl)cyclohexyl]acetic acid;

Trans [4-(4-{3-[2-(4-methoxyphenyl)-2-oxoethoxy]-1H-pyrazol-5-yl}phenyl)cyclohexyl]acetic acid;

Trans {4-[4-(3-{[2-(trifluoromethoxy)benzyl]oxy}-1H-pyrazol-5-yl)phenyl]cyclohexyl}acetic acid;

Trans {4-[4-(3-{[5-(trifluoromethyl)-2-furyl]methoxy}-4-{[5-(trifluoromethyl)-2-furyl]methyl}-1H-pyrazol-5-yl)phenyl]cyclohexyl}acetic acid;

Trans {4-[4-(4-[2-(trifluoromethoxy)benzyl]-3-{[2-(trifluoromethoxy)benzyl]oxy}-1H-pyrazol-5-yl)phenyl]cyclohexyl}acetic acid;

Trans (4-{4-[3-(cyclohexylmethoxy)-1H-pyrazol-5-yl]phenyl}cyclohexyl)acetic acid;

Trans {4-[4-(3-{[3-(trifluoromethoxy)benzyl]oxy}-1H-pyrazol-5-yl)phenyl]cyclohexyl}acetic acid;

Trans {4-[4-(3-{[5-(trifluoromethyl)-2-furyl]methoxy}-1H-pyrazol-5-yl)phenyl]cyclohexyl}acetic acid;

Trans (4-{4-[3-(3-phenoxypropoxy)-1H-pyrazol-5-yl]phenyl}cyclohexyl)acetic acid;

Trans (4-{4-[3-(4-phenoxybutoxy)-1H-pyrazol-5-yl]phenyl}cyclohexyl)acetic acid;

Trans (4-{4-[3-(2,3-dihydro-1,4-benzodioxin-2-ylmethoxy)-1H-pyrazol-5-yl]phenyl}cyclohexyl)acetic acid;

Trans {4-[4-(3-{[2-(difluoromethoxy)benzyl]oxy}1H-pyrazol-5-yl)phenyl]cyclohexyl}acetic acid;

Trans (4-{4-[3-(cyclopentylmethoxy)-1H-pyrazol-5-yl]phenyl}cyclohexyl)acetic acid;

Trans (4-{4-[3-(cyclobutylmethoxy)-1H-pyrazol-5-yl]phenyl}cyclohexyl)acetic acid;

Trans (4-{4-[3-(cyclohexyloxy)-1H-pyrazol-5-yl]phenyl}cyclohexyl)acetic acid;

Trans (4-{4-[3-(tetrahydro-2H-pyran-2-ylmethoxy)-1H-pyrazol-5-yl]phenyl}cyclohexyl)acetic acid;

Trans ethyl [4-(4-{3-[2-(1-adamantyl)-2-oxoethoxy]-1H-pyrazol-5-yl}phenyl)cyclohexyl]acetate;

Trans (4-{4-[5-(cyclobutylmethoxy)-1-(cyclobutylmethyl)-1H-pyrazol-3-yl]phenyl}cyclohexyl)acetic acid;

Trans (4-{4-[3-(benzyloxy)-1H-pyrazol-5-yl]phenyl}cyclohexyl)acetic acid;

Trans (4-{4-[3-(cyclopentyloxy)-1H-pyrazol-5-yl]phenyl}cyclohexyl)acetic acid;

Trans {4-[4-(3-{[4-(trifluoromethyl)benzyl]oxy}-1H-pyrazol-5-yl)phenyl]cyclohexyl}acetic acid;

Trans [4-(4-{3-[(5-methylisoxazol-3-yl)methoxy]-1H-pyrazol-5-yl}phenyl)cyclohexyl]acetic acid;

Trans {4-[4-(1H-1,2,4-triazol-5-yl)phenyl]cyclohexyl}acetic acid;

Trans [4-(4-{5-[(5-methylisoxazol-3-yl)methoxy]-1-[(5-methylisoxazol-3-yl)methyl]-1H-pyrazol-3-yl}phenyl)cyclohexyl]acetic acid;

Trans N-methyl-N-[(4-{4-[5-(trifluoromethyl)-1H-pyrazol-3-yl]phenyl}cyclohexyl)acetyl]glycine;

Trans (4-{4-[3-(cyclobutyloxy)-1H-pyrazol-5-yl]phenyl}cyclohexyl)acetic acid;

Trans (4-{4-[5-(trifluoromethyl)-1H-pyrazol-3-yl]phenyl}cyclohexyl)acetic acid;

Trans (4-{4-[3-(cyclopropylmethoxy)-1H-pyrazol-5-yl]phenyl}cyclohexyl)acetic acid;

Trans 2-(4-{4-[3-(cyclohexylmethoxy)-1H-pyrazol-5-yl]phenyl}cyclohexyl)-N-hydroxyacetamide;

Trans (4-{4-[3-(pyridin-2-ylmethoxy)-1H-pyrazol-5-yl]phenyl}cyclohexyl)acetic acid;

Trans (4-{4-[3-(tetrahydrofuran-2-ylmethoxy)-1H-pyrazol-5-yl]phenyl}cyclohexyl)acetic acid;

Trans (4-{4-[4-bromo-3-(cyclobutylmethoxy)-1H-pyrazol-5-yl]phenyl}cyclohexyl)acetic acid;

Trans N-hydroxy-2-(4-{4-[3-(trifluoromethyl)-1H-pyrazol-5-yl]phenyl}cyclohexyl)acetamide;

Trans N-(methylsulfonyl)-2-(4-{4-[3-(trifluoromethyl)-1-H-pyrazol-5-yl]phenyl}cyclohexyl)acetamide;

Trans 1-({4-[4-(1H-pyrazol-3-yl)phenyl]cyclohexyl}acetyl)-L-proline;

Trans {4-[4-(1H-pyrazol-3-yl)phenyl]cyclohexyl}acetic acid;

Trans (4-{4-[4-bromo-3-(cyclopropylmethoxy)-1H-pyrazol-5-yl]phenyl}cyclohexyl)acetic acid;

Trans ethyl [4-(4-{3-[2-(1-adamantyl)-2-hydroxyethoxy]-1H-pyrazol-5-yl}phenyl)cyclohexyl]acetate;

Trans methyl N-methyl-N-[(4-{4-[3-(trifluoromethyl)-1H-pyrazol-5-yl]phenyl}cyclohexyl)acetyl]glycinate;

Trans [4-(4-{3-[(6,7-dimethoxy-2-oxo-2H-chromen-4-yl)methoxy]-1H-pyrazol-5-yl}phenyl)cyclohexyl]acetic acid;

Trans N-2H-tetraazol-5-yl-2-(4-{4-[5-(trifluoromethyl)-1H-pyrazol-3-yl]phenyl}cyclohexyl)acetamide;

Trans methyl {4-[4-(3-{[2-(trifluoromethoxy)benzyl]oxy}-1H-pyrazol-5-yl)phenyl]cyclohexyl}acetate;

Trans ethyl 5-{4-[4-(2-ethoxy-2-oxoethyl)cyclohexyl]phenyl}-1H-pyrazole-3-carboxylate;

Trans [4-(4-{3-[(2-hydroxycyclohexyl)oxy]-1H-pyrazol-5-yl}phenyl)cyclohexyl]acetic acid;

Trans {4-[4-(3-hydroxy-1H-pyrazol-5-yl)phenyl]cyclohexyl}acetic acid;

Trans methyl (4-{4-[3-(cyclohexyloxy)-1H-pyrazol-5-yl]phenyl}cyclohexyl)acetate;

Trans [4-(4-{2-[(3-methoxyphenyl)amino]-1,3-thiazol-4-yl}phenyl)cyclohexyl]acetic acid;

Trans ethyl (4-{4-[5-(trifluoromethyl)-1H-pyrazol-3-yl]phenyl}cyclohexyl)acetate;

Trans 2-methyl-N-[(4-{4-[5-(trifluoromethyl)-1H-pyrazol-3-yl]phenyl}cyclohexyl)acetyl]alanine;

Trans {4-[4-(4-ethyl-1-methyl-1H-pyrazol-3-yl)phenyl]cyclohexyl}acetic acid;

Trans (4-{4-[3-(tetrahydro-2H-pyran-4-ylmethoxy)-1H-pyrazol-5-yl]phenyl}cyclohexyl)acetic acid;

Trans (4-{4-[4-bromo-3-(tetrahydro-2H-pyran-4-ylmethoxy)-1H-pyrazol-5-yl]phenyl}cyclohexyl)acetic acid;

Trans {4-[4-(2-{[2-(trifluoromethyl)phenyl]amino}-1,3-thiazol-4-yl)phenyl]cyclohexyl}acetic acid;

Trans [4-(4-{2-[(3,5-dichlorophenyl)amino]-1,3-thiazol-4-yl}phenyl)cyclohexyl]acetic acid;

Trans methyl (4-{4-[3-(cyclopentylmethoxy)-1H-pyrazol-5-yl]phenyl}cyclohexyl)acetate;

Trans ethyl {4-[4-(3-{[5-(trifluoromethyl)-2-furyl]methoxy}-1H-pyrazol-5-yl)phenyl]cyclohexyl}acetate;
Trans [4-(4-{2-[(2-chlorophenyl)amino]-1,3-thiazol-4-yl}phenyl)cyclohexyl]acetic acid;
Trans (4-{4-[1,2-bis(cyclobutylmethyl)-5-oxo-2,5-dihydro-1H-pyrazol-3-yl]phenyl}cyclohexyl)acetic acid;
Trans {4-[4-(2-{[3-(trifluoromethyl)phenyl]amino}-1,3-thiazol-4-yl)phenyl]cyclohexyl}acetic acid;
Trans methyl (4-{4-[3-(cyclopentyloxy)-1H-pyrazol-5-yl]phenyl}cyclohexyl)acetate;
Trans ethyl (4-{4-[3-(2,3-dihydro-1,4-benzodioxin-2-ylmethoxy)-1H-pyrazol-5-yl]phenyl}cyclohexyl)acetate;
Trans methyl 1-({4-[4-(1H-pyrazol-3-yl)phenyl]cyclohexyl}acetyl)-L-prolinate;
Trans [4-(4-{2-[(2-methylphenyl)amino]-1,3-thiazol-4-yl}phenyl)cyclohexyl]acetic acid;
Trans [4-(4-{2-[(4-chlorophenyl)amino]-1,3-thiazol-4-yl}phenyl)cyclohexyl]acetic acid;
Trans [4-(4-{2-[(3-chlorophenyl)amino]-1,3-thiazol-4-yl}phenyl)cyclohexyl]acetic acid;
Trans ethyl (4-{4-[3-(pyridin-2-ylmethoxy)-1H-pyrazol-5-yl]phenyl}cyclohexyl)acetate;
Trans ethyl (4-{4-[3-(tetrahydrofuran-2-ylmethoxy)-1H-pyrazol-5-yl]phenyl}cyclohexyl)acetate;
Trans (4-{4-[3-(tetrahydro-2H-pyran-4-yloxy)-1H-pyrazol-5-yl]phenyl}cyclohexyl)acetic acid;
Trans ethyl (4-{4-[2-(formylamino)-1,3-oxazol-4-yl]phenyl}cyclohexyl)acetate;
Trans 1-({4-[4-(1H-pyrazol-3-yl)phenyl]cyclohexyl}acetyl)-L-prolinamide;
Trans ethyl (4-{4-[3-(cyclohexylmethoxy)-1H-pyrazol-5-yl]phenyl}cyclohexyl)acetate;
Trans tert-butyl 2-methyl-N-[(4-{4-[3-(trifluoromethyl)-1H-pyrazol-5-yl]phenyl}cyclohexyl)acetyl]alaninate;
Trans (4-{4-[2-(formylamino)-1,3-oxazol-4-yl]phenyl}cyclohexyl)acetic acid;
Trans [4-(4-{2-[(2-fluorophenyl)amino]-1,3-thiazol-4-yl}phenyl)cyclohexyl]acetic acid;
Trans ethyl {4-[4-(4-bromo-3-{[(2R)-3-hydroxy-2-methylpropyl]oxy}-1H-pyrazol-5-yl)phenyl]cyclohexyl}acetate;
[4-(4'-hydroxy-1,1'-biphenyl-4-yl)cyclohexyl]acetic acid;
(4-{4'-[({[2-fluoro-5-(trifluoromethyl)phenyl]amino}carbonyl)amino]-1,1'-biphenyl-4-yl}cyclohexyl)acetic acid;
[4-(4-pyrazin-2-ylphenyl)cyclohexyl]acetic acid;
(4-{4-[5-(trifluoromethyl)-1H-1,2,4-triazol-3-yl]phenyl}cyclohexyl)acetic acid;
3-(4-{4-[5-(trifluoromethyl)-1H-pyrazol-3-yl]phenyl}cyclohexyl)propanoic acid;
2-{4-[4-(1H-1,2,4-triazol-3-yl)phenyl]cyclohexyl}propanoic acid;
Trans {4-[4-(7-amino-3-phenylpyrazolo[1,5-a]pyrimidin-6-yl)phenyl]cyclohexyl}acetic acid;
{4-[4-(7-amino-5-methyl[1,2,4]triazolo[1,5-a]pyrimidin-6-yl)phenyl]cyclohexyl}acetic acid;
Trans 4-{4-[7-amino-2-(methylthio)[1,2,4]triazolo[1,5-a]pyrimidin-6-yl]phenyl}cyclohexyl)acetic acid;
Trans {4-[4-(7-amino-2-thien-2-ylpyrazolo[1,5-a]pyrimidin-6-yl)phenyl]cyclohexyl}acetic acid;
Trans {4-[4-(7-amino-2-cyclopropylpyrazolo[1,5-a]pyrimidin-6-yl)phenyl]cyclohexyl}acetic acid;
Trans {4-[4-(7-amino[1,2,4]triazolo[1,5-a]pyrimidin-6-yl)phenyl]cyclohexyl}acetic acid;
Trans ethyl {4-[4-(5-aminoimidazol[1,2-a]pyrimidin-6-yl)phenyl]cyclohexyl}acetate;
Trans (4-{4-[7-amino-2-(4-fluorophenyl)pyrazolo[1,5-a]pyrimidin-6-yl]phenyl}cyclohexyl)acetic acid;
Trans {4-[4-(7-amino-2-methylpyrazolo[1,5-a]pyrimidin-6-yl)phenyl]cyclohexyl}acetic acid;
Trans {4-[4-(7-amino-2-hydroxypyrazolo[1,5-a]pyrimidin-6-yl)phenyl]cyclohexyl}acetic acid;
Trans 2-{4-[4-(7-aminopyrazolo[1,5-a]pyrimidin-6-yl)phenyl]cyclohexyl}-N-methylacetamide;
Trans 2-{4-[4-(7-aminopyrazolo[1,5-a]pyrimidin-6-yl)phenyl]cyclohexyl}acetamide;
Trans {4-[4-(7-aminopyrazolo[1,5-a]pyrimidin-6-yl)phenyl]cyclohexyl}acetic acid;
{4-[5-(5-{[2-(trifluoromethoxy)benzyl]oxy}-1H-pyrazol-3-yl)pyridin-2-yl]cyclohexyl}acetic acid;
Trans {4-[4-(7-amino-5-methylpyrazolo[1,5-a]pyrimidin-6-yl)phenyl]cyclohexyl}acetic acid;
Trans 3-({4-[4-(7-aminopyrazolo[1,5-a]pyrimidin-6-yl)phenyl]cyclohexyl}methyl)-1,2,4-oxadiazol-5(4H)-one; and
Trans 5-({4-[4-(7-aminopyrazolo[1,5-a]pyrimidin-6-yl)phenyl]cyclohexyl}methyl)-1,3,4-oxadiazol-2(3H)-one.

Compounds disclosed herein can contain asymmetrically substituted carbon or sulfur atoms, and accordingly can exist in, and be isolated in, single stereoisomers (e.g., single enantiomer or single diastereomer), mixtures of stereoisomers (e.g., any mixture of enantiomers or diastereomers) or racemic mixtures thereof. Individual optically active forms of the compounds can be prepared for example, by synthesis from optically active starting materials, by chiral synthesis, by enzymatic resolution, by biotransformation, or by chromatographic separation. It is to be understood that the present invention encompasses any racemic, optically active, stereoisomeric form, or mixtures of various proportions thereof, which form possesses properties useful in the inhibition of DGAT-1 activity. Where the stereochemistry of the chiral centers present in the chemical structures illustrated herein is not specified, the chemical structure is intended to encompass compounds containing either stereoisomer of each chiral center present in the compound.

Geometric isomers can exist in the present compounds. The invention contemplates the various geometric isomers and mixtures thereof resulting from the disposal of substituents around a carbon-carbon double bond, a cycloalkyl group, or a heterocycloalkyl group. Substituents around a carbon-carbon double bond are designated as being of Z or E configuration and substituents around a cycloalkyl or heterocycloalkyl are designated as being of cis or trans configuration.

Within the present invention it is to be understood that a compound of Formula (I), (Ia), (Ib), (Ic), (II), (IIa), and (IIb) can exhibit the phenomenon of tautomerism and that the formulae drawings within this specification can represent only one of the possible tautomeric forms. It is to be understood that the invention encompasses any tautomeric form and is not to be limited merely to any one tautomeric form utilized within the naming of the compounds or formulae drawings.

Synthetic Methods

This invention is intended to encompass compounds of the invention when prepared by synthetic processes or by metabolic processes. Preparation of the compounds of the invention by metabolic processes include those occurring in the human or animal body (in vivo) or processes occurring in vitro.

The synthesis of compounds of formula (I), (Ia), (Ib), (Ic), (II), (IIa), or (IIb) wherein the groups $V_a$, $V_b$, $V_c$, Q, A, $R^a$, $R^x$, $R^y$, $R^{za}$, $R^{zb}$, $R^w$, $R^e$, $R^f$, r, s, T, X, $Y^1$, $Y^2$, $Y^3$, and q, have the meanings as set forth in the summary section unless otherwise noted, is exemplified in Schemes 1-9. As used in the descriptions of the schemes and the examples, certain abbreviations are intended to have the following meanings: CDI for carbonyl diimidazole, DMSO for dimethylsulfoxide, Et for ethyl, TBTU for O-benzotriazol-1-yl-N,N,N',N'-tetramethyluronium tetrafluoroborate, MeOH for methanol, and RP-HPLC for preparative reverse phase high-performance liquid chromatography.

Compounds of formula (I) wherein A is an optionally substituted pyrazolyl can be prepared can be prepared using the general procedures as outlined in Scheme 1.

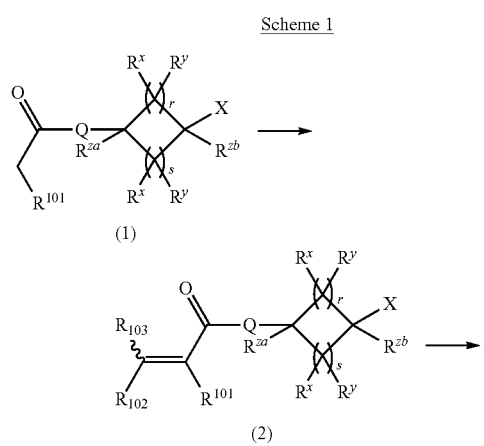

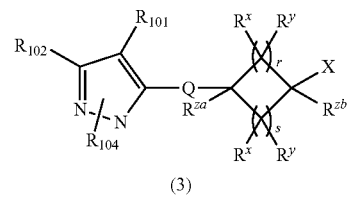

Condensation of (1) wherein $R_{101}$ is hydrogen, halogen or alkyl, with reagents of formula $C(OCH_3)(OCH_3)(N(CH_3)_2)$ ($R_{102}$) wherein $R_{102}$ is hydrogen or alkyl, at elevated temperatures (for example, from about 60° C. to about 110° C.), in a solvent such as, but not limited to, N,N-dimethylformamide, provide intermediates of formula (2) wherein $R_{103}$ is $N(CH_3)_2$.

Alternatively, intermediates of formula (1) wherein $R_{101}$, is $R^a$, can be reacted with an acylating agent of formula $R_{102}C(O)Z$ wherein Z is O-alkyl and $R_{102}$ is alkyl and a base, at a temperature from about room temperature to about 100° C., to provide intermediates of formula (2) wherein $R_{103}$ is OH. The reaction can be conducted in a solvent such as, but not limited to, toluene or methyl tert-butyl ether. Non-limiting examples of bases suitable for the transformation include potassium tert-butoxide and sodium ethoxide.

Intermediates of formula (2) wherein $R_{103}$ is OH or $N(CH_3)_2$ when treated with a hydrazine of formula $NH_2N(H)(R_{104})$ or salts thereof, wherein $R_{104}$ is hydrogen, alkyl or phenyl, in a solvent such as, but not limited to acetic acid and 1,4-dioxane, at a temperature from about 35° C. to about 100° C., provides compounds of formula (3) wherein $R_{104}$ is connected to one of the nitrogen atoms. Non-limiting examples of the hydrazine reagents include hydrazine, methylhydrazine, and phenylhydrazine.

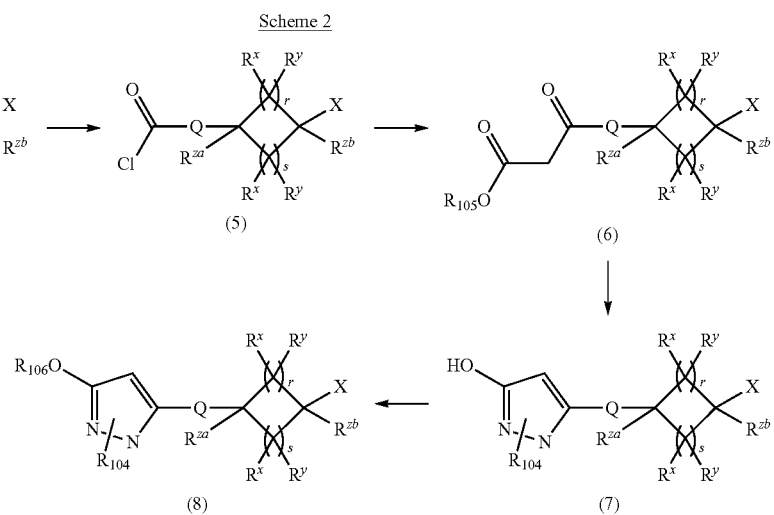

Scheme 2 illustrates the synthesis of compounds of general formula (I) wherein A is optionally substituted pyrazolyl, and one of $R^a$ is —O—$Y^3$, —O—$(CR^eR^f)_q$—$Y^3$, —O—$(CR^eR^f)_q$—$Y^2$—$Y^3$ or —O—$(CR^eR^f)_q$—$Y^2$—$(CR^eR^f)_q$—$Y^3$, and the other as represented by $R_{104}$ is hydrogen, alkyl, or phenyl.

Treatment of compounds of formula (4) with oxalyl chloride in the presence of aluminum chloride and in a solvent such as, but not limited to, dichloromethane at a temperature from about 0° C. to about room temperature provides compounds of formula (5).

Compounds of formula (5) can be converted to compounds of formula (6) wherein $R_{105}$ is alkyl, when treated with an acetate equivalent such as, but not limited to, magnesium ethyl malonate or (trimethylsilyl)ethyl malonate, in the presence of a base, such as, but not limited to 1,8-diazabicyclo [5.4.0]undec-7-ene (DBU), at a temperature from about 0° C. to about room temperature, and in a solvent such as, but not limited to, acetonitrile.

limited to, pyridine, triethylamine, sodium tert-butoxide, cesium carbonate, or sodium hydride. The reaction is generally performed at a temperature from about room temperature to about 180° C. in a solvent such as, but not limited to, toluene or N,N-dimethylformamide.

Compounds of formula (7) can also be reacted with an alkyl alcohol under Mitsonobu reaction conditions by combining the arylphosphine, such as, but not limited to, triphenylphosphine with an azodicarbonyl reagent, such as, but not limited to, diethylazodicarboxylate at a temperature from about 70° C. to about 100° C. to provide compounds of formula (8) wherein $R_{106}$ is alkyl. The reaction can be performed in a solvent such as but not limited to toluene or dichloromethane.

Compounds of general formula (I) wherein A is an optionally substituted oxazolyl or optionally substituted thiazolyl can be prepared using general procedure as outlined in Scheme 3.

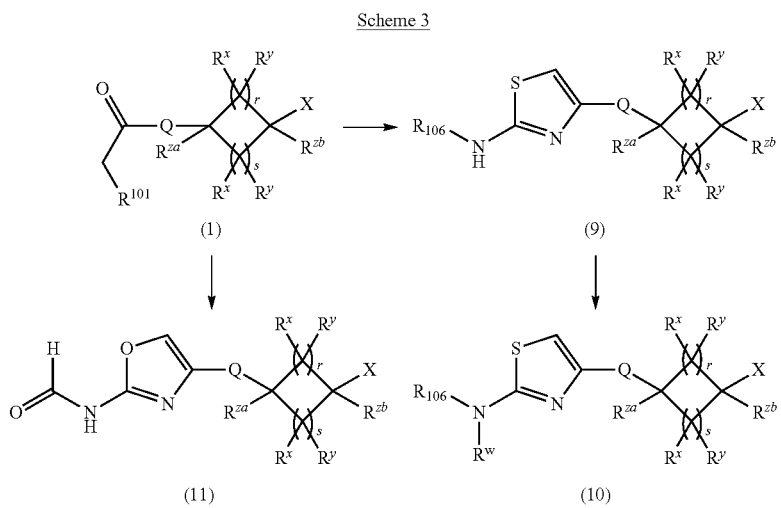

Scheme 3

Compounds of formula (6) can be transformed to compounds of formula (7) wherein $R_{104}$ is connected to one of the nitrogen atoms in the ring, using reaction conditions for the conversion of (2) to (3) as described in Scheme 1.

When treated with an alkylation reagent of formula $R_{106}X^3$ wherein $R_{106}$ is $Y^3$, —$(CR^eR^f)_q$—$Y^3$, —$(CR^eR^f)_q$—$Y^2$—$Y^3$, and $X^3$ is a leaving group such as, but not limited to, halide, trifluoroacetate, methanesulfonate, p-toluenesulfonate or benzene sulfonate, under basic reaction conditions, and optionally in the presence of 18-crown-6, in a solvent such as, but not limited to N,N-dimethylformamide, at a temperature from about room temperature to about 180° C., compounds of formula (7) can be converted to compounds of formula (8). Non-limiting examples of bases include inorganic bases such as potassium or sodium carbonate, cesium carbonate, and potassium or sodium hydride. The reaction can also be conducted in a microwave oven.

Alternatively the transformation of (7) to (8) can also be effected in the presence of a metal catalyst such as, but not limited to, copper metal, CuI, or palladium acetate, optionally in the presence of a ligand such as, but not limited to, 2,2'-bis(diphenylphosphino)-1,1'-binaphthyl or tri-tert-butylphosphine, and optionally in the presence of a base such as, but not As illustrated in Scheme 3, compounds of formula (1) wherein $R_{101}$, is I, Br or Cl, can be condensed with thioureas of formula $R_{106}N(H)C(=S)NH_2$ wherein $R_{106}$ is $Y^3$, —$(CR^eR^f)_q$—$Y^3$, —$(CR^eR^f)_q$—$Y^2$—$Y^3$ or —$(CR^eR^f)_q$—$Y^2$—$(CR^eR^f)_q$—$Y^3$ at a temperature from about 70° C. to 100° C., to provide compounds of formula (9). The reaction can be performed in a solvent such as, but not limited to, ethanol.

Compounds of formula (9) can be alkylated to compounds of formula (10) using many synthetic methods available in the literatures of Organic synthesis. For example, (9) can be converted to (10) in the presence of a suitable base and a reagent of formula $R^wX^3$ wherein $X^3$ is a leaving group such as, but not limited to, halide, trifluoromethanesulfonate, methanesulfonate, p-toluenesulfonate or benzene sulfonate, at ambient or elevated temperature.

Compounds of formula (I) wherein $R_{101}$ is I, Br or Cl, can also react with urea in N,N-dimethylformamide at a temperature from about 35° C. to about 100° C. to provide compounds of formula (11).

Compounds of general formula (I) wherein A is an optionally substituted triazolyl can be prepared using general procedures as shown in Scheme 4.

Scheme 4

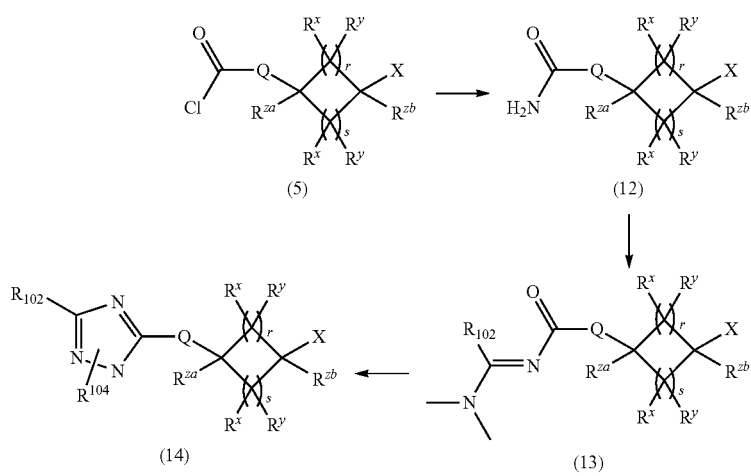

Intermediates of formula (5) can be converted to amides of formula (12) when treated with ammonium hydroxide (or other sources of ammonia such as gaseous ammonia or ammonia in an appropriate solvent) at room temperature. Amides of formula (12) can be condensed with reagents of formula $C(OCH_3)(OCH_3)(N(CH_3)_2)(R_{102})$ wherein $R_{102}$ is hydrogen or alkyl (for example, dimethyl formamide dimethyl acetal or 1,1-dimethoxy-N,N-dimethylethanamine) at elevated temperatures (for example, from about 70° C. to about 100° C.), to provide intermediates of formula (13). The reaction can be performed in a solvent such as but not limited to N,N-dimethylformamide.

When treated with hydrazines of formula $NH_2N(H)(R_{104})$ wherein $R_{104}$ is hydrogen, alkyl or phenyl, intermediates of formula (13) can be converted to (14) using reaction conditions as described in the transformation of (2) to (3) in Scheme 1.

Scheme 5

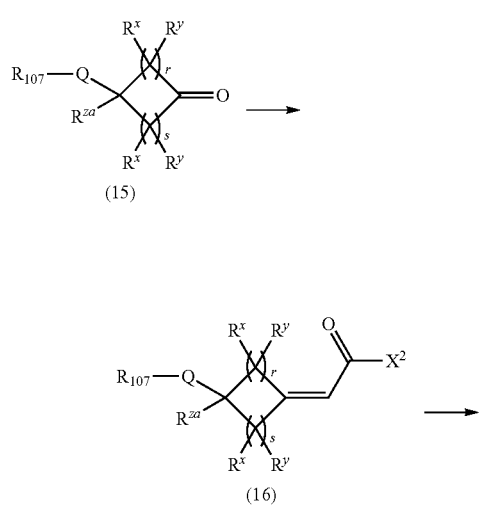

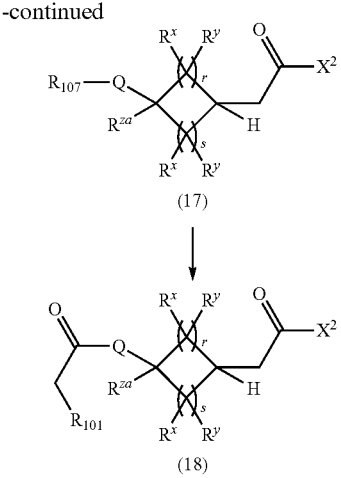

As illustrated in Scheme 5, intermediates of formula (15), wherein $R_{107}$ is hydrogen, halogen, benzyloxy, alkoxy, or an protected hydroxy, can react with a homologating agent in a solvent such as, but not limited to tetrahydrofuran. N,N-dimethylformamide, or dioxane at a temperature from about room temperature to about 75° C. to provide intermediates of formula (16) wherein $X^2$ is —O(alkyl) or —O(arylalkyl). Non-limiting examples of homologating reagents include trimethyl phosphonoacetate and methyldiethyl phosphonoacetate. Intermediates of formula (16) can be hydrogenated with hydrogen gas and at elevated pressure in the presence of catalysts, such as but not limited to palladium on carbon in a solvent such as, but not limited to, ethanol or ethyl acetate to provide compounds of formula (17). The reaction is generally conducted at room temperature or at elevated temperatures.

Intermediates of formula (17) wherein $R_{107}$ is hydrogen can be treated with aluminum chloride and an acylation reagent of formula $R_{101}CH_2C(O)Z$ wherein $R_{101}$, is hydrogen or $R^a$ and Z is halogen, in a solvent such as, but not limited to dichloromethane and at a temperature from about 0° C. to about room temperature, to provide intermediates of formula (18). Non-limiting examples of the acylating reagents include acetyl chloride, butyryl chloride, 2-phenylacetyl chloride and the like.

Intermediates of formula (17) or (18) wherein $X^2$ is —O(alkyl) or —O(arylalkyl) (for example benzyl) can be converted to one wherein $X^2$ is OH by acid or base hydrolysis, or hydrogenation. Such transformation is well known to those that are skilled in the all. One example of base hydrolysis is to utilize lithium or sodium hydroxide.

Transformation of the acids obtained to the corresponding amides can be accomplished by coupling with an appropriate amine. Standard coupling reaction conditions are also known to one skilled in the art. One such conditions is to first convert the acid to an activated ester, for example, by treating the acid with N-hydroxyl succinamide or N-(3-dimethylaminopropyl)-N'-ethylcarbodiimide hydrochloride and a base such as, N-methyl morpholine, in a solvent such as, dichloromethane, and without isolation, followed by treatment of the activated ester with amines of formula wherein $X^2$ is $N(H)(R^w)(R^3)$, $N(H)(R^w)$—$(CR''R^q)_w$—$C(O)OR^{11}$, $N(H)(R^w)$—$(CR'' R^q)_w$—$OR^{11}$, or $N(H)(R^w)$—$(CR''R^q)_w$—$S(O)_2R^{11}$. Such manipulations can also be made after various A groups are introduced.

$N(H)(R^w)$—$(CR''R^q)_w$—$OR^{11}$, or $N(H)(R^w)$—$(CR''R^q)_w$—$S(O)_2R^{11}$, can be prepared using reaction conditions as outlined in Scheme 5.

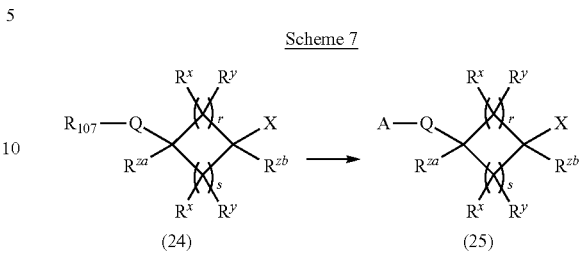

Scheme 7

Intermediates of formula (24) wherein $R_{107}$ is halogen or triflate (prepared from the corresponding alcohol), can be converted to intermediates of formula (24) wherein $R_{107}$ is boronic ester or boronic acid, by reacting with 4,4,4',4',5,5,5',5'-octamethyl-2,2'-bi(1,3,2-dioxaborolane) in the presence

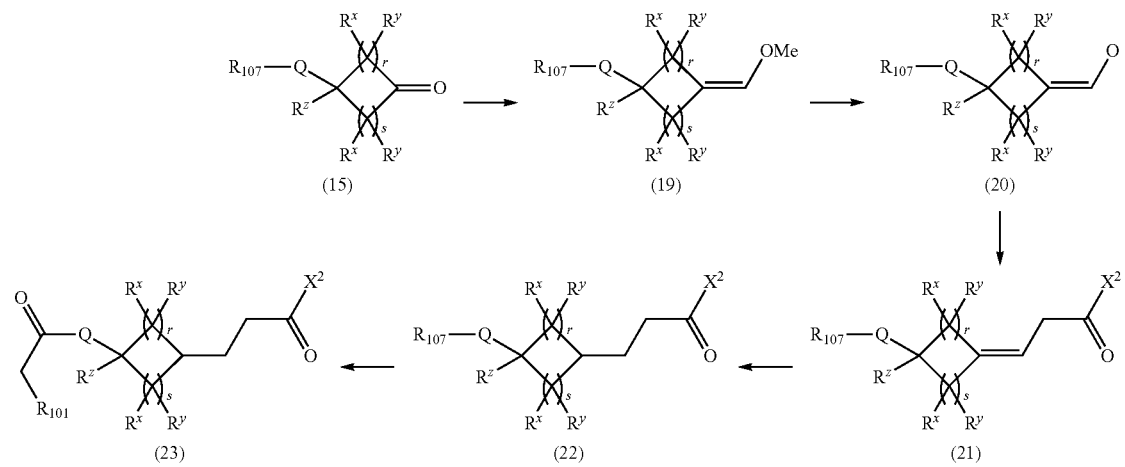

Scheme 6

As shown in Scheme 6, intermediates of formula (15) wherein $R_{107}$ is hydrogen, halogen, benzyloxy, alkoxy, or an protected hydroxy can be reacted with a homologating reagent such as (methoxymethyl)triphenylphosphonium chloride in the presence of a base such as, but not limited to, n-butyllithium, to afford intermediates of formula (19). The reaction is generally conducted in a solvent such as, but not limited to, tetrahydrofuran and at a temperatures ranging from about –78° C. to about 75° C. Intermediates of formula (19) can be treated with aqueous acid such as, but not limited to, hydrochloric acid, to afford intermediates of formula (20) at temperatures ranging from about room temperature to about 90° C. Intermediates of formula (20) wherein $R_{107}$ is hydrogen, halogen, benzyloxy, alkoxy, or an protected hydroxy, can be converted to compounds of formula (22) wherein $X^2$ is —O(alkyl) or —O(arylalkyl) using reaction conditions as described in the transformation of (15) to (17) in Scheme 5.

Compounds of formula (23) wherein $R_{101}$, is hydrogen or $R^a$ can be obtained from (22) wherein $R_{107}$ is hydrogen, using reaction conditions as described in Scheme 5. Acids or amides of compounds of formula (22) or (23) wherein $X^2$ is OH, $N(H)(R^w)(R^3)$, $N(H)(R^w)$—$(CR''R^q)_w$—$C(O)OR^{11}$, of a palladium catalyst and a base. Non-limiting examples of solvents include dioxane and tetrahydrofuran, and non-limiting examples of bases include potassium acetate, potassium carbonate, potassium fluoride and the like. Additional phosphine reagents can be used. These intermediates can then be reacted with reagents of formula A-$R_{108}$ wherein $R_{108}$ is halide, triflate or tosylate using Suzuki reaction conditions to afford compounds of formula (25). It is also appreciated that compounds of formula (25) can be prepared by coupling (24) wherein $R_{107}$ is halogen, triflate or tosylate with A-$R_{108}$ wherein $R_{108}$ is boronic acid or esters (many of which are commercially available or can be prepared from the corresponding triflate or halide as described hereinabove) using Suzuki reaction conditions.

Alternatively, formula (24) wherein $R_{107}$ is halide or triflate can be converted to the stannanes of formula (24) wherein $R_{107}$ is —Sn(alkyl)$_3$, by treating with hexa-alkyl distannanes of formula ((alkyl)$_3$Sn)$_2$ in the presence of a palladium source like tetrakis(triphenylphosphine) palladium(0). Alternatively, stannanes of formula (24) can be obtained from metal-halogen exchange of compounds of formula (24) wherein $R_{107}$ is bromide, with n-butyl lithium at about –78° C., followed by reaction with tributyl tin halide at a temperature from about –78° C. to about room temperature, in a solvent such as tetrahydrofuran. The stannanes of formula (24) wherein $R_{107}$ is —Sn(alkyl)$_3$ can then be treated with A-$R_{108}$ wherein $R_{108}$ is halide, triflate or tosylate in the presence of a palladium source such as tris(dibenzylidineacetone) dipalladium, tetrakis(triphenylphosphine) palladium(0), and optionally in the presence of a ligand such as tri(2-furyl) phosphine or triphenylarsine, to provide compounds of formula (25). It is understood that similar transformation can be effected by reacting compounds of formula (24) wherein $R_{107}$ is halide, triflate or tosylate with A-$R_{108}$ wherein $R_{108}$ is —Sn(alkyl)$_3$ using the aforementioned reaction conditions. Reagents of formula A-$R_{108}$ wherein $R_{108}$ is —Sn(alkyl)$_3$ can be either purchased or prepared from the corresponding halides or triflate using similar conditions as described hereinabove.

O-alkyl and $R_{102}$ is alkyl, and a base, at a temperature from about room temperature to about 100° C., to provide intermediates of formula (28) wherein $R_{103}$ is OH. The reaction can be conducted in a solvent such as, but not limited to, toluene or methyl tert-butyl ether. Non-limiting examples of bases suitable for the transformation include potassium tert-butoxide and sodium ethoxide.

Intermediates of formula (28) wherein $R_{103}$ is OH or $N(CH_3)_2$ when treated with an aminated heterocycle of formula (i) (for example, aminopyrazole, aminotriazole, and aminobenzimidazole), in a solvent such as, but not limited to acetic acid and 1,4-dioxane, at a temperature from about 35° C. to about 100° C. provides compounds of formula (29).

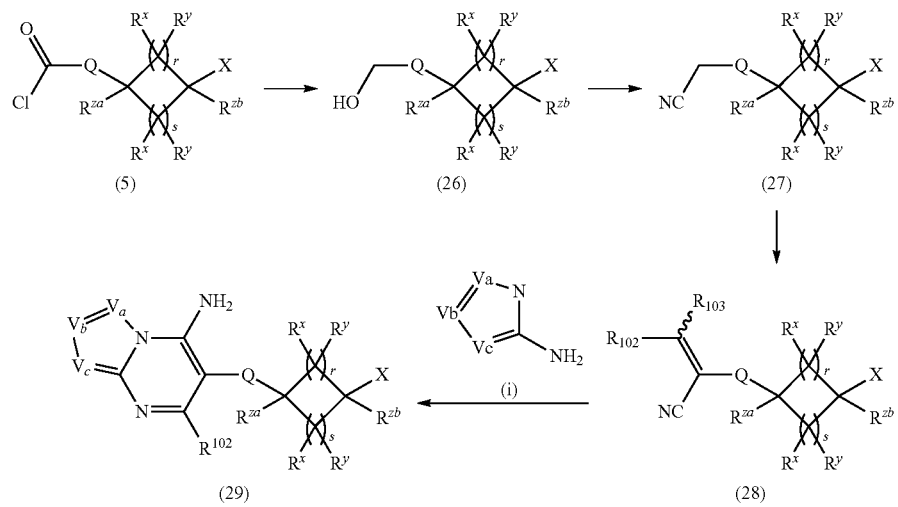

Scheme 8

Scheme 8 illustrates the synthesis of compounds of general formula (I) wherein A is formula (a) and $R^7$ is hydrogen or alkyl.

Compounds of formula (5) can be converted to compounds of formula (26) when treated with a reducing agent such as, but not limited to, sodium borohydride, at room temperature, and in a solvent such as, but not limited to, tetrahydrofuran. Compounds of formula (29) can be treated with an activating reagent such as, but not limited to, methanesulfonyl chloride and phosphorus tribromide under basic reaction conditions, in a solvent such as, but not limited to, dichloromethane, at a temperature from about zero degrees to room temperature. The activated intermediate can be transformed into compounds of formula (27) when treated with a cyanide source such as, but not limited to, tetra-butyl ammonium cyanide, in a solvent such as, but not limited to, N,N-dimethylformamide, at temperatures ranging from about room temperature to about 50° C.

Condensation of (27) with reagents of formula $C(OCH_3)(OCH_3)(N(CH_3)_2)(R_{102})$ wherein $R_{102}$ is hydrogen or alkyl, at elevated temperatures (for example, from about 60° C. to about 110° C.), in a solvent such as, but not limited to, N,N-dimethylformamide, provide intermediates of formula (28) wherein $R_{103}$ is $N(CH_3)_2$.

Alternatively, intermediates of formula (27) can be reacted with an acylating agent of formula $R_{102}C(O)Z$ wherein Z is

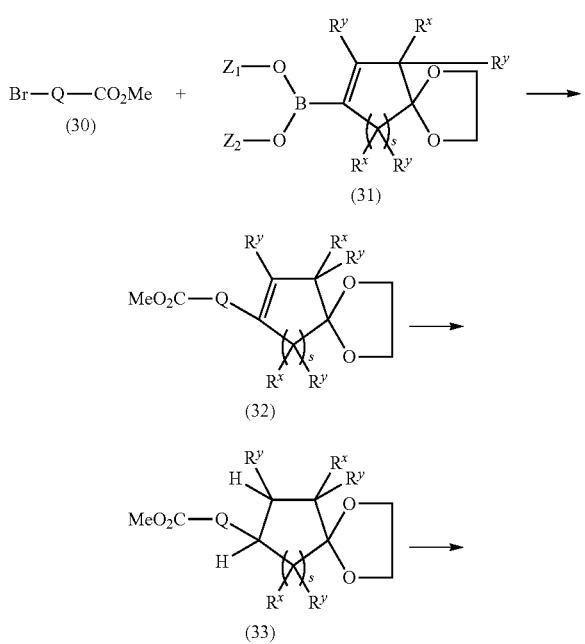

Scheme 9

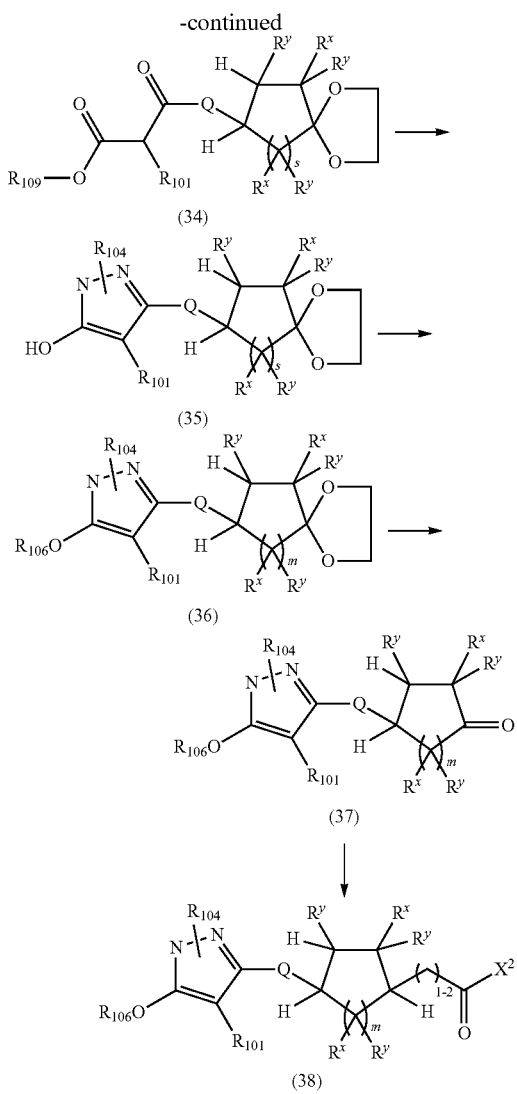

(34)
(35)
(36)
(37)
(38)

Compounds of formula (30) can be reacted with compounds of formula (31) wherein $Z_1$ and $Z_2$ are the both hydrogen or alkyl, or $Z_1$ and $Z_2$ together is —$C(CH_3)_2$—$C(CH_3)_2$ in the presence of a palladium catalyst such as, but not limited to, Pd(II) acetate, and in the presence of a base such as, but not limited to potassium phosphate, and in a mixed solvent system including water and an organic solvent such as, but not limited to, dioxane. The reaction can be performed at elevated temperatures, ranging from about 70 to about 110° C. Intermediates of formula (32) can be hydrogenated with hydrogen gas and at elevated pressure in the presence of catalysts, such as but not limited to palladium on carbon, in a solvent such as, but not limited to, ethanol or ethyl acetate to provide compounds of formula (33). The reaction is generally conducted at room temperature or at elevated temperatures.

Compounds of formula (33) can be transformed to compounds of formula (34) when treated with an ester of formula $R_{109}OC(O)C(R_{101})(H)C(O)O(alkyl)$ wherein $R_{109}$ is alkyl, or aryl, $R_{101}$ is hydrogen, alkyl, aryl, or alkoxy, and a base such as, but not limited to lithium hexamethyl disilylazide, and in a solvent such as, but not limited to, tetrahydrofuran. The reaction is generally performed at about −78° C., and then warned to room temperature.

Compounds of formula (34) can be transformed to compounds of formula (35) wherein $R_{111}$ is connected to one of the nitrogen atoms in the ring, using reaction conditions for the conversion of (2) to (3) as described in Scheme 1.

When treated with an alkylation reagent of formula $R_{106}X^3$ wherein $R^{112}$ is $Y^3$, —$(CR^eR^f)_q$—$Y^3$, —$(CR^eR^f)_q$—$Y^2$—$Y^3$, and $X^3$ is a leaving group such as, but not limited to, halide, trifluoroacetate, methanesulfonate, p-toluenesulfonate or benzene sulfonate, under basic reaction conditions, and optionally in the presence of 18-crown-6, in a solvent such as, but not limited to N,N-dimethylformamide, at a temperature from about room temperature to about 180° C., compounds of formula (35) can be converted to compounds of formula (36). Non-limiting examples of bases include inorganic bases such as potassium or sodium carbonate, cesium carbonate, and potassium or sodium hydride. The reaction can also be conducted in a microwave oven.

Compounds of formula (36) can be transformed to compounds of formula (37) when treated with a lewis acid and a mixed aqueous solvent system including water and a solvent such as, but not limited to, methanol, and at temperatures ranging from about 50 to about 100° C. Alternatively, (36) can be transformed to (37) by stirring in aqueous acid mixtures such as, but not limited to, aqueous HCl, at elevated temperatures.

Using the reaction conditions as discussed in Schemes 5 and 6, compounds of formula (37) can be transformed to compounds of formula (38) wherein $X^2$ is —OH, $N(H)(R^w)$ $(R^3)$, $N(H)(R^w)$—$(CR''R^q)_w$—$C(O)OR^{11}$, $N(H)(R^w)$—$(CR''R^q)_w$, —$OR^{11}$, or $N(H)(R^w)$—$(CR''R^q)_w$—$S(O)_2R^{11}$.

Optimum reaction conditions and reaction times for each individual step can vary depending on the preferable reactants employed and substituents present in the reactants used. Unless otherwise specified, solvents, temperatures and other reaction conditions can be readily selected by one of ordinary skill in the art. Specific procedures are provided in the Synthetic Examples section. Reactions can be worked up in the convention manner, e.g., by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature.

Routine experimentations, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in T. Greene and P. Wuts. Protecting Groups in Chemical Synthesis ($3^{rd}$ ed.), John Wiley & Sons. NY (1999), which is incorporated herein by reference in its entirety. Synthesis of the compounds of the present invention can be accomplished by methods analogous to those described in the synthetic schemes described hereinabove and in specific examples.

Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it can be obtained by carrying out one of the above procedures using a pure geometric isomer as a starting material, or by resolution of a mixture of the geometric isomers of the compound or intermediates using a standard procedure such as chromatographic separation.

It will be appreciated that the synthetic schemes and specific examples as illustrated in the synthetic examples section are illustrative and are not to be read as limiting the scope of the invention as it is defined in the appended claims. All alternatives, modifications, and equivalents of the synthetic methods and specific examples are included within the scope of the claims.

Biological Data

Inhibition of DGAT-1

The identification of the compounds of the invention as DGAT-1 inhibitors was readily achieved using a high throughput screening FlashPlate assay. In this assay, recombinant human DGAT-1 containing an N-terminal $His_6$-epitope tag was produced in the baculovirus expression system. Insect cells (e.g. Sf9 or High Five) were infected for 24 to 72 hours and collected by centrifugation. Cell pellets were resuspended in homogenization buffer [250 mM sucrose, 10 mM Tris-HCl (pH 7.4), 1 mM EDTA] and lysed using a homogenization apparatus, such as a Microfluidizer (single pass, 4° C.). Cell debris was removed by centrifugation at 10.000×g for 30 minutes, and microsomal membranes were collected by ultracentrifugation at 100.000×g for 30 minutes.

DGAT-1 activity was determined as follows. Assay buffer [20 mM HEPES (pH 7.5), 2 mM $MgCl_2$, 0.04% BSA] containing 50 µM of enzyme substrate (didecanoyl glycerol) and 7.5 µM radiolabeled acyl-CoA substrate.[1-$^{14}$C]decanoyl-CoA) was added to each well of a phospholipid FlashPlate (PerkinElmer Life Sciences). A small aliquot of membrane (1 µg/well) was added to start the reaction, which was allowed to proceed for 60 minutes. The reaction was terminated upon the addition of an equal volume (100 µL) of isopropanol. The plates were sealed, incubated overnight and counted the next morning on a TopCount Scintillation Plate Reader (PerkinElmer Life Science). The resultant radiolabeled tridecanoyl glycerol (tricaprin) preferentially binds to the hydrophobic coating on the phospholipid FlashPlate. The proximity of the radiolabeled product to the solid scintillant incorporated into the bottom of the FlashPlate induced fluor release from the scintillant, which was measured in the TopCount Plate Reader. Various concentrations (e.g. 0.0001 µM, 0.001 µM, 0.01 µM, 0.1 µM, 1.0 µM, 10.0 µM) of the representative compounds of the invention were added to individual wells prior to the addition of membranes. The potencies of DGAT-1 inhibition for the compounds of the present invention were determined by calculating the $IC_{50}$ values defined as the inhibitor concentration from the sigmoidal dose response curve at which the enzyme activity was inhibited 50%. Compounds of the present invention were effective in inhibiting DGAT-1 activity and thus are useful as therapeutic agents for treating conditions and diseases that are associated with DGAT-1 activity.

TABLE 1

DGAT-1 Inhibition of representative compounds of the present invention ($IC_{50}$ µM).

| | | | | |
|---|---|---|---|---|
| 0.009 | 0.01 | 0.01822 | 0.04621 | 0.04853 |
| 0.04877 | 0.05837 | 0.0614 | 0.07624 | 0.08328 |
| 0.09187 | 0.11817 | 0.12658 | 0.14811 | 0.19452 |
| 0.2129 | 0.21796 | 0.2227 | 0.23764 | 0.25735 |
| 0.27779 | 0.30743 | 0.41902 | 0.43 | 0.45694 |
| 0.5349 | 0.66221 | 0.70673 | 0.73239 | 0.76144 |
| 0.78474 | 0.80472 | 0.87534 | 0.89934 | 0.92475 |
| 0.96194 | 1.17354 | 1.18377 | 1.27251 | 1.28722 |
| 1.36715 | 1.48264 | 1.6751 | 2.17373 | 2.21226 |
| 2.39756 | 2.51059 | 3.19025 | 4.2726 | 4.53091 |
| 4.66003 | 4.77726 | 5.04715 | 5.07958 | 5.11289 |
| 5.16178 | 5.16214 | 5.35292 | 5.89437 | 5.90296 |
| 6.04016 | 6.12551 | 6.23909 | 6.67693 | 6.76644 |
| 7.34 | 7.73 | 7.79243 | 7.912 | 7.94302 |
| 8.03249 | 8.58021 | 8.95247 | 9.49225 | 9.64461 |
| 9.69462 | 9.76121 | 9.94464 | 4.82 | 0.0569 |
| 0.0706 | 0.515 | 0.353 | 0.524 | 0.0396 |
| 4.210 | 0.0949 | 0.597 | 6.230 | 0.0452 |
| 0.0211 | 0.010 | 0.2110 | 0.0190 | 0.014 |
| 0.0170 | | | | |

Evaluation of Compound Efficacy on the Reduction of Body Weight in Diet-Induced Obese Mice The purpose of this protocol was to determine the effect of chronic administration of a compound on body weight and other metabolic disease parameters in mice made obese by spontaneous ad libitum consumption of a high-fat diet. Diet-induced obesity (DIO) in rodents mimics key aspects of human obesity and metabolic syndrome. DIO mice used in this study have been shown to be hyperinsulinemic and insulin resistant, hyperleptinemia and leptin resistant, and have marked visceral obesity (for review on DIO mice see Collins et al., Physiol. Behav. 81:243-248, 2004).

Individually housed male C57BL/6J mice were given ad lib access to water and to either a low fat diet (D12450B) or a high-fat content diet (D12492 containing 60% kcal from fat, both from Research Diets Inc., New Brunswick, N.J.), for approximately 18 weeks. Mice were sham dosed once daily with the study vehicle for 7 days prior to active dosing to acclimate them to handling and oral gavage. One day prior to active compound dosing, mice were assigned to groups of equal mean body weight and variance. A typical experiment included 80-100 animals, 10 animals per dose including vehicle dosed low-fat and high-fat diet groups. Body weight and food intake were measured by differential weighing.

Representative compounds of the invention were typically dosed at 3, 10, or 30 mg/kg p.o, b.i.d, as a formulation in 1% Tween 80 in water, and the compounds were considered to be active if a statistically significant reduction in body weight was observed for the treated animals after a treatment period of at least seven days, relative to vehicle-treated control animals. In this model, representative compounds produced a statistically significant reduction in body weight after a treatment period of at least seven days, relative to vehicle-treated control animals.

Liver triacylglycerides levels from DIO-mice treated with compounds of the invention typically dosed at 3, 10, or 30 mg/kg p.o, b.i.d, as a formulation in 1% Tween 80 in water for a treatment period of at least seven days were measured from ethanol extracted liver samples using Infinity™ reagents (Thermo Electron Corporation, Louisville, Colo., USA). Representative compounds of the invention produced a statistically significant reduction in liver triacylglycerides in DIO-mice after a treatment period of at least seven days, relative to vehicle-treated control animals.

Plasma triglyceride levels from DIO-mice treated with compounds of the invention typically dosed at 3, 10, or 30 mg/kg p.o, b.i.d, as a formulation in 1% Tween 80 in water for a treatment period of at least seven days were measured. 50 µL of pooled plasma sample from the drug treated animals was loaded onto a Superose 6 PC 3.2/30 column (Amersham Biosciences) and separated into lipoprotein fractions using a SMART FPLC system (Pfizer) running at an elution flow rate of 40 µL/min in a running buffer including 0.15 M NaCl and 0.05 M sodium phosphate pH 7.0. Fractions of 40 µL were collected and triglyceride content was determined using an enzymatic kit assay (Infinity). Representative compounds of the invention produced a statistically significant reduction in the triacylglyceride level of the very low density lipoprotein (VLDL) fraction of the lipoprotein profile in DIO-mice after a treatment period of at least seven days, relative to vehicle-treated control animals.

An insulin tolerance test was also performed at the end of study in DIO mice after a 4 hour fast. Blood glucose levels were monitored via tail snip before and at 30 minute intervals following a single i.p. injection of 0.25 U/kg insulin (Humulin-R, Lilly) using a Precision PCx glucose monitor (Abbott Laboratories, Abbott Park, IL). Representative compounds of the invention produced a statistically significant reduction in blood glucose in animals that had been treated for at least seven days, relative to vehicle-treated control animals.

The effect of co-dosing representative compounds of the invention with rimonabant was also evaluated in DIO-mice. Compounds of the invention were typically dosed at 3, 10, or 30 mg/kg p.o, b.i.d, as a formulation in 1% Tween 80 in water and rimonabant was typically co-administered at a dose of 1 or 3 mg/kg p.o, b.i.d as a formulation in 1% Tween in water. Compounds were considered to be active if they significantly decreased body weight or significantly reduced triglycerides compared to DIO-mice dosed with rimonabant alone. In this model, representative compounds produced a statistically significant reduction in body weight or significantly reduced triglycerides and/or a statistically significant reduction of triglycerides after a treatment period of at least seven days, relative to animals treated with rimonabant alone.

The effect of co-dosing representative compounds of the invention with sibutramine was also evaluated in DIO-mice. Compounds of the invention were typically dosed at 3, 10, or 30 mg/kg p.o, b.i.d, as a formulation in 1% Tween 80 in water and sibutramine was typically co-administered at a dose of 3 or 5 mg/kg p.o, b.i.d, as a formulation in 1% Tween in water. Compounds were considered to be active if they significantly decreased body weight or significantly reduced triglycerides compared to DIO-mice dosed with sibutramine alone. In this model, representative compounds produced a statistically significant reduction in body weight and/or a statistically significant reduction of triglycerides after a treatment period of at least seven days, relative to animals treated with sibutramine alone.

The effect of co-dosing representative compounds of the invention with fenofibrate was also evaluated in DIO-mice. Compounds of the invention were typically dosed at 3, 10, or 30 mg/kg p.o, b.i.d, as a formulation in 1% Tween 80 in water and fenofibrate was typically co-administered at a dose of 100 mg/kg p.o, b.i.d as a formulation in 1% Tween in water. Compounds were considered to be active if they significantly reduced triglycerides compared to DIO-mice dosed with fenofibrate alone. In this model, representative compounds produced a statistically significant reduction in triglycerides after a treatment period of at least seven days, relative to animals treated with fenofibrate alone.

Compounds of the present invention and the pharmaceutically acceptable salts are useful as therapeutic agents. Accordingly, an embodiment of this invention includes a method of treating the various conditions in a subject in need thereof (including mammals) that includes administering to said subject a pharmaceutical composition containing an amount of the compound of the present invention, that is effective in treating the target condition, or a pharmaceutically acceptable salt thereof, together with a pharmaceutically acceptable carrier.

Another aspect of the present invention provides a method of treating or preventing various conditions in a patient (such as a mammal and preferably a human) that are mediated by DGAT-1, which includes administering to said patient a compound of the present invention, or a pharmaceutically acceptable salt, prodrug, salt of a prodrug, or a combination thereof, or a pharmaceutical composition including the same.

Another aspect of the present invention provides methods for the prevention or treatment of obesity and inducing weight loss in an individual which includes administering to said individual a compound of the invention, or its pharmaceutically acceptable salt, prodrug, salt of a prodrug, or a combination thereof. The invention further provides a method for the prevention or treatment of obesity and inducing eight loss in an individual which includes administering to said individual a pharmaceutical composition including a compound of the invention, or its pharmaceutically acceptable salt, prodrug, salt of a prodrug, or a combination thereof, in an amount that is effective in treating obesity or to induce weight loss, and a pharmaceutically acceptable carrier. Yet another aspect of the invention provides a method for preventing weight gain in an individual by administering at least one compound of the invention, or its pharmaceutically acceptable salt, prodrug, salt of a prodrug, or a combination thereof, in an amount that is sufficient to prevent weight gain.

The present invention also relates to the use of the compounds of this invention for the treatment of obesity-related diseases including associated dyslipidemia and other obesity- and overweight-related complications such as, for example, cholesterol gallstones, gallbladder disease, gout, cancer (e.g., colon, rectum, prostate, breast, ovary, endometrium, cervix, gallbladder, and bile duct), menstrual abnormalities, infertility, polycystic ovaries, osteoarthritis, and sleep apnea, as well as for a number of other pharmaceutical uses associated therewith, such as the regulation of appetite and food intake, dyslipidemia, hypertriglyceridemia, metabolic syndrome or Syndrome X, type 2 diabetes (non-insulin-dependent diabetes), atherosclerotic diseases such as heart failure, hyperlipidemia, hypercholesteremia, low HDL levels, hypertension, cardiovascular disease (including atherosclerosis, coronary heart disease, coronary artery disease, and hypertension), cerebrovascular disease such as stroke, and peripheral vessel disease. The compounds of this invention can also be useful for treating physiological disorders related to, for example, regulation of insulin sensitivity, inflammatory response, liver steatosis, elevated liver triacylglycerides, non-alcoholic fatty liver disease, non-alcoholic steatohepatitis, plasma triacylglycerides, HDL, LDL and cholesterol levels and the like. Metabolic syndrome is characterized by a group of metabolic risk factors in one person. Such factors include, but are not limited to, abdominal obesity, atherogenic dyslipidemia (blood fat disorders such as high triglycerides, low HDL cholesterol and high LDL cholesterol), elevated blood pressure, insulin resistance (or glucose intolerance), prothrombotic state (e.g., high fibrinogen or plasminogen activator inhibitor-1 in the blood), and proinflammatory state (e.g., elevated C-reactive protein in the blood). In one embodiment, the present invention provides methods of treating the above listed disorders wherein said methods include the step of administering to a subject in need thereof a compound of the invention, or a pharmaceutically acceptable salt thereof, or a pharmaceutical composition including the same. The compounds of this invention, or pharmaceutical acceptable salts thereof, or pharmaceutical compositions including the same, are also useful in lowering plasma triglycerides level. Thus, in one embodiment, the present invention provides a method for lowering plasma triglycerides in a subject (including mammal) in need thereof, wherein said method includes the step of administering to the subject in need thereof a compound of the invention, or a pharmaceutically acceptable salt thereof, or a pharmaceutical composition including the same.

The term "treatment" or "treating" includes any process, action, application, therapy, or the like, wherein a subject, including human, is provided medical aid with the object of improving the subject's condition, directly or indirectly, or slowing the progression of a condition or disorder in the subject.

Compounds of the invention or pharmaceutically acceptable salts thereof, can be administered alone or in combination (i.e., co-administered) with one or more additional pharmaceutical agents. Combination therapy includes administration of a single pharmaceutical dosage formulation, which contains a compound of the present invention, and one or more additional pharmaceutical agents, as well as administration of the compound of the invention, and each additional pharmaceutical agent, in its own separate pharmaceutical dosage formulation. For example, a compound of the invention, and one or more pharmaceutical agent, can be administered to the patient together, in a single oral dosage composition having a fixed ratio of each active ingredient, such as a tablet or capsule, or each agent can be administered in separate oral dosage formulations.

Where separate dosage formulations are used, compounds of the invention and one or more additional pharmaceutical agents can be administered at essentially the same time (e.g., concurrently) or at separately staggered times (e.g., sequentially).

For example, the compounds of the invention can be used in combination with one of more of the following pharmaceutical agents, including, but are not limited to, anti-obesity drugs including β-3 agonists such as CL-316,243; CB-1 antagonists and/or inverse agonists (for example, rimonabant); neuropeptide Y5 inhibitors; appetite suppressants, such as, for example, sibutramine (Meridia® or Reductil®); MCHrl antagonists and lipase inhibitors, such as, for example, orlistat (Xenical), and a drug compound that modulates digestion and/or metabolism such as drugs that modulate thermogenesis, lipolysis, gut motility, fat absorption, and satiety.

In addition, compounds of the invention can be administered in combination with one or more of the following pharmaceutical agents including PPAR ligands (agonists, antagonists), insulin secretagogues (for example, sulfonylurea drugs and non-sulfonylurea secretagogues). α-glucosidase inhibitors, insulin sensitizers, hepatic glucose output lowering compounds, and insulin and insulin derivatives. Such agents can be administered prior to, concurrently with, or following administration of the compounds of the invention. Insulin and insulin derivatives include both long and short acting forms and formulations of insulin. PPAR ligands can include agonists and/or antagonists of any of the PPAR receptors or combinations thereof. For example, PPAR ligands can include ligands of PPAR-α, PPAR-γ, PPAR-δ or any combination of two or three of the receptors of PPAR. PPAR ligands include, for example, rosiglitazone, troglitazone, and pioglitazone. Sulfonylurea drugs include, for example, glyburide, glimepiride, chlorpropamide, tolbutamide, and glipizide. α-glucosidase inhibitors include acarbose, miglitol, and voglibose. Insulin sensitizers include PPAR-γ agonists such as the glitazones (e.g., troglitazone, pioglitazone, englitazone, MCC-555, rosiglitazone, and the like) and other thiazolidinedione and non-thiazolidinedione compounds; biguanides such as metformin and phenformin; protein tyrosine phosphatase-1B (PP-1B) inhibitors: dipeptidyl peptidase IV (DPP-IV) inhibitors, and 11β-HSD inhibitors. Hepatic glucose output lowering compounds include glucagon antagonists and metformin, such as Glucophage and Glucophage XR. Insulin secretagogues include sulfonylurea and non-sulfonylurea drugs: GLP-1, GIP, PACAP, secretin, and derivatives thereof; nateglinide, meglitinide, repaglinide, glibenclamide, glimepiride, chlorpropamide, glipizide. GLP-1 includes derivatives of GLP-1 with longer half-lives than native GLP-1, such as, for example, fatty-acid derivatized GLP-1 and exendin.

Compounds of the invention can also be used in methods of the invention in combination with one or more pharmaceutical agents including, but are not limited to, HMG-CoA reductase inhibitors, nicotinic acid (for example, Niaspan®), fatty acid lowering compounds (e.g., acipimox); lipid lowering drugs (e.g., stanol esters, sterol glycosides such as tiqueside, and azetidinones such as ezetimibe). ACAT inhibitors (such as avasimibe), bile acid sequestrants, bile acid reuptake inhibitors, microsomal triacylglycerides transport inhibitors, and fibric acid derivatives. HMG-CoA reductase inhibitors include, for example, statin such as lovastatin, simvastatin, pravastatin, fluvastatin, atorvastatin, rivastatin, itavastatin, cerivastatin, and ZD-4522. Fibric acid derivatives include, for example, clofibrate, fenofibrate, bezafibrate, ciprofibrate, beclofibrate, etofibrate, and gemfibrozil. Sequestrants include, for example, cholestyramine, colestipol, and dialkylaminoalkyl derivatives of a cross-linked dextran.

Compounds of the invention can also be used in combination with anti-hypertensive drugs, such as, for example, β-blockers and ACE inhibitors. Examples of additional anti-hypertensive agents for use in combination with the compounds of the present invention include calcium channel blockers (L-type and T-type; e.g., diltiazem, verapamil, nifedipine, amlodipine and mybefradil), diuretics (e.g., chlorothiazide, hydrochlorothiazide, flumethiazide, hydroflumethiazide, bendroflumethiazide, methyl chlorothiazide, trichloromethiazide, polythiazide, benzthiazide, ethacrynic acid tricrynafen, chlorthalidone furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan, neutral endopeptidase (NEP) inhibitors, vasopepsidase inhibitors (dual NEP-ACE inhibitors) (e.g., omapatrilat and gemopatrilat), and nitrates.

The compounds of this invention can be utilized to achieve the desired pharmacological effect by administration to a subject in need thereof in an appropriately formulated pharmaceutical composition. A subject, for example, can be a mammal, including human, in need of treatment for a preferable condition or disease. Therefore the present invention includes pharmaceutical compositions which include a therapeutically effective amount of a compound identified by the methods described herein, or a pharmaceutically acceptable salt thereof, in combination with a pharmaceutically acceptable carrier. The compounds identified by the methods described herein can be administered with a pharmaceutically acceptable carrier using any effective conventional dosage unit forms, for example, immediate and timed release preparations, orally, parenterally, topically, or the like.

The pharmaceutical compositions can be formulated for oral administration in solid or liquid form, for parenteral injection or for rectal administration.

The term "pharmaceutically acceptable carrier" as used herein, means a non-toxic, solid, semi-solid or liquid filler, diluent, encapsulating material, or formulation auxiliary of any type. Examples of therapeutically acceptable excipients include sugars: cellulose and derivatives thereof; oils; glycols; solutions; buffering, coloring, releasing, coating, sweetening, flavoring, and perfuming agents; and the like. These therapeutic compositions can be administered parenterally, intracisternally, orally, rectally, intravenously, or intraperitoneally.

Liquid dosage forms for oral administration of the present compounds include formulations of the same as emulsions, microemulsions, solutions, suspensions, syrups, and elixirs. In addition to the compounds, the liquid dosage forms can contain diluents and/or solubilizing or emulsifying agents. Besides inert diluents, the oral compositions can include wetting, emulsifying, sweetening, flavoring, and perfuming agents.

Injectable preparations of the present compounds include sterile, injectable, aqueous and oleaginous solutions, suspensions or emulsions, any of which can be optionally formulated with parenterally acceptable diluents, dispersing, wetting, or suspending agents. These injectable preparations can be sterilized by filtration through a bacterial-retaining filter or formulated with sterilizing agents that dissolve or disperse in the injectable media.

Inhibition of DGAT-1 by the compounds of the present invention can be delayed by using a liquid suspension of crystalline or amorphous material with poor water solubility. The rate of absorption of the compounds depends upon their rate of dissolution, which, in turn, depends on their crystallinity. Delayed absorption of a parenterally administered compound can be accomplished by dissolving or suspending the compound in oil. Injectable depot forms of the compounds can also be prepared by microencapsulating the same in biodegradable polymers. Depending upon the ratio of compound to polymer and the nature of the polymer employed, the rate of release can be controlled. Depot injectable formulations are also prepared by entrapping the compounds in liposomes or microemulsions that are compatible with body tissues.

Solid dosage forms for oral administration of the present compounds include capsules, tablets, pills, powders, and granules. In such forms, the compound is mixed with at least one inert, therapeutically acceptable excipient such as a carrier, filler, extender, disintegrating agent, solution-retarding agent, wetting agent, absorbent, or lubricant. With capsules, tablets, and pills, the excipient can also contain buffering agents. Suppositories for rectal administration can be prepared by mixing the compounds with an acceptable non-irritating excipient that is solid at ordinary temperature but fluid in the rectum.

The present compounds can be micro-encapsulated with one or more of the excipients discussed previously. The solid dosage forms of tablets, dragees, capsules, pills, and granules can be prepared with coatings and shells such as enteric and release-controlling. In these forms, the compounds can be mixed with at least one inert diluent and can optionally include tableting lubricants and aids. Capsules can also optionally contain opacifying agents that delay release of the compounds in a desired part of the intestinal tract.

Transdermal patches have the added advantage of providing controlled delivery of the present compounds to the body. Such dosage forms are prepared by dissolving or dispensing the compounds in the proper medium. Absorption enhancers can also be used to increase the flux of the compounds across the skin, and the rate of absorption can be controlled by providing a rate controlling membrane or by dispersing the compounds in a polymer matrix or gel.

The compounds of the invention can be used in the form of pharmaceutically acceptable salts, esters, or amides derived from inorganic or organic acids. The term "pharmaceutically acceptable salts, esters and amides," as used herein, include salts, zwitterions, esters and amides of compounds of disclosed herein which are, within the scope of sound medical judgment, acceptable for use in contact with the tissues of humans and lower animals without undue toxicity, irritation, allergic response, and the like, are commensurate with a reasonable benefit/risk ratio, and are effective for their intended use.

Pharmaceutically acceptable salts are well-known in the alt. The salts can be prepared during the final isolation and purification of the compounds or separately by reacting an amino group of the compounds with a suitable acid. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, malate, maleate, methanesulfonate, naphthylenesulfonate, nicotinate, oxalate, pamoate, pectinate, persulfate, 3-phenylpropionate, picrate, oxalate, pivalate, propionate, succinate, tartrate, trichloroacetic, trifluoroacetic, glutamate, para-toluenesulfonate, undecanoate, hydrochloric, hydrobromic, sulfuric, phosphoric, and the like. The amino groups of the compounds can also be quaternized with alkyl chlorides, bromides, and iodides such as methyl, ethyl, propyl, isopropyl, butyl, lauryl, myristyl, stearyl, and the like.

Basic addition salts can be prepared during the final isolation and purification of the present compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts derived from methylamine, dimethylamine, trimethylamine, triethylamine, diethylamine, ethylamine, tributylamine, pyridine, N,N-dimethylaniline, N-methylpiperidine. N-methylmorpholine, dicyclohexyl amine, procaine, dibenzyl amine, N,N-dibenzylphenethylamine, 1-ephenamine, and N,N'-dibenzylethylenediamine, ethylenediamine, ethanolamine, diethanolamine, piperidine, piperazine, and the like, are contemplated as being within the scope of the present invention.

The term "pharmaceutically acceptable ester," as used herein, refers to esters of compounds of the invention which hydrolyze in vivo and include those that break down readily in the human body to leave the parent compound or a salt thereof. Examples of pharmaceutically acceptable, non-toxic esters of the invention include $C_{1-6}$ alkyl esters and $C_{5-7}$ cycloalkyl esters, although $C_{1-4}$ alkyl esters are preferred. Esters of the compounds of the invention can be prepared according to conventional methods. Pharmaceutically acceptable esters can be appended onto hydroxy groups by reaction of the compound that contains the hydroxy group with acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide, alkyl triflate, for example with methyl iodide, benzyl iodide, cyclopentyl iodide. They also can be prepared by reaction of the compound with an acid such as hydrochloric acid and an alkylcarboxylic acid such as acetic acid, or with acid and an arylcarboxylic acid such as benzoic acid.

The term "pharmaceutically acceptable amide," as used herein, refers to non-toxic amides of the invention derived from ammonia, primary $C_{1-6}$ alkyl amines and secondary $C_{1-6}$ dialkyl amines. In the case of secondary amines, the amine can also be in the form of a 5- or 6-membered heterocycle containing one nitrogen atom. Amides derived from ammonia, $C_{1-3}$ alkyl primary amides and $C_{1-2}$ dialkyl secondary amides are preferred. Amides of the compounds of formula (I), (Ia) or (IIa) can be prepared according to conventional methods. Pharmaceutically acceptable amides can be prepared from compounds containing primary or secondary amine groups by reaction of the compound that contains the amino group with an alkyl anhydride, aryl anhydride, acyl halide, or aroyl halide. In the case of compounds containing carboxylic acid groups, the pharmaceutically acceptable esters are prepared from compounds containing the carboxylic acid groups by reaction of the compound with base such as triethylamine, a dehydrating agent such as dicyclohexyl carbodiimide or carbonyl diimidazole, and an alkyl amine, dialkylamine, for example with methylamine, diethylamine, piperidine. They also can be prepared by reaction of the compound with an acid such as sulfuric acid and an alkylcarboxylic acid such as acetic acid, or with acid and an arylcarboxylic acid such as benzoic acid under dehydrating conditions as with molecular sieves added. The composition can contain a compound of the invention in the form of a pharmaceutically acceptable prodrug.

The term "pharmaceutically acceptable prodrug" or "prodrug" as used herein, represents those prodrugs of the compounds of the invention which are, within the scope of sound medical judgment, acceptable for use in contact with the tissues of humans and lower animals without undue toxicity, irritation, allergic response, and the like, commensurate with a reasonable benefit/risk ratio, and effective for their intended use. Prodrugs of the invention can be rapidly transformed in vivo to a parent compound of the invention, for example, by hydrolysis in blood. A thorough discussion is provided in T. Higuchi and V. Stella. Pro-drugs as Novel Delivery Systems. V. 14 of the A.C.S. Symposium Series, and in Edward B. Roche, ed., Bioreversible Carriers in Drug Design. American Pharmaceutical Association and Pergamon Press (1987).

Disorders that can be treated or prevented in a patient by administering to the patient, a therapeutically effective amount of compound of the present invention in such an amount and for such time as is necessary to achieve the desired result. The term "therapeutically effective amount," refers to a sufficient amount of a compound of the invention to effectively ameliorate disorders by inhibiting DGAT-1 at a reasonable benefit/risk ratio applicable to any medical treatment. The specific therapeutically effective dose level for any preferable patient will depend upon a variety of factors including the disorder being treated and the severity of the disorder; the activity of the compound employed; the specific composition employed; the age, body weight, general health, sex, and diet of the patient; the time of administration, route of administration, rate of excretion; the duration of the treatment; and drugs used in combination or coincidental therapy.

The total daily dose of the compounds of the present invention necessary to inhibit the action of DGAT-1 in single or divided doses can be in amounts, for example, from about 0.01 to 50 mg/kg body weight. In a more preferred range, compounds of the present invention inhibit the action of DGAT-1 in a single or divided doses from about 0.05 to 25 mg/kg body weight. Single dose compositions can contain such amounts or submultiple doses thereof of the compounds of the present invention to make up the daily dose. In general, treatment regimens include administration to a patient in need of such treatment from about 1 mg to about 1000 mg of the compounds per day in single or multiple doses.

The compounds identified by the methods described herein can be administered as the sole pharmaceutical agent or in combination with one or more other pharmaceutical agents where the combination causes no unacceptable adverse effects. For example, the compounds of this invention can be combined with anti-obesity, or with known antidiabetic or other indication agents, and the like. Thus, the present invention also includes pharmaceutical compositions which include a therapeutically effective amount of a compound identified by the methods described herein, or a pharmaceutically acceptable salt thereof, a pharmaceutical acceptable carrier, and one of more pharmaceutical agents as disclosed hereinabove.

EXAMPLES

Preparative reverse phase high performance liquid chromatograph (RP-HPLC) were conducted using a Zorbax SB-C18 7 μM 21.2×250 mm column with UV detection analyzed at 220 and 254 nM, and eluted with a solvent system containing component A (water with 0.1% trifluoroacetic acid) and component B ($CH_3CN$ with 0.1% trifluoroacetic acid) with gradient of 5-95% of component B over 30 minutes at 15 mL/min unless otherwise noted.

Example 1

Trans [4-(4-{3-[2-(1-adamantyl)-2-hydroxyethoxy]-1H-pyrazol-5-yl}phenyl)cyclohexyl]acetic acid

Example 1A ethyl 2-(4-phenylcyclohexylidene)acetate

A 250 mL three-neck flask equipped with a stir bar, addition funnel, and mineral oil bubbler was charged with 4-phenylcyclohexanone (6.01 g, 34.5 mmol) and N,N-dimethylformamide (17 mL) and cooled to 0° C. in an ice bath. NaH (1.55 g, 60% dispersion, 38.6 mmol) was then added in portions, and the mixture allowed to stir for 30 min. After this time triethylphosphonoacetate (7.8 mL, 38.7 mmol) in 6 mL N,N-dimethylformamide was added dropwise. After stirring for 40 min, the reaction mixture was dumped into 5% $NaHSO_4$ and extracted with dichloromethane (×3). The organic layers were combined, dried over $Na_2SO_4$, filtered, and the solvents evaporated in vacuo. The residue was then taken up in 8:1 hexanes/ethyl acetate and purified via column chromatography using the same solvent system to afford 7.2 grams of the title compound in 85% yield. $^1$H NMR (300 MHz, $CDCl_3$) δ ppm 1.28 (t, 3 H), 1.55-1.75 (m, 2 H), 2.00-2.15 (m, 3 H), 2.24-2.48 (m, 2 H), 2.67-2.88 (m, 1 H), 3.88-4.03 (m, 1 H), 4.17 (q, J=7.12 Hz, 2 H), 5.68 (s, 1 H), 7.17-7.24 (m, 3 H), 7.27-7.34 (m, 2 H); MS (ESI) m/z 245 [M+H]$^+$.

Example 1B

Trans ethyl 2-(4-phenylcyclohexyl)acetate

The product of Example 1A (6.00 g, 24.7 mmol) was dissolved in 60 mL of ethanol and 10% Pd/C was added (600 mg). The reaction mixture was placed in a Par shaker at 60 psi for 2 h. After this time, the catalyst was filtered, and the solvents evaporated to afford the title compound. $^1$H NMR (300 MHz, CDCl$_3$) δ ppm 1.05-1.22 (m, 2 H), 1.22-1.30 (m, 3 H), 1.43-1.59 (m, 2 H), 1.64-1.75 (m, 2 H), 1.86-1.96 (m, 3 H), 2.24 (d, J=6.44 Hz, 2 H), 2.40-2.49 (m, 1 H), 4.15 (q, J=7.35 Hz, 2 H), 7.17-7.23 (m, 3 H), 7.24-7.33 (m, 2 H); MS (ESI) m/z 247 [M+H]$^+$.

Example 1C

Trans ethyl 2-(4-(4-(chlorocarbonyl)phenyl)cyclohexyl)acetate

To a solution containing the product of example 1B (2.46 g, 10.0 mmol) and AlCl$_3$ (2.66 g, 20.0 mmol) in 30 mL of dichloromethane at 0° C. was added oxalyl chloride (5 mL, 2 M solution in dichloromethane, 10 mmol). The mixture was stirred at room temperature for 30 minutes. After this time the reaction mixture was poured into an ice-cold solution containing calcium chloride (3 g) in 100 mL of water. The reaction mixture was stirred for 2 h and was extracted with dichloromethane (2×100 mL). The combined organic layer was washed with brine, and dried over anhydrous sodium sulfate. After filtration, the solvent was removed under reduced pressure, and the resulting oil was purified by flash chromatography (ethyl acetate/hexane, 1/8) to afford the title compound as a colorless oil. $^1$H NMR (500 MHz, DMSO-d$_6$) δ ppm 1.15 (m, 2H), 1.19 (t, J=7.06 Hz, 3H), 1.47 (m, 2H), 1.57-1.85 (m, 5H), 2.22 (d, J=6.75 Hz, 2H), 2.47 (m, 1H), 4.07 (q, J=7.06 Hz, 2H), 7.35 (d, J=8.29 Hz, 2H), 7.85 (d, J=8.29 Hz, 2H).

Example 1D

Trans ethyl 3-(4-((1s,4s)-4-(2-ethoxy-2-oxoethyl)cyclohexyl)phenyl)-3-oxopropanoate To a solution of 3-ethoxy-3-oxopropanoic acid (264 mg, 2.00 mmol) in 10 mL of tetrahydrofuran at 0° C. was added magnesium ethoxide (456 mg, 4.00 mmol). The mixture was stirred at room temperature overnight under N$_2$. The solvent was then removed by rotary evaporation, and the resulting white powder was dried in vacuo for 2 hours and then poured into 20 mL of tetrahydrofuran. To the resulting suspension at 0° C. was added the product of Example 1C (310 mg, 1.00 mmol) in 5 mL tetrahydrofuran. The mixture was stirred at room temperature for 2 hours. Water (50 mL) was added to the reaction mixture, which was then extracted with ethyl acetate (2×100 mL). The combined organic layers were washed with brine, dried over Na$_2$SO$_4$ and concentrated. The residue was purified on a flash column, eluting with 0-5% ethyl acetate in hexanes, to provide the title compound. $^1$H NMR (500 MHz, DMSO-d$_6$) δ ppm 1.06-1.22 (m, 8H), 1.48 (m, 2H), 1.57-1.86 (m, 5H), 2.22 (d, J=6.75 Hz, 2H), 2.56 (m, 1H), 4.02-4.15 (m, 6H), 7.40 (d, J=8.29 Hz, 2H), 7.87 (d, J=8.29 Hz, 2H); MS (ESI) m/z 361.1 [M+H]$^+$.

Example 1E

Trans ethyl 2-((1s,4s)-4-(4-(5-hydroxy-1H-pyrazol-3-yl)phenyl)cyclohexyl)acetate A mixture of the product of Example 1D (70 mg, 0.20 mmol), acetic acid (0.1 mL), and hydrazine (35% in water, 0.2 mL) in 1,4-dioxane (5 mL) was heated at 90-95° C. for 2 hours. The reaction mixture was concentrated and the residue triturated in ethyl acetate. The title product was collected by filtration as a white precipitate and rinsed with ethyl acetate. $^1$H NMR (500 MHz, DMSO-d$_6$) δ ppm 1.14 (m, 2H), 1.18 (t, J=7.06 Hz, 3H), 1.47 (m, 2H), 1.53-1.87 (m, 5H), 2.21 (d, J=6.75 Hz, 2H), 2.47 (m, 1H), 4.06 (q, J=7.06 Hz, 2H), 5.79 (s, 1H), 7.24 (d, J=8.28 Hz, 2H), 7.54 (d, J=8.28 Hz, 2H); MS (ESI) m/z 329.1 [M+H]$^+$.

Example 1F

Trans ethyl [4-(4-{3-[2-(1-adamantyl)-2-oxoethoxy]-1H-pyrazol-5-yl}phenyl)cyclohexyl]acetate A mixture of the product of Example 1E (33 mg, 0.10 mmol), 1-Adamantyl bromomethyl ketone (26 mg, 0.1 mmol), and potassium carbonate (14 mg, 0.10 mmol) in N,N-dimethylformamide was heated at 75° C. under N$_2$ for 6 hours. The reaction mixture was filtered through celite, washed with ethyl acetate, concentrated, and purified on a flash column (eluting with 15% ethyl acetate in hexanes) to provide the title compound. $^1$H NMR (500 MHz, DMSO-d$_6$) δ ppm 1.14 (m, 2H), 1.19 (t, J=7.02 Hz, 3H), 1.48 (m, 2H), 1.66-1.89 (m, 17H), 2.00 (m, 3H), 2.22 (d, J=6.71 Hz, 2H), 2.47 (m, 1H), 4.06 (q, J=6.71 Hz, 2H), 5.06 (s, 2H), 6.06 (s, 1H), 7.28 (d, J=8.24 Hz, 2H), 7.57 (d, J=8.24 Hz, 2H), 12.12 (br s, 1H); MS (ESI) m/z 505.3 [M+H]$^+$.

Example 1G

Trans ethyl [4-(4-{3-[2-(1-adamantyl)-2-hydroxyethoxy]-1H-pyrazol-5-yl}phenyl)cyclohexyl]acetate Sodium borohydride (38 mg, 0.1 mmol) was added to a solution of the product from Example 1F (25 mg, 0.05 mmol) in tetrahydrofuran (3 mL) and ethanol (3 mL) maintained at 0° C. The reaction was allowed to warm to room temperature over 30 min and then stirred at room temperature for 1 hour. After this time the reaction was quenched by addition of water (5 mL) and extracted with ethyl acetate. The organic extracts were combined and washed with water, brine, dried (MgSO$_4$), filtered and concentrated to a brown oil which was purified via flash column (eluting with 15% ethyl acetate in hexanes) to provide the title compound. $^1$H NMR (500 MHz, DMSO-d$_6$) δ ppm 1.12 (m, 2H), 1.19 (t, J=7.32 Hz, 3H), 1.42-1.99 (m, 22H), 2.22 (d, J=6.71 Hz, 2H), 2.47 (m, 1H), 3.89 (dd, J$_1$=10.38 Hz, J$_2$=7.94 Hz, 1H), 4.02 (m, 1H), 4.06 (q, J=7.32 Hz, 2H), 4.24 (dd, J$_1$=10.37 Hz, J$_2$=2.74 Hz, 1H), 4.71 (s, 1H), 6.07 (s, 1H), 7.28 (d, J=8.24 Hz, 2H), 7.59 (d, J=8.24 Hz, 2H), 12.21 (br s 1H); MS (ESI) m/z 507.4 [M+H]$^+$.

Example 1H

Trans [4-(4-{3-[2-(1-adamantyl)-2-hydroxyethoxy]-1H-pyrazol-5-yl}phenyl)cyclohexyl]acetic acid A scintillation vial was charged with the product from Example 1G (18 mg, 0.036 mmol), lithium hydroxide monohydrate (5 mg, 0.12 mmol) and a mixed solvent (2 mL of tetrahydrofuran, 1 mL of H$_2$O). The reaction vessel was placed in a shaker at room temperature overnight. After this time the mixture was acidified with 10% HCl, concentrated, and purified via RP-HPLC (Preparative reversed-phase high pressure liquid chromatography) using a Zorbax SB-C18 7 μM 21.2×250 mm column with UV detection analyzed at 220 and 254 nM (preparative method: water with 0.1% trifluoroacetic acid and CH$_3$CN with 0.1% trifluoroacetic acid gradient 5-95% CH$_3$CN over 30 minutes at 15 mL/min.) to provide the title product. $^1$H NMR (500 MHz, DMSO-d$_6$) δ ppm 1.12 (m, 2H), 1.42-1.86 (m, 19H), 1.94 (m, 3H), 2.14 (d, J=7.01 Hz, 2H), 2.47 (m, 1H), 3.89 (dd, J$_1$=10.38 Hz, J$_2$=7.94 Hz, 1H), 4.24 (dd, J$_1$=10.68 Hz, J$_2$=2.74 Hz, 1H), 4.70 (d, J=5.49 Hz, 2H), 6.07 (s, 1H), 7.28 (d, J=8.24 Hz, 2H), 7.59 (d, J=8.24 Hz, 2H), 12.13 (br s, 2H); MS (ESI) m/z 479.3 [M+H]$^+$.

Example 2

Trans [4-(4-{3-[2-(1-adamantyl)-2-oxoethoxy]-1H-pyrazol-5-yl}phenyl)cyclohexyl]acetic acid The title compound was prepared using the procedure described in Example 1H, substituting the product from Example 1E for the product from Example 1G. $^1$H NMR (500 MHz, DMSO-d$_6$) δ ppm 1.12 (m, 2H), 1.44-1.88 (m, 19H), 2.00 (m, 3H), 2.14 (d, J=7.02 Hz, 2H), 2.47 (m, 1H), 5.06 (s, 2H), 6.06 (s, 1H), 7.28 (d, J=8.24 Hz, 2H), 7.57 (d, J=8.24 Hz, 2H), 12.02 (br s, 1H), 12.21 (br s, 1H); MS (ESI) m/z 477.3 [M+H]$^+$.

Example 3

Trans [4-(4-{3-[2-(4-methoxyphenyl)-2-oxoethoxy]-1H-pyrazol-5-yl}phenyl)cyclohexyl]acetic acid A mixture of the product from Example 1E (33 mg, 0.10 mmol), 2-bromo-1-(4-methoxyphenyl)ethanone (26 mg, 0.1 mmol), and potassium carbonate (14 mg, 0.10 mmol) in N,N-dimethylformamide was heated at 75° C. under N$_2$ for 6 hours. The reaction mixture was cooled, filtered through celite, washed with ethyl acetate and concentrated. The residue was purified on flash column, eluting with 15% ethyl acetate in hexanes. The isolated product was hydrolyzed according to the procedure as described in Example 1H to provide the title compound. $^1$H NMR (500 MHz, DMSO-d$_6$) δ ppm 1.13 (m, 2H), 1.43-1.87 (m, 7H), 2.15 (d, J=7.01 Hz, 2H), 2.47 (m, 1H), 3.86 (s, 3H), 5.46 (s, 2H), 6.13 (s, 1H), 7.08 (d, J=9.16 Hz, 2H), 7.28 (d, J=8.24 Hz, 2H), 7.57 (d, J=8.24 Hz, 2H), 7.98 (d, J=9.16 Hz, 2H), 12.25 (br s, 2H); MS (ESI) m/z 449.2 [M+H]$^+$.

Example 4

Trans {4-[4-(3-{[2-(trifluoromethoxy)benzyl]oxy}-1H-pyrazol-5-yl)phenyl]cyclohexyl}acetic acid The title compound was prepared according to the procedure as described in Example 3 by substituting 1-(bromomethyl)-2-(trifluoromethoxy)benzene for 2-bromo-1-(4-methoxyphenyl)ethanone. $^1$H NMR (500 MHz, DMSO-d$_6$) δ ppm 1.14 (m, 2H), 1.47 (m, 2H), 1.68-1.87 (m, 5H), 2.14 (d, J=7.06 Hz, 2H), 2.47 (m, 1H), 5.25 (s, 2H), 6.14 (s, 1H), 7.29 (d, J=8.29 Hz, 2H), 7.38-7.53 (m, 3H), 7.58 (d, J=8.24 Hz, 2H), 7.66 (dd, J$_1$=7.37 Hz, J$_2$=1.85 Hz, 1H), 12.32 (br s, 1H); MS (ESI) m/z 475.2 [M+H]$^-$.

Example 5

Trans {4-[4-(3-{[5-(trifluoromethyl)-2-furyl]methoxy}-4-{[5-(trifluoromethyl)-2-furyl]methyl}-1H-pyrazol-5-yl)phenyl]cyclohexyl}acetic acid The title compound was prepared according to the procedure as described in Example 3, substituting 2-(bromomethyl)-5-(trifluoromethyl)furan for 2-bromo-1-(4-methoxyphenyl)ethanone. $^1$H NMR (500 MHz, DMSO-d$_6$) δ ppm 1.14 (m, 2H), 1.47 (m, 2H), 1.68-1.87 (m, 5H), 2.14 (d, J=7.06 Hz, 2H), 2.47 (m, 1H), 3.83 (s, 2H), 5.25 (s, 2H), 6.08 (m, 1H), 6.71 (m, 1H), 6.98 (m, 1H), 7.19 (m, 1H), 7.32 (d, J=8.29 Hz, 2H), 7.40 (d, J=8.29 Hz, 2H), 11.98 (br s, 1H), 12.26 (br s, 1H); MS (ESI) m/z 597.3 [M+H]$^+$.

Example 6

Trans {4-[4-(4-[2-(trifluoromethoxy)benzyl]-3-{[2-(trifluoromethoxy)benzyl]oxy}-1H-pyrazol-5-yl) phenyl]cyclohexyl}acetic acid The title compound was prepared according to the procedure as described in Example 3, substituting 1-(bromomethyl)-2-(trifluoromethoxy)benzene for 2-bromo-1-(4-methoxyphenyl)ethanone. $^1$H NMR (500 MHz, DMSO-d$_6$) δ ppm 1.11 (m, 2H), 1.47 (m, 2H), 1.66-1.87 (m, 5H), 2.13 (d, 2H, J=6.76 Hz), 2.47 (m, 1H), 3.83 (s, 2H), 5.27 (s, 2H), 7.05-7.48 (m, 12H), 12.21 (br s, 1H); MS (ESI) m/z 649.4 [M+H]$^+$.

Example 7

Trans (4-{4-[3-(cyclohexylmethoxy)-1H-pyrazol-5-yl]phenyl}cyclohexyl)acetic acid The title product was prepared from the product from Example 72 using the procedure as described in Example 1H. $^1$H NMR (500 MHz, DMSO-d$_6$) δ ppm 0.98-1.85 (m, 20H), 2.14 (d, J=7.02 Hz, 2H), 2.47 (m, 1H), 3.88 (m, 2H), 6.15 (s, 1H), 7.29 (d. J=8.24 Hz, 2H), 7.59 (d, J=8.24 Hz, 2H), 12.11 (br s, 2H); MS (ESI) m/z 397.2 [M+H]$^+$.

Example 8

Trans {4-[4-(3-{[3-(trifluoromethoxy)benzyl]oxy}-1H-pyrazol-5-yl)phenyl]cyclohexyl}acetic acid The title compound was prepared according to the procedure as described in Example 3, substituting 1-(bromomethyl)-3-(trifluoromethoxy)benzene for 2-bromo-1-(4-methoxyphenyl)ethanone. $^1$H NMR (500 MHz, DMSO-d$_6$) δ ppm 1.13 (m, 2H), 1.42-1.85 (m, 7H), 2.14 (d, J=7.02 Hz, 2H), 2.47 (m, 1H), 5.24 (s, 2H), 6.16 (s, 1H), 7.29 (d, J=8.24 Hz, 2H), 7.30-7.34 (m, 1H), 7.43-7.55 (m, 3H), 7.58 (d, J=8.24 Hz, 2H), 12.00 (br s, 1H), 12.34 (br s, 1H); MS (ESI) m/z 475.2 [M+H]$^+$.

Example 9

Trans {4-[4-(3-{[5-(trifluoromethyl)-2-furyl]methoxy}-1H-pyrazol-5-yl)phenyl]cyclohexyl}acetic acid The title product was prepared from the product of Example 57 using the procedure as described in Example 1H. $^1$H NMR (500 MHz, DMSO-d$_6$) δ ppm 1.13 (m, 2H), 1.40-1.87 (m, 7H), 2.14 (d, J=6.75 Hz, 2H), 2.47 (m, 1H), 5.21 (s, 2H), 6.15 (s, 1H), 6.79 (d, J=3.68 Hz, 1H), 7.22 (m, 1H), 7.29 (d, J=8.28 Hz, 2H), 7.59 (d, J=8.28 Hz, 2H), 12.40 (br s, 1H); MS (ESI) m/z 449.2 [M+H]$^+$.

Example 10

Trans (4-{4-[3-(3-phenoxypropoxy)-1H-pyrazol-5-yl]phenyl}cyclohexyl)acetic acid

The title compound was prepared according to the procedure as described in Example 3, substituting (3-bromopropoxy)benzene for 2-bromo-1-(4-methoxyphenyl)ethanone. $^1$H NMR (500 MHz, DMSO-d$_6$) δ ppm 1.13 (m, 2H), 1.43-1.87 (m, 7H), 2.15 (m, 4H), 2.47 (m, 1H), 4.11 (t, J=6.44 Hz, 2H), 4.25 (t, J=6.44 Hz, 2H), 6.08 (s, 1H), 6.90-6.97 (m, 3H), 7.26-7.31 (m, 4H), 7.59 (d, J=8.28 Hz, 2H), 12.40 (br s, 1H); MS (ESI) m/z 435.2 [M+H]$^+$.

Example 11

Trans (4-{4-[3-(4-phenoxybutoxy)-1H-pyrazol-5-yl]phenyl}cyclohexyl)acetic acid

The title compound was prepared according to the procedure as described in Example 3, substituting (4-bromobutoxy)benzene for 2-bromo-1-(4-methoxyphenyl)ethanone. $^1$H NMR (500 MHz, DMSO-d$_6$) δ ppm 1.13 (m, 2H), 1.47 (m, 2H), 1.68-1.90 (m, 9H), 2.15 (d, J=7.02 Hz, 2H), 2.47 (m, 1H), 4.02 (m, 2H), 4.14 (m, 2H), 6.08 (s, 1H), 6.92 (m, 3H), 7.27 (m, 4H), 7.57 (d, J=8.24 Hz, 2H), 12.26 (br s, 1H); MS (ESI) m/z 449.2 [M+H]$^+$.

Example 12

Trans (4-{4-[3-(2,3-dihydro-1,4-benzodioxin-2-ylmethoxy)-1H-pyrazol-5-yl]phenyl}cyclohexyl)acetic acid The title compound was prepared from the product of Example 62 using the procedure as described in Example 1H. $^1$H NMR (500 MHz, DMSO-d$_6$) δ ppm 1.14 (m, 2H), 1.47 (m, 2H), 1.67-1.88 (m, 5H), 2.14 (d, J=7.06 Hz, 2H), 2.47 (m, 1H), 4.12 (dd, J$_1$=11.66 Hz, J$_2$=7.06 Hz, 1H), 4.34 (m, 2H), 4.41 (dd, J$_1$=11.66 Hz, J$_2$=2.45 Hz, 1H), 4.57 (m, 1H), 6.14 (s, 1H), 6.82-6.94 (m, 4H), 7.29 (d, J=8.28 Hz, 2H), 7.59 (d, J=8.28 Hz, 2H), 12.3 (br s, 2H); MS (ESI) m/z 449.2 [M+H]$^+$.

Example 13

Trans {4-[4-(3-{[2-(difluoromethoxy)benzyl]oxy}-1H-pyrazol-5-yl)phenyl]cyclohexyl}acetic acid The title compound was prepared according to the procedure as described in Example 3, substituting 1-(bromomethyl)-2-(difluoromethoxy)benzene for 2-bromo-1-(4-methoxyphenyl)ethanone. $^1$H NMR (500 MHz, DMSO-d$_6$) δ ppm 1.13 (m, 2H), 1.48 (m, 2H), 1.57-1.86 (m, 5H), 2.14 (d, J=7.02 Hz, 2H), 2.47 (m, 1H), 5.21 (s, 2H), 6.14 (s, 1H), 7.22-7.31 (m, 5H), 7.39-7.45 (m, 1H), 7.56-7.61 (m, 3H), 12.25 (br s, 2H); MS (ESI) m/z 457.2 [M+H]$^+$.

Example 14

Trans (4-{4-[3-(cyclopentylmethoxy)-1H-pyrazol-5-yl]phenyl}cyclohexyl)acetic acid The title compound was prepared from the product of Example 56 using the procedure as described in Example 1H. $^1$H NMR (500 MHz, DMSO-d$_6$) δ ppm 1.13 (m, 2H), 1.31 (m, 2H), 1.44-1.83 (m, 13H), 2.14 (d, J=7.02 Hz, 2H), 2.29 (m, 1H), 2.47 (m, 1H), 3.97 (d, J=7.02 Hz, 2H), 6.07 (s, 1H), 7.29 (d, J=8.24 Hz, 2H), 7.68 (d, J=8.24 Hz, 2H), 12.11 (br s, 2H); MS (ESI) m/z 383.2 [M+H]$^+$.

Example 15

Trans (4-{4-[3-(cyclobutylmethoxy)-1H-pyrazol-5-yl]phenyl}cyclohexyl)acetic acid The title compound was prepared according to the procedure as described in Example 3, substituting (bromomethyl) cyclobutane for 2-bromo-1-(4-methoxyphenyl)ethanone. $^1$H NMR (500 MHz, DMSO-d$_6$) δ ppm 1.13 (m, 2H), 1.48 (m, 2H), 1.68-1.95 (m, 10H), 2.05 (m, 1H), 2.14 (d, J=6.67 Hz, 2H), 2.47 (m, 1H), 2.70 (m, 1H), 4.05 (d, J=6.75 Hz, 2H), 6.06 (s, 1H), 7.28 (d, J=8.29 Hz, 2H), 7.58 (d, J=8.29 Hz, 2H), 12.25 (br s, 1H); MS (ESI) m/z 369.1 [M+H]$^+$.

Example 16

Trans (4-{4-[3-(cyclohexyloxy)-1H-pyrazol-5-yl]phenyl}cyclohexyl)acetic acid

The title compound was prepared from the product of Example 47 using the procedure as described in Example 1H. $^1$H NMR (500 MHz, DMSO-d$_6$) δ ppm 1.13 (m, 2H), 1.2-1.56 (m, 9H), 1.67-1.86 (m, 7H), 1.97 (m, 1H), 2.14 (d, J=7.02 Hz, 2H), 2.47 (m, 1H), 4.39 (m, 1H), 6.06 (s, 1H), 7.28 (d, J=8.24 Hz, 2H), 7.58 (d, J=8.24 Hz, 2H), 12.20 (br s, 1H); MS (ESI) m/z 383.2 [M+H]$^+$.

Example 17

Trans (4-{4-[3-(tetrahydro-2H-pyran-2-ylmethoxy)-1H-pyrazol-5-yl]phenyl}cyclohexyl)acetic acid The title compound was prepared according to the procedure as described in Example 3 by substituting 2-(bromomethyl)tetrahydro-2H-pyran for 2-bromo-1-(4-methoxyphenyl)ethanone. $^1$H NMR (500 MHz, DMSO-d$_6$) δ ppm 1.13 (m, 2H), 1.30 (m, 1H), 1.42-1.86 (m, 12H), 2.05 (m, 1H), 2.14 (d, J=6.67 Hz, 2H), 2.47 (m, 1H), 3.61 (m, 1H), 3.88 (m, 1H), 4.00 (d, J=5.49 Hz, 2H), 6.07 (s, 1H), 7.28 (d, J=8.24 Hz, 2H), 7.58 (d, J=8.24 Hz, 2H), 12.21 (br s, 2H); MS (ESI) m/z 399.2 [M+H]$^+$.

Example 18

Trans ethyl [4-(4-{3-[2-(1-adamantyl)-2-oxoethoxy]-1H-pyrazol-5-yl}phenyl)cyclohexyl]acetate The title compound was prepared according to the procedure as described in Example 1F. $^1$H NMR (500 MHz, DMSO-d$_6$) δ ppm 1.14 (m, 2H), 1.19 (t, J=7.02 Hz, 3H), 1.48 (m, 2H), 1.66-1.89 (m, 17H), 2.00 (m, 3H), 2.22 (d, J=6.71 Hz, 2H), 2.47 (m, 1H), 4.06 (q, J=6.71 Hz, 2H), 5.06 (s, 2H), 6.06 (s, 1H), 7.28 (d, J=8.24 Hz, 2H), 7.57 (d, J=8.24 Hz, 2H), 12.12 (br s, 1H); MS (ESI) m/z 505.3 [M+H]$^+$.

Example 19

Trans (4-{4-[5-(cyclobutylmethoxy)-1-(cyclobutylmethyl)-1H-pyrazol-3-yl]phenyl}cyclohexyl)acetic acid The title compound was prepared according to the procedure as described in Example 3 by substituting (bromomethyl)cyclobutane for 2-bromo-1-(4-methoxyphenyl)ethanone. $^1$H NMR (500 MHz, DMSO-d$_6$) δ ppm 1.13 (m, 2H), 1.47 (m, 2H), 1.66-2.12 (m, 17H), 2.22 (d, J=7.02 Hz, 2H), 2.45 (m, 1H), 2.72 (m, 2H), 3.92 (d, J=6.72 Hz, 2H), 4.08 (d, J=6.72 Hz, 2H), 6.09 (s, 1H), 7.21 (d, J=8.24 Hz, 2H), 7.62 (d, J=8.24 Hz, 2H), 11.77 (br s, 1H); MS (ESI) m/z 437.3 [M+H]$^+$.

Example 20

Trans (4-{4-[3-(benzyloxy)-1H-pyrazol-5-yl]phenyl}cyclohexyl)acetic acid

The title compound was prepared according to the procedure as described in Example 3 by substituting benzyl bromide for 2-bromo-1-(4-methoxyphenyl)ethanone. $^1$H NMR (500 MHz, DMSO-$d_6$) δ ppm 1.13 (m, 2H), 1.48 (m, 2H), 1.65-1.87 (m, 5H), 2.14 (d, J=7.06 Hz, 2H), 2.47 (m, 1H), 5.17 (s, 2H), 6.13 (s, 1H), 7.28 (d, J=8.29 Hz, 2H), 7.31-7.47 (m, 5H), 7.60 (d, J=8.29 Hz, 2H), 12.22 (br s, 1H); MS (ESI) m/z 391.2 [M+H]$^+$.

Example 21

Trans (4-{4-[3-(cyclopentyloxy)-1H-pyrazol-5-yl] phenyl}cyclohexyl)acetic acid

The title compound was prepared from the product of Example 61 using the procedure as described in Example 1H. $^1$H NMR (500 MHz, DMSO-$d_6$) δ ppm 1.13 (m, 2H), 1.48 (m, 2H), 1.53-1.91 (m, 13H), 2.14 (d, J=7.01 Hz, 2H), 2.47 (m, 1H), 4.89 (m, 1H), 6.04 (s, 1H), 7.28 (d, J=8.24 Hz, 2H), 7.58 (d, J=8.24 Hz, 2H), 12.12 (br s, 2H); MS (ESI) m/z 369.2 [M+H]$^+$.

Example 22

Trans {4-[4-(3-{[4-(trifluoromethyl)benzyl]oxy}-1H-pyrazol-5-yl)phenyl]cyclohexyl}acetic acid The title compound was prepared according to the procedure as described in Example 3 by substituting 1-(bromomethyl)-4-(trifluoromethyl)benzene for 2-bromo-1-(4-methoxyphenyl)ethanone. $^1$H NMR (500 MHz, DMSO-$d_6$) δ ppm 1.13 (m, 2H), 1.48 (m, 2H), 1.65-1.87 (m, 5H), 2.14 (d, J=7.01 Hz, 2H), 2.47 (m, 1H), 5.29 (s, 2H), 6.16 (s, 1H), 7.29 (d, J=8.24 Hz, 2H), 7.58 (d, J=8.24 Hz, 2H), 7.66 (d, J=8.24 Hz, 2H), 7.75 (d, J=8.24 Hz, 2H), 12.03 (br s, 1H), 12.33 (br s, 1H); MS (ESI) m/z 459.2 [M+H]$^+$.

Example 23

Trans [4-(4-{3-[(5-methylisoxazol-3-yl)methoxy]-1H-pyrazol-5-yl}phenyl)cyclohexyl]acetic acid The title compound was prepared according to the procedure as described in Example 3 by substituting 4-(bromomethyl)-5-methylisoxazole for 2-bromo-1-(4-methoxyphenyl) ethanone. $^1$H NMR (500 MHz, DMSO-$d_6$) δ ppm 1.13 (m, 2H), 1.48 (m, 2H), 1.65-1.87 (m, 5H), 2.14 (d, J=6.75 Hz, 2H), 2.40 (s, 3H), 2.47 (m, 1H), 5.19 (s, 2H), 6.14 (s, 1H), 6.31 (s, 1H), 7.29 (d, J=8.24 Hz, 2H), 7.59 (d, J=8.24 Hz, 2H), 12.02 (br s, 1H), 12.36 (br s, 1H); MS (ESI) m/z 396.2 [M+H]$^+$.

Example 24

Trans {4-[4-(1H-1,2,4-triazol-5-yl)phenyl] cyclohexyl}acetic acid

Example 24A

Trans ethyl 2-(4-(4-carbamoylphenyl)cyclohexyl)acetate

Ammonium hydroxide (large excess) was added to the product from Example 1C (8.43 g, 27.3 mmol) at room temperature. White solids precipitated out and were collected by filtration and washed with water to afford the title compound (7.9 g, 100%) as a white solid which was taken on to the next step without further purification. MS (DCI) m/z 290.1 [M+H]$^+$.

Example 24B

Trans {4-[4-(1H-1,2,4-triazol-5-yl)phenyl] cyclohexyl}acetic acid

Step A:
The product of Example 24A (250 mg, crude) was combined with an excess of N,N-dimethylformamide dimethyl acetal and was heated at 110° C. for 1.5 h. After cooling to room temperature, the volatiles were removed by rotary evaporation and the residue placed under high vacuum for 1 h to give the title compound as a brown oil (200 mg). This material was taken on to the next step without further purification.
Step B:
The product from Step A (200 mg, approx. 0.60 mmol) was combined with glacial acetic acid (2.9 ml) in a pressure tube and hydrazine hydrate (34 μL, 0.70 mmol) was added. The tube was capped and the reaction was heated to 70° C. for 1.5 h. The volatiles were removed by rotary evaporation and the residue was passed through a plug of silica gel, and then was dissolved in ethanol at room temperature. Aqueous NaOH (1N) was added and the solution became cloudy. The reaction was heated at 60° C. for 1.5 h upon which time the solution became clear. The volatiles were removed by rotary evaporation and the aqueous portion was transferred to a separatory funnel. The basic solution was washed with diethyl ether and the aqueous layer was acidified using 1 N HCl. White solids precipitated and the aqueous layer was extracted with ethyl acetate (3×15 mL). The combined organics were dried (Na$_2$SO$_4$), filtered and concentrated by rotary evaporation to give a white solid. The solids were triturated with ethyl acetate/hexanes and filtered to provide the title compound as a white solid. $^1$H NMR (300 MHz, methanol-$d_4$) δ ppm 1.11-1.30 (m, 2 H), 1.49-1.66 (m, 2 H), 1.70-1.99 (m, 5 H), 2.23 (d, J=6.78 Hz, 1 H), 2.43-2.64 (m, 1 H), 7.36 (d, J=8.14 Hz, 2 H), 7.90 (d, J=8.14 Hz, 2 H), 8.31 (s, 1 H); MS (ESI) m/z 286 [M+H]$^+$.

Example 25

Trans [4-(4-{5-[(5-methylisoxazol-3-yl)methoxy]-1-[(5-methylisoxazol-3-yl)methyl]-1H-pyrazol-3-yl}phenyl)cyclohexyl]acetic acid The title compound was prepared according to the procedure as described in Example 3 by substituting 3-(bromomethyl)-5-methylisoxazole for 2-bromo-1-(4-methoxyphenyl) ethanone. $^1$H NMR (500 MHz, DMSO-$d_6$) δ ppm 1.13 (m, 2H), 1.48 (m, 2H), 1.65-1.87 (m, 5H), 2.14 (d, J=6.75 Hz, 2H), 2.31 (m, 3H), 2.40 (s, 3H), 2.47 (m, 1H), 5.19 (s, 2H), 5.26 (s, 2H), 5.95 (s, 1H), 6.27 (s, 1H), 6.31 (s, 1H), 7.32 (d, J=8.24 Hz, 2H), 7.45 (d, J=8.24 Hz, 2H), 12.20 (br s, 1H); MS (ESI) m/z 491.32 [M+H]$^+$.

Example 26

Trans N-methyl-N-[(4-{4-[5-(trifluoromethyl)-1H-pyrazol-3-yl]phenyl}cyclohexyl)acetyl]glycine Example 26A Trans ethyl 2-(4-(4-acetylphenyl)cyclohexyl)acetate A 500 mL round bottom flask with a stir bar was charged with the product of Example 1B (3 g, 12.2 mmol) and 60 mL of dichloromethane. The reaction solution was cooled to 0° C.

and AlCl₃ (4.86 g, 36.5 mmol) was added in portions. The mixture was allowed to stir for 20 min, and then acetyl chloride (954 μL, 13.4 mmol) was added dropwise. After stirring for 15 minutes, the reaction mixture was slowly pored into a beaker with ice water and diluted with 120 mL of ethyl acetate. The layers were separated and the organic layer washed with 1 N NaHCO₃ (×2) brine (×2), dried over Na₂SO₄, and filtered. Evaporation of the solvents afforded the title compound. ¹H NMR (300 MHz, DMSO-d₆) δ ppm 1.04-1.17 (m, 2 H), 1.18 (t, 3 H), 1.39-1.62 (m, 3 H), 1.68-1.88 (m, 5 H), 2.17-2.26 (m, 2 H), 2.52-2.57 (s, 3 H), 4.07 (q, J=7.12 Hz, 2 H), 7.25-7.46 (m, 2 H), 7.77-7.94 (m, 2 H) MS (ESI) m/z 247 [M+H]⁺.

Example 26B

Trans ethyl (4-{4-[5-(trifluoromethyl)-1H-pyrazol-3-yl]phenyl}cyclohexyl)acetate A 50 mL flask was charged with 6.6 ml methyl tert-butyl ether and ethyl trifluoroacetate (520 uL, 3.47 mmol). To this solution was then added 533 μL of sodium ethoxide (21% in ethanol) slowly, followed by the product of Example 26A (1.00 g, 3.47 mmol) in 3 mL of methyl tert-butyl ether over 5 minutes. After stirring overnight, the solution was quenched with sat NH₄Cl and extracted with ethyl acetate (×2). The ethyl acetate layers were then evaporated to dryness, and the residue taken up in ethanol (5 mL). Two equivalents of hydrazine hydrate (35% in water) were added, and the solution heated to 70° C. overnight. After this time, the solution was cooled to room temperature and the solvent evaporated in vacuo. The residue was taken up in 1:1 methanol/DMSO and purified over RP-HPLC to afford the title product. ¹H NMR (300 MHz, DMSO-D6) δ ppm 1.03-1.15 (m, 1 H), 1.19 (t, J=7.12 Hz, 3 H), 1.37-1.60 (m, 2 H), 1.69-1.86 (m, 5 H), 2.15-2.27 (m, 2 H), 4.07 (q, J=7.12 Hz, 2 H), 6.96-7.22 (m, 1 H), 7.26-7.43 (m, 2 H), 7.63-7.80 (m, 2 H), 13.98 (s, 1 H); MS (ESI) m/z 381 [M+H]⁺.

Example 26C

Trans (4-{4-[5-(trifluoromethyl)-1H-pyrazol-3-yl]phenyl}cyclohexyl)acetic acid

A round bottom flask was charged with the product from Example 26B (0.520 g, 1.36 mmol) and 6 mL of 20% aqueous tetrahydrofuran. Lithium hydroxide was added (114 mg, 2.72 mmol), and the reaction stirred at room temperature overnight. After 16 hours, the reaction was quenched with 1 N HCl, and the mixture filtered over a bed of celite. Evaporation of the solvents and purification via silica gel chromatography (10-30% ethyl acetate/hexanes with 1% acetic acid) afforded the title compound. ¹H NMR (400 MHz, DMSO-d₆) δ ppm 1.04-1.23 (m, 2 H), 1.41-1.57 (m, 2 H), 1.58-1.67 (m, 1 H), 1.69-1.77 (m, 1 H), 1.78-1.88 (m, 4 H), 2.12-2.20 (m, 2 H), 7.05-7.17 (m, 1 H), 7.26-7.41 (m, 2 H), 7.62-7.82 (m, 2 H), 12.00 (s, 1 H), 13.89-14.07 (m, 1 H); MS (ESI) m/z 354 [M+H]⁺.

Example 26D

Trans methyl N-methyl-N-[(4-{4-[3-(trifluoromethyl)-1H-pyrazol-5-yl]phenyl}cyclohexyl)acetyl]glycinate To a 20 mL scintillation vial was added the product from Example 26C (30 mg, 0.085 mmol), methyl 2-(methylamino) acetate (10.0 mg, 0.097 mmol), and N,N-dimethylformamide (0.85 mL) followed by O-(7-azabenzotriazol-1-yl)-N,N,N'N'-tetramethyluronium hexafluorophosphate (39.0 mg, 0.102 mmol) and diisopropylethylamine (30.0 μL, 0.176 mmol). Following 4 hours of stirring at room temperature, the solvent was evaporated and the residue purified over RP-HPLC to afford the title product. The NMR spectrum includes a mixture of rotamers, with the major rotamer being reported. ¹H NMR (500 (MHz, DMSO-d₆) δ ppm 0.98-1.20 (m, 2 H), 1.38-1.55 (m, 2 H), 1.70-1.93 (m, 5 H), 2.20-2.33 (m, 2 H), 2.78-2.88 (m, 1 H), 3.01-3.10 (m, 3 H), 3.64 (s, 3 H), 4.08 (s, 2 H), 7.03-7.19 (m, 1 H), 7.28-7.41 (m, 2 H), 7.66-7.76 (m, 2 H), 13.80-14.09 (m, 1 H); MS (ESI) m/z 438 [M+H]⁺.

Example 26E

Trans N-methyl-N-[(4-{4-[5-(trifluoromethyl)-1H-pyrazol-3-yl]phenyl}cyclohexyl)acetyl]glycine A 20 mL scintillation vial was charged with the product from Example 26D (12 mg, 0.027 mmol). 80% tetrahydrofuran in water, and lithium hydroxide (2.00 mg, 0.048 mmol) and shaken for 6 hours. After this time the reaction mixture was acidified with 1N HCl, filtered, and evaporated to dryness to afford the title product. The NMR spectrum includes a mixture of rotamers, with the major rotamer being reported. ¹H NMR (500 MHz, DMSO-d₆) δ ppm 1.02-1.20 (m, 2H), 1.41-1.55 (m, 2 H), 1.74-1.91 (m, 5 H), 2.22-2.31 (m, 2 H), 2.78-2.80 (m, 1 H), 2.96-3.10 (m, 3 H), 3.98 (s, 2 H), 7.05-7.19 (m, 1 H), 7.27-7.45 (m, 2 H), 7.60-7.85 (m, 2 H), 13.98 (s, 1 H); MS (ESI) m/z 424[M+H]⁺.

Example 27

Trans (4-{4-[3-(cyclobutyloxy)-1H-pyrazol-5-yl]phenyl}cyclohexyl)acetic acid

A mixture of the product from Example 1E (40 mg, 0.12 mmol), cyclobutanol (15 mg, 0.15 mmol). 1,1'-(azodicarbonyl) dipiperidine (ADDP) (30 mg, 0.12 mmol) and tributylphosphine (20 mg, 0.1 mmol) in toluene (2 mL) was heated at 90° C. under N₂ for 6 hours. The mixture was concentrated and purified on a RP-HPLC. The isolated product was hydrolyzed according to the procedure as described in Example 1H to provide the title compound. ¹H NMR (500 MHz, DMSO-d₆) δ ppm 1.12 (m, 2H), 1.48 (m, 2H), 1.53-1.86 (m, 7H), 2.03 (m, 2H), 2.14 (d, J=7.01 Hz, 2H), 2.36 (m, 2H), 2.47 (m, 1H), 4.75 (m, 1H), 6.02 (s, 1H), 7.28 (d, J=8.24 Hz, 2H), 7.58 (d, J=8.24 Hz, 2H), 12.19 (br s, 2H); MS (ESI) m/z 355.1 [M+H]⁺.

Example 28

Trans (4-{4-[5-(trifluoromethyl)-1H-pyrazol-3-yl]phenyl}cyclohexyl)acetic acid

The title compound was prepared according to the procedure as described in Example 26C. ¹H NMR (400 MHz, DMSO-d₆) δ ppm 1.04-1.23 (m, 2 H), 1.41-1.57 (m, 2 H), 1.58-1.67 (m, 1 H), 1.69-1.77 (m, 1 H), 1.78-1.88 (m, 4 H), 2.12-2.20 (m, 2 H), 7.05-7.17 (m, 1 H), 7.26-7.41 (m, 2 H), 7.62-7.82 (m, 2 H), 12.00 (s, 1 H), 13.89-14.07 (m, 1 H); MS (ESI) m/z 354 [M+H]⁺.

Example 29

Trans (4-{4-[3-(cyclopropylmethoxy)-1H-pyrazol-5-yl]phenyl}cyclohexyl)acetic acid The title compound was prepared according to the procedure as described in Example 3 by substituting (bromomethyl)cyclopropane for 2-bromo-1-(4-methoxyphenyl)ethanone. $^1$H NMR (500 MHz, DMSO-$d_6$) δ ppm 0.31 (m, 2H), 0.55 (m, 2H), 1.13 (m, 2H), 1.23 (m, 1H), 1.48 (m, 2H), 1.56-1.86 (m, 5H), 2.14 (d, J=7.02 Hz, 2H), 2.47 (m, 1H), 3.90 (d, J=7.02 Hz, 2H), 6.06 (s, 1H), 7.28 (d, J=8.24 Hz, 2H), 7.58 (d, J=8.24 Hz, 2H), 12.20 (br s, 1H); MS (ESI) m/z 355.1 [M+H]$^+$.

Example 30

Trans 2-(4-{4-[3-(cyclohexylmethoxy)-1H-pyrazol-5-yl]phenyl}cyclohexyl)-N-hydroxyacetamide A scintillation vial was charged with the product from Example 72 (16 mg, 0.038 mmol), sodium hydroxide (40 mg, 0.10 mmol), hydroxylamine (33 mg, 0.1 mmol) and 4 mL of methanol. The vial was placed on a shaker at room temperature overnight. The mixture was acidified with 10% HCl, concentrated, and purified on a RP-HPLC to provide the title compound. $^1$H NMR (500 MHz, DMSO-$d_6$) δ ppm 0.97-1.84 (m, 20H), 1.88 (d, J=6.71 Hz, 2H), 2.47 (m, 1H), 3.88 (m, 2H), 6.06 (s, 1H), 7.29 (d, J=8.24 Hz, 2H), 7.59 (d, J=8.24 Hz, 2H), 8.67 (br s, 1H), 10.35 (s, 1H), 12.21 (br s, 1H); MS (ESI) m/z 412.2 [M+H]$^+$.

Example 31

Trans (4-{4-[3-(pyridin-2-ylmethoxy)-1H-pyrazol-5-yl]phenyl}cyclohexyl)acetic acid The title compound was prepared from the product from Example 67 using the procedure as described in Example 1H. $^1$H NMR (500 MHz, DMSO-$d_6$) δ ppm 1.13 (m, 2H), 1.48 (m, 2H), 1.65-1.87 (m, 5H), 2.14 (d, J=6.75 Hz, 2H), 2.47 (m, 1H), 5.29 (s, 2H), 6.17 (s, 1H), 7.28 (d, J=8.29 Hz, 2H), 7.41 (m, 1H), 7.58 (m, 1H), 7.60 (d, J=8.29 Hz, 2H), 7.92 (m, 1H), 8.60 (m, 1H), 12.20 (br s, 1H); MS (ESI) m/z 392.1 [M+H]$^+$.

Example 32

Trans (4-{4-[3-(tetrahydrofuran-2-ylmethoxy)-1H-pyrazol-5-yl]phenyl}cyclohexyl)acetic acid The title compound was prepared from the product of Example 68 using the procedure as described in Example 1H. $^1$H NMR (500 MHz, DMSO-$d_6$) δ ppm 1.13 (m, 2H), 1.48 (m, 2H), 1.61-1.91 (m, 8H), 1.98 (m, 1H), 2.14 (d, J=6.75 Hz, 2H), 2.47 (m, 1H), 3.66 (m, 1H), 3.78 (m, 1H), 4.04 (m, 2H), 4.14 (m, 1H), 6.08 (s, 1H), 7.28 (d, J=8.24 Hz, 2H), 7.60 (d, J=8.24 Hz, 2H), 12.21 (br s, 2H); MS (ESI) m/z 385.2 [M+H]$^+$.

Example 33

Trans (4-{4-[4-bromo-3-(cyclobutylmethoxy)-1H-pyrazol-5-yl]phenyl}cyclohexyl)acetic acid Step A:
A mixture of the product of Example 1E (65 mg, 0.20 mmol), bromomethyl cyclobutane (30 mg, 0.20 mmol) and potassium carbonate (28 mg, 0.20 mmol) in N,N-dimethylformamide was heated at 75° C. under $N_2$ for 6 hours. The reaction mixture was then acidified with 4N HCl, filtered through celite, and concentrated.

Step B:
The product from step A was hydrolysed using the procedure as described in Example 1H to provide the title product. $^1$H NMR (500 MHz, DMSO-$d_6$) δ ppm 1.14 (m, 2H), 1.50 (m, 2H), 1.68-1.95 (m, 10H), 2.07 (m, 1H), 2.15 (d, J=6.75 Hz, 2H), 2.47 (m, 1H), 2.73 (m, 1H), 4.16 (d, J=6.75 Hz, 2H), 7.35 (d, J=8.28 Hz, 2H), 7.62 (d, J=8.28 Hz, 2H), 12.56 (br s, 1H), 12.56 (br s, 1H); MS (ESI) m/z 447.0 [M+H]$^+$.

Example 34

Trans N-hydroxy-2-(4-{4-[3-(trifluoromethyl)-1H-pyrazol-5-yl]phenyl}cyclohexyl)acetamide A scintillation vial was charged with the product from Example 28 (38 mg, 0.1 mmol), sodium hydroxide (40 mg, 0.1 mmol), hydroxylamine hydrochloride (33 mg, 0.1 mmol) and 4 mL of methanol. The reaction vial was placed in a shaker at room temperature overnight. After this time, the mixture was acidified with 10% HCl, concentrated, and purified on a RP-HPLC to provide the title compound. $^1$H NMR (500 MHz, DMSO-$d_6$) δ ppm 1.10 (m, 2H), 1.48 (m, 2H), 1.67-1.85 (m, 5H), 1.88 (d, J=6.75 Hz, 2H), 2.47 (m, 1H), 7.12 (s, 1H), 7.34 (d, J=8.28 Hz, 2H), 7.72 (d, J=8.24 Hz, 2H), 8.63 (br s, 1H), 10.34 (s, 1H), 13.96 (br s, 1H); MS (ESI) m/z 366.1 [M−H]$^+$.

Example 35

Trans N-(methylsulfonyl)-2-(4-{4-[3-(trifluoromethyl)-1H-pyrazol-5-yl]phenyl}cyclohexyl)acetamide To a 20 ml scintillation vial was added the product from Example 26C (30 mg, 0.085 mmol), methanesulfonamide (9.00 mg, 0.088 mmol), and N,N-dimethylformamide (0.85 mL) followed by O-(7-azabenzotriazol-1-yl)-N,N,N',N'-tetramethyluronium hexafluorophosphate (39.0 mg, 0.102 mmol) and diisopropylethylamine (30 μL, 0.176 mmol). Following 4 hours of stirring, the solvent was evaporated and the residue purified over RP-HPLC to afford the title compound. $^1$H NMR (500 MHz, DMSO-$d_6$) δ ppm 1.06-1.20 (m, 2 H), 1.43-1.57 (m, 2 H), 1.74-1.91 (m, 5 H), 2.17-2.26 (m, 2 H), 2.41-2.46 (m, 1 H), 6.95-7.22 (m, 1 H), 7.23-7.44 (m, 2 H), 7.64-7.82 (m, 2 H), 11.68 (s, 1 H), 13.98 (s, 1 H); MS (ESI) m/z 430 [M+H]$^+$.

Example 36

Trans 1-({4-[4-(1H-pyrazol-3-yl)phenyl]cyclohexyl}acetyl)-L-proline

Lithium hydroxide monohydrate (0.022 g, 0.5 mmol) was added to a stirred solution of the product from Example 63 (0.065 g, 0.16 mmol) in tetrahydrofuran (5 mL) and water (2 mL) at room temperature. The reaction was stirred at room temperature for 12 h and then quenched by addition of 1N HCl. It was then extracted with ethyl acetate (3×25 mL), the organic extracts washed with water, brine, dried (MgSO$_4$), concentrated and purified by RP-HPLC to afford the titled compound as a white solid. $^1$H NMR (400 MHz, DMSO-$d_6$) δ ppm 1.05-1.18 (m, 2 H), 1.40-1.51 (m, 2H), 1.70-1.95 (m, 8 H), 2.11-2.27 (m, 3 H), 2.40-2.49 (m, 1 H), 3.50-3.57 (m, 2

H), 4.22 (dd, J=8.9.4 Hz, 1 H), 6.62 (d, J=2.15 Hz, 1 H), 7.25 (d, J=8.3 Hz, 2 H), 7.65-7.69 (m, 3 H); MS (ESI) m/e 382.2 (M+H).

Example 37

Trans {4-[4-(1H-pyrazol-3-yl)phenyl]cyclohexyl}acetic acid

Example 37A

Trans (E)-ethyl 2-(4-(4-(3-(dimethylamino)acryloyl)phenyl)cyclohexyl)acetate

The product from Example 26A (2.14 g, 7.42 mmol) and N,N-dimethylformamide dimethylacetal (1.42 g, 11.9 mmol) in N,N-dimethylformamide (20 mL) were heated at 100° C. for 16 h. The solution was cooled to room temperature, and water (20 mL) was added over a period of 10 min. The precipitate was collected by filtration, washed with water (3×20 mL), and dried in vacuo at 50° C. for 24 h to give crude product. $^1$H NMR (500 MHz, DMSO-$d_6$) δ ppm 1.11-1.21 (m, 5H), 1.43-1.55 (m, 2H), 1.63-1.82 (m, 5H), 2.22 (d, J=6.76 Hz, 2H), 2.43-2.47 (m, 1H), 2.90 (s, 3H), 3.12 (s, 3H), 4.07 (q, J=7.06 Hz, 2H), 5.79 (d, J=12.27 Hz, 1H), 7.27 (d, J=8.59 Hz, 2H), 7.67 (d, J=12.27 Hz, 1H), 7.79 (d, J=8.59 Hz, 2H); MS (ESI) m/z 344.1.0 [M+H]$^+$.

Example 37B

Trans ethyl 2-(4-(4-(1H-pyrazol-3-yl)phenyl)cyclohexyl)acetate

The product from Example 37B (1.2 g, 3.5 mmol) was dissolved in ethanol (20 mL), followed by the addition of 35% aqueous hydrazine (2.0 g, 22 mmol). The solution was heated at 80° C. for 2 hours and then evaporated to dryness. The crude product was redissolved in ethyl acetate (100 mL), washed with H$_2$O (2×10 mL), brine (10 mL), and dried over Na$_2$SO$_4$. Removal of the solvent afforded the crude product, which was then purified on a flash column, eluting with 1:1 ethyl acetate/hexanes to provide the title compound as off-white solid. $^1$H NMR (500 MHz, DMSO-$d_6$) δ ppm 1.11-1.21 (m, 5H), 1.43-1.52 (m, 2H), 1.70-1.82 (m, 5H), 2.22 (d, J=6.75 Hz, 2H), 2.46-2.49 (m, 1H), 4.07 (q, J=7.06 Hz, 2H), 6.63 (d, J=1.84 Hz, 1H), 7.25 (d, J=7.36 Hz, 2H), 7.62-7.77 (m, 3H), 12.77 (br, s, 1H); MS (ESI) m/z 313.0 [M+H]$^+$.

Example 37C

Trans {4-[4-(1H-pyrazol-3-yl)phenyl]cyclohexyl}acetic acid

A scintillation vial was charged with the product from Example 37B (31.3 mg, 0.100 mmol), lithium hydroxide (21 mg, 0.50 mmol) and 10 mL of 4:1 tetrahydrofuran/water and placed in a shaker overnight at room temperature. The reaction was neutralized by the addition of 4 M HCl, and the resultant mixture was concentrated and purified by RP-HPLC to provide the title product. $^1$H NMR (500 MHz, DMSO-$d_6$) δ ppm 1.07-1.17 (m, 2H), 1.42-1.53 (m, 2H), 1.70-1.88 (m, 5H), 2.14 (d, J=6.75 Hz, 2H), 2.44-2.48 (m, 1H), 6.63 (d, J=2.15 Hz, 1H), 7.26 (d, J=7.97 Hz, 2H), 7.65 (d, J=2.15 Hz, 1H), 7.68 (d, J=7.97 Hz, 2H), 12.46 (br, s, 2H); MS (ESI) m/z 285.0 [M+H]$^+$.

Example 38

Trans (4-{4-[4-bromo-3-(cyclopropylmethoxy)-1H-pyrazol-5-yl]phenyl}cyclohexyl)acetic acid The title compound was prepared according to the procedure as described in Example 33 by substituting (bromomethyl)cyclopropane for (bromomethyl)cyclobutane. $^1$H NMR (500 MHz, DMSO-$d_6$) δ ppm 0.34 (m, 2H), 0.56 (m, 2H), 1.14 (m, 2H), 1.27 (m, 1H), 1.48 (m, 2H), 1.68-1.87 (m, 5H), 2.14 (d, J=6.75 Hz, 2H), 2.47 (m, 1H), 4.02 (d, J=7.06 Hz, 2H), 7.38 (d, J=8.24 Hz, 2H), 7.62 (d, J=8.24 Hz, 2H), 12.00 (br s, 1H), 12.55 (br s, 1H); MS (ESI) m/z 433.0 [M+H]$^+$.

Example 39

Trans ethyl [4-(4-{3-[2-(1-adamantyl)-2-hydroxyethoxy]-1H-pyrazol-5-yl}phenyl)cyclohexyl]acetate The title compound was prepared according to the procedure as described in Example 1G. $^1$H NMR (500 MHz, DMSO-$d_6$) δ ppm 1.12 (m, 2H), 1.19 (t, J=7.32 Hz, 3H), 1.42-1.99 (m, 22H), 2.22 (d, J=6.71 Hz, 2H), 2.47 (m, 1H), 3.89 (dd, J$_1$=10.38 Hz, J$_2$=7.94 Hz, 1H), 4.02 (m, 1H), 4.06 (q, J=7.32 Hz, 2H), 4.24 (dd, J$_1$=10.37 Hz, J$_2$=2.74 Hz, 1H), 4.71 (s, 1H), 6.07 (s, 1H), 7.28 (d, J=8.24 Hz, 2H), 7.59 (d, J=8.24 Hz, 2H), 12.21 (br s, 1H), MS (ESI) m/z 507.4 [M+H]$^+$.

Example 40

Trans methyl N-methyl-N-[(4-{4-[3-(trifluoromethyl)-1H-pyrazol-5-yl]phenyl}cyclohexyl)acetyl]glycinate To a 20 mL scintillation vial was added the product from Example 26B (30 mg, 0.085 mmol), methyl 2-(methylamino)acetate (10.0 mg, 0.097 mmol), and N,N-dimethylformamide (0.85 mL) followed by O-(7-azabenzotriazol-1-yl)-N,N,N',N'-tetramethyluronium hexafluorophosphate (39.0 mg, 0.102 mmol) and diisopropylethylamine (30 µL, 0.176 mmol). Following 4 hours of stirring, the solvent was evaporated and the residue purified over RP-HPLC to afford the title product. MS (ESI) m/z 438 [M+H]$^+$.

Example 41

Trans [4-(4-{3-[(6,7-dimethoxy-2-oxo-2H-chromen-4-yl)methoxy]-1H-pyrazol-5-yl}phenyl)cyclohexyl]acetic acid The title compound was prepared according to the procedure as described in Example 3 by substituting 4-(bromomethyl)-6,7-dimethoxy-2H chromen-2-one for 2-bromo-1-(4-methoxyphenyl)ethanone. $^1$H NMR (500 MHz, DMSO-$d_6$) δ ppm 1.12 (m, 2H), 1.48 (m, 2H), 1.54-1.86 (m, 5H), 2.14 (d, J=7.02 Hz, 2H), 2.47 (m, 1H), 3.84 (s, 3H), 3.88 (s, 3H), 5.51 (s, 2H), 6.28 (m, 1H), 6.33 (s, 1H), 7.12 (s, 1H), 7.21 (s, 1H), 7.30 (d, J=8.24 Hz, 2H), 7.61 (d J=8.24 Hz, 2H), 12.39 (br s 1H); MS (ESI) m/z 519.4 [M+H]$^+$.

Example 42

Trans N-2H-tetraazol-5-yl-2-(4-{4-[5-(trifluoromethyl)-1H-pyrazol-3-yl]phenyl}cyclohexyl)acetamide To a 20 mL scintillation vial was added the product from Example 28 (30 mg, 0.085 mmol), 2H-tetrazol-5-amine (8.00 mg, 0.088 mmol) and N,N-dimethylformamide (0.85 mL) followed by O-(7-azabenzotriazol-1-yl)-N,N,N',N'-tetramethyluronium hexafluorophosphate (39.0 mg, 0.102 mmol) and diisopropylethylamine (30 μL, 0.176 mmol). Following 4 hours of stirring, the solvent was evaporated and the residue purified over RP-HPLC to afford the title product. $^1$H NMR (500 MHz, DMSO-$d_6$) δ ppm 1.06-1.26 (m, 2 H), 1.43-1.57 (m, 2 H), 1.76-1.92 (m, 5 H), 2.36-2.41 (m, 2 H), 6.96-7.23 (m, 1 H), 7.23-7.46 (m, 2 H), 7.57-7.80 (m, 2 H), 11.99 (s, 1 H), 13.98 (s, 1 H), 15.83 (s, 1 H); MS (ESI) m/z 420 [M+H]$^+$.

Example 43

Trans methyl {4-[4-(3-{[2-(trifluoromethoxy)benzyl]oxy}-1H-pyrazol-5-yl)phenyl]cyclohexyl}acetate A mixture of Example 1E (35 mg, 0.10 mmol), 1-(bromomethyl)-2-(trifluoromethoxy)benzene (26 mg, 0.10 mmol), and potassium carbonate (14 mg, 0.10 mmol) in N,N-dimethylformamide (mL) was heated at 75° C. under N$_2$ for 6 hours. After this time the reaction was cooled to room temperature and filtered through celite, rinsed with ethyl acetate, and then evaporated to afford an oil. The oil was directly treated with lithium hydroxide monohydrate (10 mg, 0.24 mmol) in a mixed solvent (2 mL of tetrahydrofuran, 1 mL of H$_2$O) and shaken at room temperature overnight. The reaction mixture was concentrated and the residue taken up in 1:1 methanol/DMSO without acidification, upon which the methyl ester was formed from the remaining non-hydrolyzed ethyl ester. Purification via RP-HPLC afforded the title product. $^1$H NMR (500 MHz, DMSO-$d_6$) δ ppm 1.13 (m, 2H), 1.47 (m, 2H), 1.70-1.87 (m, 5H), 2.14 (d, J=6.75 Hz, 2H), 2.47 (m, 1H), 3.60 (s, 3H), 5.25 (s, 2H), 6.14 (s, 1H), 7.29 (d, J=8.28 Hz, 2H), 7.38-7.53 (m, 3H), 7.58 (d, J=8.28 Hz, 2H), 7.66 (dd, J$_1$=7.37 Hz, J$_2$=1.84 Hz, 1H), 12.32 (br s, 1H); MS (ESI) m/z 489.3 [M+H]$^+$.

Example 44

Trans ethyl 5-{4-[4-(2-ethoxy-2-oxoethyl)cyclohexyl]phenyl}-1-H-pyrazole-3-carboxylate To a solution of the product from example 26A (0.9 g, 03 mmol) in 20 mL of tetrahydrofuran at −78° C. was added lithium diisopropylamide (3 mL, 2 M solution in tetrahydrofuran, 6 mmol). The mixture was stirred at −78° C. for 30 min, and then a solution of diethyl oxalate (0.46 g, 30 mmol) in 5 mL of tetrahydrofuran was added dropwise. The reaction was allowed to warm to room temperature over 30 min and then stirred at room temperature for 1 hour. After this time the reaction was poured into ice-cold water (100 mL), and then extracted with ethyl acetate (2×100 mL). The combined organic layer was washed with brine, and dried over anhydrous sodium sulfate. Solvent was removed under reduced pressure, and the resulting oil was treated with hydrazine (2 mL, 35% in water) in a mixed solvent (50 mL of 1,4-dioxane, 0.5 mL of acidic acid) under reflux for 2 hours. The reaction mixture was then filtered through celite, washed with ethyl acetate, concentrated and purified on a flash column, eluting with 5% ethyl acetate in hexanes to provide the title compound as colorless oil. $^1$H NMR (500 MHz, DMSO-$d_6$) δ ppm 1.13 (m, 2H), 1.19 (t, J=7.02 Hz, 3H), 1.32 (t, J=7.02 Hz, 3H), 1.49 (m, 2H), 1.70-1.87 (m, 5H), 2.22 (d, J=6.71 Hz, 2H), 2.47 (m, 1H), 4.07 (q, J=7.02 Hz, 2H), 4.80 (q, J=7.02 Hz, 2H), 7.16 (s, 1H), 7.30 (d, J=8.24 Hz, 2H), 7.74 (d, J=8.24 Hz, 2H), 12.32 (br s, 1H); MS (ESI) m/z 385.2 [M+H]$^+$.

Example 45

Trans [4-(4-{3-[(2-hydroxycyclohexyl)oxy]1H-pyrazol-5-yl}phenyl)cyclohexyl]acetic acid A mixture of Example 1E (40 mg, 0.12 mmol), cyclohexane-1.2-(diol (15 mg, 0.15 mmol), 1,1'-(azodicarbonyl) dipiperidine (ADDP) (30 mg, 0.12 mmol) and tributylphosphine (20 mg, 0.1 mmol) in toluene (2 mL) was heated at 90° C. under N$_2$ for 6 hours. The mixture was concentrated and purified on a RP-HPLC. The product isolated was hydrolyzed according to the procedure as described in Example 1H to provide the title product. $^1$H NMR (500 MHz, DMSO-$d_6$) δ ppm 11.06-1.87 (m, 17H), 2.14 (d, J=6.72 Hz, 2H), 2.47 (m, 1H), 3.83 (m, 1H), 4.17 (m, 1H), 6.06 (s, 1H), 7.28 (d, J=8.24 Hz, 2H), 7.31 (m, 1H), 7.60 (d, J=8.24 Hz, 2H), 12.05 (br s, 1H); MS (ESI) m/z 399.2 [M+H]$^+$.

Example 46

Trans {4-[4-(3-hydroxy-1H-pyrazol-5-yl)phenyl]cyclohexyl}acetic acid

The title compound was prepared using the procedure as described in Example 1H, substituting the product of Example 1E for the product from Example 1G. $^1$H NMR (500 MHz, DMSO-$d_6$) δ ppm 1.13 (m, 2H), 1.46 (m, 2H), 1.53-1.87 (m, 5H), 2.14 (d, J=7.02 Hz, 2H), 2.47 (m, 1H), 5.86 (s, 1H), 7.26 (d, J=8.24 Hz, 2H), 7.58 (d, J=8.24 Hz, 2H); MS (ESI) m/z 301.0 [M+H]$^+$.

Example 47

Trans methyl (4-{4-[3-(cyclohexyloxy)-1H-pyrazol-5-yl]phenyl}cyclohexyl)acetate

A mixture of Example 1E (40 mg, 0.12 mmol), cyclohexanol (15 mg, 0.15 mmol), 1,1'-(azodicarbonyl) dipiperidine (ADDP) (30 mg, 0.12 mmol) and tributylphosphine (20 mg, 0.1 mmol) in toluene (2 mL) was heated at 90° C. under N$_2$ for 6 hours. The reaction mixture was filtered through celite, washed with ethyl acetate, and concentrated. The residue was then subjected to hydrolysis using lithium hydroxide monohydrate (10 mg, 0.24 mmol) in a mixed solvent (2 mL of tetrahydrofuran, 1 mL of H$_2$O). It was placed in a shaker at room temperature overnight. The reaction mixture was concentrated and the residue taken up in 1:1 methanol/DMSO without acidification, upon which the methyl ester was formed from the remaining non-hydrolyzed ethyl ester. Purification via RP-HPLC afforded the title product. $^1$H NMR (500 MHz, DMSO-$d_6$) δ ppm 1.13 (m, 2H), 1.2-1.56 (m, 8H), 1.67-1.86 (m, 7H), 1.97 (m, 2H), 2.14 (d, J=6.71 Hz, 2H), 2.47 (m, 1H), 3.60 (s, 3H), 4.39 (m, 1H), 6.06 (s, 1H), 7.27 (d, J=8.24 Hz, 2H), 7.58 (d, J=8.24 Hz, 2H), 12.20 (br s, 1H); MS (ESI) m/z 383.2 [M+H]$^+$.

Example 48

Trans [4-(4-{2-[(3-methoxyphenyl)amino]-1,3-thiazol-4-yl}phenyl)cyclohexyl]acetic acid

Example 48A

Trans ethyl {4-[4-(bromoacetyl)phenyl]cyclohexyl}acetate

To a solution containing the product from Example 1B (1.5 g, 6.1 mmol) and AlCl$_3$ (2.4 g, 18 mmol) in 10 mL of dichloromethane at 0° C. was added bromoacetyl bromide (0.55 mL, 6.2 mmol). The mixture was stirred at room temperature for 30 min, to one hour. Upon completion of the reaction as monitored by thin layer chromatography, the reaction mixture was poured into ice-cold water (100 mL), and extracted with dichloromethane (2×100 mL). The combined organic layers were washed with brine, dried over anhydrous sodium sulfate and filtered. The solvent was removed under reduced pressure, and the resulting oil was purified by flash chromatography (ethyl acetate/hexane, 1/8) to afford the title compound as a white solid. $^1$H NMR (500 MHz, DMSO-$d_6$) δ ppm 1.13 (m, 2H), 1.19 (t, J=7.06 Hz, 3H), 1.50 (m, 2H), 1.70-1.85 (m, 5H), 2.22 (d, J=6.75 Hz, 2H), 2.56 (m, 1H), 4.07 (q, J=7.06 Hz, 3H), 4.88 (s, 2H), 7.41 (d J=8.28 Hz, 2H), 8.92 (d, J=8.28 Hz, 2H); MS (ESI) m/z 367.1 [M+H]$^+$.

Example 48B

Trans [4-(4-{2-[(3-methoxyphenyl)amino]-1,3-thiazol-4-yl}phenyl)cyclohexyl]acetic acid 1-(3-Methoxyphenyl)-2-thiourea (0.01 g, 0.054 mmol) was added to a solution of the product from-Example 48A (0.02 g, 0.054 mmol) in ethanol (0.5 mL) and heated at 80° C. for 1 h. The solvent was then removed in vacuo and the residue taken up in tetrahydrofuran (1 mL) and water (0.5 mL). Lithium hydroxide monohydrate (0.005 g, 0.1 mmol) was added to the reaction mixture and stirred at 50° C. for 3 h. The solvents were then removed and the residue purified by RP-HPLC to afford the title compound as a white solid. $^1$H NMR (500 MHz, DMSO-$d_6$) δ ppm 1.09-1.18 (m, 2 H), 1.45-1.54 (m, 2 H), 1.62-1.69 (m, 1 H), 1.70-1.77 (m, 1 H), 1.80-1.88 (m, 4 H), 2.13 (d, J=7 Hz, 2 H), 3.78 (s, 3 H), 6.54 (dd, J=8.24, 1.83 Hz, 1 H), 7.10-7.16 (m, 1H), 7.20-7.27 (m, 1 H), 7.29 (d, J=8.24 Hz, 2 H), 7.51-7.56 (m, 1 H), 7.79-7.83 (d, J=8.24 Hz, 2 H), 10.25 (s, 1 H), 12.05 (s, 1 H), MS (ESI) m/e 423.2 (M+H).

Example 49

Trans ethyl (4-{4-[5-(trifluoromethyl)-1H-pyrazol-3-yl]phenyl}cyclohexyl)acetate The title compound was prepared using the procedure as described in Example 26B.

Example 50

Trans 2-methyl-N-[(4-{4-[5-(trifluoromethyl)-1H-pyrazol-3-yl]phenyl}cyclohexyl)acetyl]alanine A 20 mL scintillation vial was charged with the product from Example 73 (12.0 mg, 0.027 mmol), dichloromethane (1 mL), and trifluoroacetic acid (0.5 mL) and the reaction vessel shaken for 6 hours at room temperature. After this time the reaction solvents were evaporated and the residue taken up in toluene and evaporated to afford the title product. $^1$H NMR (500 MHz, DMSO-$d_6$) δ ppm 1.02-1.15 (m, 2H), 1.23-1.30 (m, 1 H), 1.31-1.35 (m, 6 H), 1.40-1.53 (m, 2 H), 1.70-1.78 (m, 1 H), 1.76-1.87 (m, 4 H), 1.92-2.03 (m, 2 H), 6.97-7.21 (m, 1 H), 7.24-7.46 (m, 2 H), 7.60-7.83 (m, 2 H), 8.00 (s, 1 H), 13.99 (s, 1 H); MS (ESI) m/z 438 [M+H]$^+$.

Example 51

Trans {4-[4-(4-ethyl-1-methyl-1H-pyrazol-3-yl)phenyl]cyclohexyl}acetic acid

A 100 mL round bottom flask with a stir bar was charged with the product of Example 1B (0.5 g, 2.03 mmol) and 16 mL of dichloromethane. The reaction solution was cooled to 0° C. and AlCl$_3$ (0.811 g, 6.09 mmol) was added in portions. The mixture was allowed to stir for 20 min, and then butyryl chloride (251 μL, 2.44 mmol) was added dropwise. After stirring for 15 minutes, the reaction mixture was slowly pored into a beaker with ice water and diluted with 120 mL of ethyl acetate. The layers were separated and the organic layer washed with 1 N NaHCO$_3$ (×2), brine (×2), dried over Na$_2$SO$_4$, and filtered. Evaporation of the solvents afforded a clear oil. This material was then dissolved in N,N-dimethylfomamide (2 mL) and 140 μL of dimethyl formamide dimethyl acetal was added. The reaction solution was then heated to 95° C., and stirred at this temperature for 10 hours. After this time the reaction solution was cooled to room temperature and the solvents evaporated. The residue was dissolved in 5 mL of ethanol and methyl hydrazine (108 μL, 2.03 mmol) was added. The solution was heated to reflux for 6 hours. Evaporation of the solvents and dissolution in 4:1 tetrahydrofuran/H$_2$O was followed by the addition of lithium hydroxide (100 mg, 2.38 mmol). The reaction mixture was shaken at room temperature for 110 hours (TLC indicated completion of hydrolysis), and then filtered. The solvents were evaporated and the residue taken up in 1:1 DMSO/methanol and purified over RP-HPLC to afford the title product. $^1$H NMR (400 MHz, DMSO-$d_6$) δ ppm 1.06-1.12 (m, 1 H), 1.12-1.18 (m, 3 H), 1.37-1.55 (m, 2 H), 1.55-1.68 (m, 1 H), 1.69-1.78 (m, 1 H), 1.78-1.88 (m, 4 H), 2.09-2.19 (m, 2 H), 2.41-2.48 (m, 1 H), 2.53-2.62 (m, 2 H), 3.76-3.84 (m, 3 H), 7.20-7.28 (m, 2 H), 7.45-7.55 (m, 3 H); MS (ESI) m/z 327 [M+H]$^+$.

Example 52

Trans (4-{4-[3-(tetrahydro-2H-pyran-4-ylmethoxy)-1H-pyrazol-5-yl]phenyl}cyclohexyl)acetic acid The title compound was prepared according to the procedure as described in Example 3 by substituting 4-(bromomethyl)tetrahydro-2H-pyran for (bromomethyl)cyclobutane. $^1$H NMR (500 MHz, DMSO-$d_6$) δ ppm 1.13 (m, 2H), 1.31 (m, 2H), 1.48 (m, 2H), 1.55-1.86 (m, 7H), 2.00 (m, 1H), 2.14 (d, J=6.71 Hz, 2H), 2.47 (m, 1H), 3.32 (m, 2H), 3.87 (m, 2H), 3.94 (d, J=6.40 Hz, 2H), 6.08 (s, 1H), 7.27 (d, J=8.24 Hz, 2H), 7.58 (d, J=8.24 Hz, 2H), 12.20 (br s, 1H); MS (ESI) m/z 383.2 [M+H]$^+$.

Example 53

Trans (4-{4-[4-bromo-3-(tetrahydro-2H-pyran-4-ylmethoxy)-1H-pyrazol-5-yl]phenyl}cyclohexyl)acetic acid The title compound was prepared according to the procedure as described in Example 33 by substituting 4-(bromomethyl)tetrahydro-2H-pyran for (bromomethyl)cyclobutane. $^1$H NMR (500 MHz, DMSO-$d_6$) δ ppm 1.14 (m, 2H), 1.34 (m, 2H), 1.48 (m, 2H), 1.61-1.88 (m, 7H), 2.03 (m, 1H), 2.14 (d, J=7.06 Hz, 2H), 2.47 (m, 1H), 3.36 (m, 2H), 3.87 (m, 2H), 4.04 (d, J=6.44 Hz, 2H), 7.37 (d, J=8.28 Hz, 2H), 7.62 (d, J=8.28 Hz, 2H), 11.99 (br s, 1H), 12.57 (br s, 1H); MS (ESI) m/z 477.0 [M+H]$^+$.

Example 54

Trans {4-[4-(2-{[2-(trifluoromethyl)phenyl]amino}-1,3-thiazol-4-yl)phenyl]cyclohexyl}acetic acid The title compound was prepared according to the procedure as described in Example 48B substituting 1-(2-trifluoromethylphenyl)-2-thiourea for 1-(3-methoxyphenyl)-2-thiourea in Example 48B. $^1$H NMR (500 MHz, DMSO-$d_6$) δ ppm 1.07-1.18 (m, 2 H), 1.43-1.52 (m, 2 H), 1.57-1.67 (m, 1 H), 1.70-1.77 (m, 1 H), 1.80-1.88 (m, 4 H), 2.14 (d, J=6.7 Hz, 2 H), 7.20-7.25 (m, 3H), 7.32 (t, J=8.24 Hz, 1 H), 7.68-7.75 (m, 4 H), 8.13 (d, J=8.24 Hz, 1 H), 9.46 (s, 1 H), 12.02 (s, 1H); MS (ESI) m/e 461.2 (M+H).

Example 55

Trans [4-(4-{2-[(3,5-dichlorophenyl)amino]-1,3-thiazol-4-yl}phenyl)cyclohexyl]acetic acid The title compound was prepared according to the procedure described in Example 48B substituting 1-(3,5-dichlorophenyl)-2-thiourea for 1-(3-methoxyphenyl)-2-thiourea in Example 48B. $^1$H NMR (500 MHz, DMSO-$d_6$) δ ppm 1.07-1.18 (m, 2 H), 1.43-1.52 (m, 2 H), 1.57-1.69 (m, 1 H), 1.70-1.77 (m, 1 H), 1.80-1.88 (m, 4 H), 2.14 (d, J=7 Hz, 2 H), 7.14 (m, 1 H), 7.32 (t, J=8.24 Hz, 1 H), 7.36-7.40 (m, 1 H), 7.75-7.85 (m, 4 H), 10.68 (s, 1 H), 12.02 (s, 1 H); MS (ESI) m/e 461.1 (M+H).

Example 56

Trans methyl (4-{4-[3-(cyclopentylmethoxy)-1H-pyrazol-5-yl]phenyl}cyclohexyl)acetate The title compound was prepared according to the procedure as described in Example 43 by substituting (bromomethyl)cyclopentane for 1-(bromomethyl)-2-(trifluoromethoxy)benzene. $^1$H NMR (500 MHz, DMSO-$d_6$) δ ppm 1.14 (m, 2H), 1.31 (m, 2H), 1.44-1.83 (m, 13H), 2.24 (d, J=6.71 Hz, 2H), 2.29 (m, 1H), 2.47 (m, 1H), 3.60 (s, 3H), 3.95 (d, J=7.02 Hz, 2H), 6.07 (s, 1H), 7.29 (d, J=8.24 Hz, 2H), 7.68 (d, J=8.24 Hz, 2H), 12.11 (br s, 2H); MS (ESI) m/z 383.2 [M+H]$^+$.

Example 57

Trans ethyl {4-[4-(3-{[5-(trifluoromethyl)-2-furyl]methoxy}-1H-pyrazol-5-yl)phenyl]cyclohexyl}acetate The title compound was prepared according to the procedure as described in Example 1F by substituting 2-(bromomethyl)-5-(ti-difluoromethyl)furan for 1-adamantyl bromomethyl ketone. $^1$H NMR (500 MHz, DMSO-$d_6$) δ ppm 1.15 (m, 2H), 1.19 (t, J=7.06 Hz, 3H), 1.48 (m, 2H), 1.71-1.85 (m, 5H), 2.22 (d, J=6.75 Hz, 2H), 2.47 (m, 1H), 4.07 (q, J=7.06 Hz, 2H), 5.21 (s, 2H), 6.15 (s, 1H), 6.79 (d, J=3.68 Hz, 1H), 7.22 (m, 1H), 7.29 (d, J=8.28 Hz, 2H), 7.59 (d, J=8.28 Hz, 2H), 12.35 (br s, 1H); MS (ESI) m/z 477.3 [M+H]$^+$.

Example 58

Trans [4-(4-{2-[(2-chlorophenyl)amino]-1,3-thiazol-4-yl}phenyl)cyclohexyl]acetic acid The title compound was prepared according to the procedure as described in Example 48B substituting 1-(2-chlorophenyl)-2-thiourea for 1-(3-methoxyphenyl)-2-thiourea in Example 48B. $^1$H NMR (500 MHz, DMSO-$d_6$) δ ppm 1.07-1.18 (m, 2 H), 1.43-1.52 (m, 2 H), 1.57-1.67 (m, 1 H), 1.70-1.77 (m, 1 H), 1.80-1.88 (m, 4 H), 2.14 (d, J=7 Hz, 2 H), 7.06 (dt, J=8.1.53 Hz, 1 H), 7.27 (d, J=8.24 Hz, 2 H), 7.29 (s, 1H), 7.38 (dt, J=8.1.53 Hz, 1 H), 7.48 (dd, J=8, 1.53 Hz, 1 H), 7.78 (d, J=8.24 Liz, 1 H), 8.47 (d, J=8.24 Hz, 1 H), 9.66 (s, 1 H), 12.02 (s, 1 H); MS (ESI) m/e 427.1 (M+H).

Example 59

Trans (4-{4-[1,2-bis(cyclobutylmethyl)-5-oxo-2,5-dihydro-1H-pyrazol-3-yl]phenyl}cyclohexyl)acetic acid The title compound was prepared according to the procedure as described in Example 3 by substituting (bromomethyl)cyclobutane for 2-bromo-1-(4-methoxyphenyl)ethanone. $^1$H NMR (500 MHz, DMSO-$d_6$) δ ppm 1.14 (m, 2H), 1.48 (m, 2H), 1.55-1.94 (m, 15H), 2.04 (m, 2H), 2.15 (d, J=6.71 Hz, 2H), 2.47 (m, 1H), 2.69-2.72 (m, 2H), 3.92 (d, J=7.02 Hz, 2H), 4.02 (d, J=6.71 Hz, 2H), 5.71 (s, 1H), 7.33 (m, 4H), 12.00 (br s, 1H); MS (ESI) m/z 437.3 [M+H]$^+$.

Example 60

Trans {4-[4-(2-{[3-(trifluoromethyl)phenyl]amino}1,3-thiazol-4-yl)phenyl]cyclohexyl}acetic acid The title compound was prepared according to the procedure as described in Example 48B substituting 1-(3-trifluoromethylphenyl)-2-thiourea for 1-(3-methoxyphenyl)-2-thiourea in Example 48B. $^1$H NMR (500 MHz, DMSO-$d_6$) δ ppm 1.07-1.18 (m, 2 H), 1.43-1.52 (m, 2 H), 1.57-1.67 (m, 1 H), 1.70-1.77 (m, 1 H), 1.80-1.88 (m, 4 H), 2.15 (d, J=7 Hz, 2 H), 7.25-7.35 (m, 3 H), 7.35 (s, 1 H), 7.57 (d, J=7.9 Hz, 1 H), 7.80-7.90 (m, 3 H), 8.38 (s, 1 H), 10.63 (s, 1 H), 12.02 (s, 1 H); MS (ESI) m/e 461.2 (M+H).

Example 61

Trans methyl (4-{4-[3-(cyclopentyloxy)-1H-pyrazol-5-yl]phenyl}cyclohexyl)acetate The title compound was prepared according to the procedure as described in Example 47 by substituting cyclopentanol for cyclohexanol. $^1$H NMR (500 MHz, DMSO-$d_6$) δ ppm 1.13 (m, 2H), 1.48 (m, 2H), 1.53-1.91 (m, 13H), 2.24 (d, J=6.72 Hz, 2H), 2.47 (m, 1H), 3.60 (s, 3H), 4.89 (m, 1H), 6.04 (s, 1H), 7.28 (d, J=8.24 Hz, 2H), 7.58 (d, J=8.24 Hz, 2H), 12.00 (br s, 2H); MS (ESI) m/z 383.2 [M+H]$^+$.

Example 62

Trans ethyl (4-{4-[3-(2,3-dihydro-1,4-benzodioxin-2-ylmethoxy)-1H-pyrazol-5-yl]phenyl}cyclohexyl)acetate The title compound was prepared according to the procedure as described in Example 1F by substituting 2-(bromomethyl)-2,3-dihydrobenzo[b][1,4]dioxine for 1-adamantyl bromomethyl ketone. $^1$H NMR (500 MHz, DMSO-$d_6$) δ ppm 1.15 (m, 2H), 1.19 (t, J=7.06 Hz, 3H), 1.48 (m, 2H), 1.71-1.85 (m, 5H), 2.24 (d, J=6.75 Hz, 2H), 2.47 (m, 1H), 4.07 (q, J=7.06 Hz, 2H), 4.12 (dd, $J_1$=11.35 Hz, $J_2$=7.06 Hz, 1H), 4.34 (m, 1H), 4.41 (dd, $J_1$=11.35 Hz, $J_2$=2.45 Hz, 1H), 4.57 (m, 1H), 6.14 (s, 1H), 6.82-6.94 (m, 4H), 7.29 (d, J=8.28 Hz, 2H), 7.59 (d, J=8.28 Hz, 2H), 12.33 (br s, 1H); MS (ESI) m/z 477.3 [M+H]$^+$.

Example 63

Trans methyl 1-({4-[4-(1H-pyrazol-3-yl)phenyl]cyclohexyl}acetyl)-L-prolinate

L-Proline methyl ester hydrochloride (0.03 g, 0.18 mmol) was added to a stirred solution of the product from Example 37C (0.05 g, 0.17 mmol), 1-ethyl-3-[3-(dimethylamino)propyl]-carbodiimide hydrochloride (0.042 g, 0.22 mmol), 1-hydroxybenzotriazole hydrate (0.03 g, 0.22 mmol) and N-methyl morpholine (0.1 mL, 0.87 mmol) in N,N-dimethylformamide (4 mL) at room temperature. The reaction was stirred at room temperature for 12 h and then quenched by addition of water. It was then extracted with ethyl acetate (3×25 mL), the organic extracts washed with water, brine, dried ($MgSO_4$) and concentrated to afford the titled compound as a clear oil. $^1$H NMR (500 MHz, DMSO-$d_6$) δ ppm 1.09-1.18 (m, 2 H), 1.40-1.51 (m, 2 H), 1.75-1.86 (m, 6 H), 1.88-1.94 (m, 2 H), 2.13-2.27 (m, 3 H), 2.40-2.49 (m, 1 H), 3.51-3.58 (m, 2 H), 3.61 (s, 3 H), 4.30 (dd, J=10, 5 Hz, 1 H), 6.64 (d, J=3 Hz, 1 H), 7.27 (d, J=10 Hz, 2 H), 7.66-7.72 (m, 3 H).

Example 64

Trans [4-(4-{2-[(2-methylphenyl)amino]-1,3-thiazol-4-yl}phenyl)cyclohexyl]acetic acid The title compound was prepared according to the procedure as described in Example 48B substituting 1-(2-methylphenyl)-2-thiourea for 1-(3-methoxyphenyl)-2-thiourea in Example 48B. $^1$H NMR (500 MHz, DMSO-$d_6$) δ ppm 1.07-1.16 (m, 2 H), 1.43-1.52 (m, 2 H), 1.57-1.67 (m, 1 H), 1.70-1.77 (m, 1 H), 1.80-1.88 (m, 4 H), 2.14 (d, J=7 Hz, 2 H), 2.29 (s, 3 H), 7.00-7.05 (m, 1 H), 7.15-7.19 (m, 2 H), 7.20-7.25 (m, 3 H), 7.75 (d, J=8.24 Hz, 2 H), 7.99 (d, J=8.24 Hz, 1 H), 9.30 (s, 1 H), 12.02 (s, 1 H); MS (ESI) m/e 407.2 (M+H).

Example 65

Trans [4-(4-{2-[(4-chlorophenyl)amino]-1,3-thiazol-4-yl}phenyl)cyclohexyl]acetic acid The title compound was prepared according to the procedure as described in Example 48B substituting 1-(4-chlorophenyl)-2-thiourea for 1-(3-methoxyphenyl)-2-thiourea in Example 48B. $^1$H NMR (500 MHz, DMSO-$d_6$) δ ppm 1.07-1.18 (m, 2 H), 1.43-1.52 (m, 2 H), 1.57-1.67 (m, 1 H), 1.70-1.77 (m, 1 H), 1.80-1.88 (m, 4 H), 2.15 (d, J=7 Hz, 2 H), 7.27-7.29 (m, 3 H), 7.39 (d, J=9 Hz, 2 H), 7.75 (d, J=9 Hz, 2 H), 7.81 (d, J=8.24 Hz, 2 H), 10.4 (s, 1 H), 12.03 (s, 1 H); MS (ESI) m/e 427.1 (M+H).

Example 66

Trans [4-(4-{2-[(3-chlorophenyl)amino]-1,3-thiazol-4-yl}phenyl)cyclohexyl]acetic acid The title compound was prepared according to the procedure as described in Example 48B substituting 1-(3-chlorophenyl)-2-thiourea for 1-(3-methoxyphenyl)-2-thiourea in Example 48B. $^1$H NMR (500 MHz, DMSO-$d_6$) δ ppm 1.07-1.18 (m, 2 H), 1.43-1.52 (m, 2 H), 1.57-1.67 (m, 1 H), 1.70-1.77 (m, 1 H), 1.80-1.88 (m, 4 H), 2.15 (d, J=7 Hz, 2 H), 7.00 (dd, J=8, 1.53 Hz, 1 H), 7.30 (d, J=8.24 Hz, 2 H), 7.36 (t, J=8 Hz, 1 H), 7.57 (dd, J=8, 1.53 Hz, 1 H), 7.80 (d, J=8.24 Hz, 2 H), 7.98 (t, J=1.53 Hz, 1 H), 10.48 (s, 1 H), 12.03 (s, 1 H); MS (ESI) m/e 427.1 (M+H).

Example 67

Trans ethyl (4-{4-[3-(pyridin-2-ylmethoxy)-1H-pyrazol-5-yl]phenyl}cyclohexyl)acetate The title compound was prepared according to the procedure as described in Example 1F by substituting 2-(bromomethyl)pyridine for 1-adamantyl bromomethyl ketone. 1H NMR (500 MHz, DMSO-$d_6$) δ ppm 1.14 (m, 2H), 1.19 (t, J=7.32 Hz, 3H), 1.48 (m, 2H), 1.71-1.85 (m, 5H), 2.22 (d, J=6.71 Hz, 2H), 2.47 (m, 1H), 4.07 (q, J=7.32 Hz, 2H), 5.80 (s, 2H), 6.18 (s, 1H), 7.29 (d, J=8.28 Hz, 2H), 7.43 (m, 1H), 7.59 (m, 3H), 7.94 (m, 1H), 8.61 (m, 1H), 12.33 (br s, 1H); MS (ESI) m/z 420.2 [M+H]$^+$.

Example 68

Trans ethyl (4-{4-[3-(tetrahydrofuran-2-ylmethoxy)-1H-pyrazol-5-yl]phenyl}cyclohexyl)acetate The title compound was prepared according to the procedure as described in Example 1F by substituting 2-(bromomethyl)tetrahydrofuran for 1-adamantyl bromomethyl ketone. $^1$H NMR (500 MHz, DMSO-$d_6$) δ ppm 1.13 (m, 2H), 1.19 (t, J=7.02 Hz, 3H), 1.48 (m, 2H), 1.61-1.91 (m, 8H), 1.98 (m, 1H), 2.22 (d, J=6.75 Hz, 2H), 2.47 (m, 1H), 3.67 (m, 1H), 3.78 (m, 1H), 4.04 (m, 2H), 4.07 (q, J=7.02 Hz, 3H), 4.14 (m, 1H), 6.08 (s, 1H), 7.28 (d, J=8.24 Hz, 2H), 7.58 (d, J=8.24 Hz, 2H), 12.21 (br s, 1H); MS (ESI) m/z 413.2 [M+H]$^+$.

Example 69

Trans (4-{4-[3-(tetrahydro-2H-pyran-4-yloxy)-1H-pyrazol-5-yl]phenyl}cyclohexyl)acetic acid A mixture of Example 1E (40 mg, 0.12 mmol), tetrahydro-2H-pyran-4-ol (15 mg, 0.15 mmol), 1,1'-(azodicarbonyl)dipiperidine (ADDP) (30 mg, 0.12 mmol) and tributylphosphine (20 mg, 0.1 mmol) in toluene (2 mL) was heated at 90° C. under $N_2$ for 6 hours. The mixture was concentrated and purified on a RP-HPLC, and the isolated product was hydrolyzed according to the procedure as described in Example 1H to provide the title product. $^1$H NMR (500 MHz, DMSO-$d_6$) δ ppm 1.13 (m, 2H), 1.48 (m, 2H), 1.62 (m, 2H), 1.67-1.88 (m, 5H), 2.02 (m, 2H), 2.14 (d, J=7.01 Hz, 2H), 2.47 (m, 1H), 3.46 (m, 2H), 3.85 (m, 2H), 4.62 (m, 1H), 6.10 (s, 1H), 7.28 (d, J=8.24 Hz, 2H), 7.58 (d, J=8.24 Hz, 2H), 12.16 (br s, 2H); MS (ESI) m/z 385.1 [M+H]$^+$.

Example 70

Trans ethyl (4-{4-[2-(formylamino)-1,3-oxazol-4-yl]phenyl}cyclohexyl)acetate

A mixture of the product from Example 48A (100 mg, 0.27 mmol) and urea (33 mg, 0.54 mmol) in N,N-dimethylformamide (5 mL) was heated at 90-95° C. under $N_2$ for 2 hours. The mixture was concentrated, and purified on a RP-HPLC to provide the title product. $^1$H NMR (500 MHz, DMSO-$d_6$) δ ppm 1.13 (m, 2H), 1.19 (t, J=7.05 Hz, 3H), 1.48 (m, 2H), 1.69-1.85 (m, 5H), 2.22 (d, J=6.75 Hz, 2H), 2.47 (m, 1H), 4.07 (q, J=7.05 Hz, 3H), 4.14 (m, 1H), 7.28 (d, J=8.29 Hz, 2H), 7.63 (d, J=8.29 Hz, 2H), 8.29 (s, 1H), 8.95 (br s, 1H), 11.50 (br s, 1H); MS (ESI) m/z 356.9 [M+H]$^+$.

Example 71

Trans 1-({4-[4-(1H-pyrazol-3-yl)phenyl]cyclohexyl}acetyl)-L-prolinamide

The title compound was prepared according to the procedure as described in Example 63 substituting L-prolinamide for L-proline methyl ester hydrochloride in Example 63. $^1$H NMR (400 MHz, DMSO-d$_6$) (ppm 1.05-1.18 (m, 2 H), 1.40-1.51 (m, 2 H), 1.70-1.95 (m, 8 H), 2.11-2.27 (m, 3 H), 2.40-2.49 (m, 1 H), 3.34-3.62 (m, 2 H), 4.22 (dd, J=8.9, 4 Hz, 1 H), 6.65 (d, J=2.15 Hz, 1 H), 7.27 (d, J=8.3 Hz, 2 H), 7.65-7.69 (m, 3 H); MS (ESI) m/e 381.2 (M+H).

Example 72

Trans ethyl (4-{4-[3-(cyclohexylmethoxy)-1H-pyrazol-5-yl]phenyl}cyclohexyl)acetate The title compound was prepared according to the procedure as described in Example 1F by substituting (bromomethyl)cyclohexane for 1-adamantyl bromomethyl ketone. $^1$H NMR (500 MHz, DMSO-d$_6$) δ ppm 0.96-1.84 (m, 23H), 2.22 (d, J=6.71 Hz, 2H), 2.47 (m, 1H), 3.89 (m, 2H), 4.06 (q, J=7.02 Hz, 2H), 6.06 (s, 1H), 7.29 (d, J=8.24 Hz, 2H), 7.59 (d, J=8.24 Hz, 2H), 12.21 (br s, 1H); MS (ESI) m/z 425.2 [M+H]$^+$.

Example 73

Trans tert-butyl 2-methyl-N-[(4-{4-[3-(trifluoromethyl)-1H-pyrazol-5-yl]phenyl}cyclohexyl)acetyl]alaninate To a 20 mL scintillation vial was added the product from Example 28 (30 mg, 0.085 mmol), tert-butyl 2-amino-2-methylpropanoate (15.0 mg, 0.088 mmol), and N,N-dimethylformamide (0.85 mL) followed by O-(7-azabenzotriazol-1-yl)-N,N,N'N'-tetramethyluronium hexafluorophosphate (39.0 mg, 0.102 mmol) and diisopropylethylamine (30 μL, 0.176 mmol). Following 4 hours of stirring, the solvent was evaporated and the residue purified over RP-HPLC to afford the title product. $^1$H NMR (500 MHz, DMSO-d$_6$) δ ppm 1.01-1.16 (m, 2 H), 1.26-1.31 (m, 6 H), 1.35 (s, 9 H), 1.40-1.53 (m, 2 H), 1.68-1.77 (m, 1 H), 1.77-1.90 (m, 4 H), 1.93-2.02 (m, 2 H), 8.01 (s, 1 H), 13.98 (s, 1 H); MS (ESI) m/z 494 [M+H]$^+$.

Example 74

Trans (4-{4-[2-(formylamino)-1,3-oxazol-4-yl]phenyl}cyclohexyl)acetic acid

The title compound was obtained by hydrolysis of the product of Example 70 by using the procedure as described in Example 1H. $^1$H NMR (500 MHz, DMSO-d$_6$) δ ppm 1.13 (m, 2H), 1.48 (m, 2H), 1.63-1.91 (m, 5H), 2.15 (d, J=7.06 Hz, 2H), 2.47 (m, 1H), 4.07 (q, J=7.05 Hz, 3H), 4.14 (m, 1H), 7.28 (d, J=8.28 Hz, 2H), 7.63 (d, J=8.28 Hz, 2H), 8.29 (s, 1H), 8.96 (br s, 1H), 11.64 (br s, 2H); MS (ESI) m/z 329.0 [M+H]$^+$.

Example 75

Trans [4-(4-{2-[(2-fluorophenyl)amino]-1,3-thiazol-4-yl}phenyl)cyclohexyl]acetic acid The title compound was prepared according to the procedure as described in Example 48B substituting 1-(2-fluorophenyl)-2-thiourea for 1-(3-Methoxyphenyl)-2-thiourea in Example 48B. $^1$H NMR (500 MHz, DMSO-d$_6$) δ ppm 1.07-1.18 (m, 2 H), 1.43-1.52 (m, 2 H), 1.57-1.67 (m, 1 H), 1.70-1.77 (m, 1 H), 1.80-1.88 (m, 4 H), 2.15 (d, J=7 Hz, 2 H), 7.00 (1H), 7.20-7.26 (m, 2H), 7.27-7.33 (m, 3 H), 7.79 (d, J=8.24 Hz, 2 H), 8.59 (t, J=7.32 Hz, 1 H), 10.04 (s, 1 H), 12.03 (s, 1 H); MS (ESI) m/e 411.1 (M+H).

Example 76

Trans ethyl {4-[4-(4-bromo-3-{[(2R)-3-hydroxy-2-methylpropyl]oxy}-1H-pyrazol-5-yl)phenyl]cyclohexyl}acetate The title compound was prepared according to the procedure as described in step A of Example 33 by substituting (R)-3-bromo-2-methylpropan-1-ol for (bromomethyl)cyclobutane. $^1$H NMR (500 MHz, DMSO-d$_6$) δ ppm 0.95 (d, J=7.02 Hz, 2H), 1.14 (m, 2H), 1.19 (t, J=7.02 Hz, 3H), 1.50 (m, 2H), 1.71-1.84 (m, 6H), 2.01 (m, 1H), 2.23 (d, J=7.02 Hz, 2H), 2.47 (m, 1H), 3.39 (m, 1H), 3.42 (m, 1H), 4.02 (dd, J$_1$=10.06 Hz, J$_2$=6.40 Hz, 1H), 4.07 (q, J=7.02 Hz, 2H), 4.16 (dd, J$_1$=10.06 Hz, J$_2$=6.40 Hz, 1H), 7.37 (d, J=8.24 Hz, 2H), 7.62 (d, J=8.24 Hz, 2H), 12.57 (br s, 1H); MS (ESI) m/z 481.0 [M+H]$^+$.

Example 77

[4-(4'-hydroxy-1,1'-biphenyl-4-yl)cyclohexyl]acetic acid

Example 77A 4-(4-benzyloxyphenyl)cyclohexanone 4-(4-Hydroxyphenyl)cyclohexanone (4.98 g, 26.18 mmol), benzyl bromide (4.92 g, 28.79 mmol), K$_2$CO$_3$ (5.06 g, 36.65 mmol) and 75 mL of acetone were mixed in a reaction flask equipped with a reflux condenser. The mixture was heated to reflux and stirred overnight. The mixture was cooled to room temperature and water was added. The mixture was extracted with ethyl acetate three times. The combined organic layers were dried over Na$_2$SO$_4$, filtered and concentrated. The resulting solid was recrystallized in ethyl acetate to provide the titled compound. $^1$H NMR (300 MHz, CDCl$_3$) δ ppm 1.80-2.00 (m, 2 H), 2.13-2.26 (m, 2 H), 2.43-2.55 (m, 4 H), 2.91-3.05 (m, 1 H), 5.05 (s, 2 H), 6.94 (d, J=8.82 Hz, 2 H), 7.16 (d, J=8.82 Hz, 2 H), 7.28-7.48 (m, 5 H); MS (DCI) m/z 298 (M–NH$_4$)$^+$.

Example 77B ethyl 2-(4-(4-(benzyloxy)phenyl)-cyclohexylidene)acetate

The title compound was prepared using procedures as described in Example 1A, substituting the product from Example 77A for 4-phenylcyclohexanone. $^1$H NMR (300 MHz, CDCl$_3$) δ ppm 1.29 (t, J=7.12 Hz, 3H), 1.55-1.69 (m, 2 H), 1.95-2.10 (m, 3 H), 2.27-2.43 (m, 2 H), 2.67-2.81 (m, 1

H), 3.89-4.00 (m, 1 H), 4.16 (q, J=7.12 Hz, 2 H), 5.04 (s, 2 H), 5.67 (s, 1 H), 6.91 (d, J=8.82 Hz, 2 H), 7.12 (d, J=8.82 Hz, 2 H), 7.28-7.46 (m, 5 H); MS (DCI) m/z 368 (M+NH$_4$)$^+$.

Example 77C ethyl [4-(4-hydroxyphenyl)cyclohexyl]acetate

The title compound was hydrogenated in a similar manner to that described in Example 1B by substituting the product from Example 77B for the product from Example 1A. The product was a mixture of trans- and cis-isomers with a 78:22 ratio. $^1$H NMR (300 MHz, CDCl$_3$) δ ppm 1.14 and 1.64 (m, 2H), 1.27 and 1.26 (t, J=7.1 Hz, 3H), 1.84 and 2.30 (m, 1H), 1.87 (m, 2H), 1.45 (m, 2H), 1.87 and 1.67 (m, 2H), 1.84 and 2.3 (m, 1H), 2.23 and 2.42 (d, J=6.7 Hz, 2H), 4.14 (q, J=7.1 Hz, 2H), 6.76 (d, J=8.5 Hz, 2H), 7.06 (d, J=8.5 Hz, 2H); MS (DCI) m/z 280 (M+NH$_4$)$^+$.

Example 77D ethyl 2-(4-(4-(trifluoromethylsulfonyloxy)phenyl) cyclohexyl)acetate The product from Example 77C (1.83 g, 6.99 mmol), 4-(dimethylamino)pyridine (85 mg, 0.7 mmol) and pyridine (15 mL) were mixed in a reaction flask and cooled to 0° C. Trifluoroacetic anhydride (1.88 mL, 11.18 mmol) was added via a syringe. After the reaction was completed, ethyl acetate and 1N HCl were added. The combined ethyl acetate extracts were dried over Na$_2$SO$_4$ and concentrated. The crude mixture was purified by flash chromatography (5% then 10-14% ethyl acetate/hexanes) to give the title compound. $^1$NMR (300 MHz, CDCl$_3$) δ ppm 1.09-1.21 (m, 2 H), 1.27 (t, J=7.12 Hz, 3 H), 1.48 (dd, J=12.38, 2.54 Hz, 2 H), 1.80-1.96 (m, 3 H), 2.24 (d, J=6.78 Hz, 15 H), 2.39-2.44 (m, 5 H), 2.44-2.65 (m, 1 H), 4.15 (q, J=7.23 Hz, 2 H), 7.15-7.21 (m, 2 H), 7.23-7.32 (m, 2 H); MS (DCI) m/z 412 (M+NH$_4$)$^+$.

Example 77E ethyl 2-(4-(4-(4,4,5,5-tetramethyl-1,3,2-dioxaborolan-2-yl)phenyl)cyclohexyl)acetate Tris(dibenzylideneacetone)dipalladium(0) (60 mg, 0.131 mmol) and tricyclohexylphosphine (1M, 313 mL, 0.313 mmol) were mixed in 2 mL of dioxane under nitrogen for 30 min. Then 4,4,4',4',5,5,5',5'-octamethyl-2,2'-bi(1,3,2-dioxaborolane) (738 mg, 3.13 mmol), potassium acetate (385 mg, 3.92 mmol) and the product from Example 77D (1.03 g, 2.61 mmol) were added. The mixture was heated to reflux and stirred overnight. The mixture was then cooled to room temperature and diluted with 75% ethyl acetate/hexanes and filtered. The filtrate was concentrated, and then the resulting residue was purified by flash chromatography (3% ethyl acetate/hexanes) to give the title compound. The product was contaminated with 10-15% of unreacted triflate starting material. MS (DCI) m/z 390 (M+NH$_4$)$^+$.

Example 77F

[4-(4'-hydroxy-1,1'-biphenyl-4-yl)cyclohexyl]acetic acid

The product from Example 77E (65 mg, 0.157 mmol), [1,1'-bis(diphenylphosphino)ferrocene]dichloropalladium (II) (9.9 mg, 0.0122 mmol), 4-iodophenol (38.3 mg, 0.174 mmol) and Na$_2$CO$_3$ (40.6 mg, 0.383 mmol) were mixed in 1.5 mL of 7:2:3/1,2-dimethoxyethane:ethanol:1120 in a microwave reaction tube. The mixture was heated to 100° C. and stirred for 20 min. The mixture was cooled to room temperature and then dissolved in approximately 2 mL of 1:1/DMSO: tetrahydrofuran. The mixture was filtered and the filtrate was purified by reverse-phase HPLC. This isolated product was then hydrolyzed according to the procedure for Example 1H to give the title compound. $^1$H NMR (500 MHz, DMSO-d$_6$) δ ppm 1.06-1.19 (m, 4 H), 1.38-1.53 (m, 2 H), 1.55-1.69 (m, 2 H), 1.68-1.87 (m, 3 H), 2.15 (d, J=7.02 Hz, 2 H), 2.34-2.48 (m, 1 H), 6.82 (d, J=8.54 Hz, 2 H), 7.21-7.34 (m, 2 H), 7.39-7.54 (m, 2 H), 9.47 (s, 1 H), 12.02 (s, 1 H); MS (ESI) m/z 309 (M−H)$^-$.

Example 78

(4-{4'-[({[2-fluoro-5-(trifluoromethyl)phenyl] amino}carbonyl)amino]-1,1'-biphenyl-4-yl}cyclohexyl)acetic acid The title compound was prepared according to the procedure as described in Example 77F. substituting 1-(2-fluoro-5-(trifluoromethyl)phenyl)-3-(4-iodophenyl)urea for iodophenol, followed by hydrolysis in a similar manner to that described in Example 1H. $^1$H NMR (300 MHz, CF$_3$COOD) δ ppm 1.29-1.48 (m, 3 H), 1.49-1.81 (m, 2 H), 1.80-1.98 (m, 2 H), 2.11 (m Hz, 3 H), 2.46-2.70 (m, 1 H), 2.79 and 2.69 (d, J=7.81 Hz, 1 H), 7.27-7.57 (m, 4 H), 7.58-7.73 (m, 2 H), 7.81 (dd, J=8.54, 2.20 Hz, 2 H), 8.09 (d, J=7.32 Hz, 1 H); MS (ESI) m/z 515 (M+H)$^+$.

Example 79

[4-(4-pyrazin-2-ylphenyl)cyclohexyl]acetic acid

The title compound was prepared according to the procedure as described in Example 77F. substituting 2-chloropyrazine for iodophenol. $^1$H NMR (500 MHz, DMSO-d$_6$) δ ppm 1.06-1.23 (m, 2 H), 1.44-1.57 (m, 2 H), 1.59-1.90 (m, 5 H), 2.16 (d, J=7.02 Hz, 2 H), 2.52-2.60 (m, 1 H), 7.40 (d, J=8.24 Hz, 2 H), 8.05 (d, J=8.24 Hz, 2 H), 8.58 (d, J=2.44 Hz, 1 H), 8.69 (dd, J=2.59, 1.68 Hz, 1 H), 9.22 (d, J=1.53 Hz, 1 H), 12.03 (s, 1 H); MS (ESI) m/z 297 (M+H)$^+$.

Example 80

Trans {4-[4-(7-amino-3-phenylpyrazolo[1,5-a]pyrimidin-6-yl)phenyl]cyclohexyl}acetic acid

Example 80A

Trans ethyl 2-4-(4-(hydroxymethyl)phenyl)cyclohexyl)acetate

Sodium borohydride (2.2 g, 58.32 mmol) was added in one portion to a stirred and cooled (0° C.) solution of Example 1C (5.99 g, 19.44 mmol) in dry tetrahydrofuran (100 mL). The resulting solution was allowed to warm to room temperature and stirred for another 12 hours. The solution was cooled (0° C.) and quenched with 0.1 N hydrochloric acid. The mixture was diluted with ether and water and the phases were separated. The organic phase was washed with brine and dried over magnesium sulfate. After filtration, the solvent was evaporated and the residue was purified by silica gel chromatography using 30% ethyl acetate in hexanes to provide the title compound as a colorless oil.

Example 80B

Trans ethyl 2-4-(4-(cyanomethyl)phenyl)cyclohexyl)acetate

Step One
Carbon tetrabromide (5.3 g, 15.86 mmol) in dichloromethane (10 mL) was added dropwise to a stirred and cooled (0° C.) solution of Example 80A (3.37 g, 12.20 mmol) and triphenylphosphine (4.2 g, 15.86 mmol) in dichloromethane (60 mL). The resulting solution was stirred for another 2 hours before the solvent was evaporated. Ether was added to precipitate out triphenylphosphine oxide and the mixture was filtered through a pad of silica gel using ether to wash. The filtrate was concentrated and the product was used in Step 2 without further purification.
Step Two
Sodium cyanide (3.50 g, 69.65 mmol) was added in one portion to a stirred solution of the product from Step 1 (12.20 mmol) in dry DMSO (30 mL). The resulting dark brown solution was heated (50° C.) for 5 hours before it was cooled and partitioned with ether and water. The organic layer was washed with water and brine, dried (magnesium sulfate) and filtered. The residue was purified by silica gel chromatography using 30% ethyl acetate in hexanes to provide the title compound as a colorless oil, which solidified upon standing.

Example 80C

Trans ethyl 2-(-4-(4-((Z)-1-cyano-2-(dimethylamino) vinyl)phenyl)cyclohexyl)acetate 1-tert-butoxy-N,N,N',N'-tetramethylmethanediamine (2.55 mL, 12.34 mmol) was added dropwise to a stirred and heated (120° C.) solution of Example 80B (1.76 g, 6.17 mmol) in dry toluene (30 mL). The resulting solution was heated for another 3 hours before it was concentrated. The residue was purified by silica gel chromatography using 50% ethyl acetate in hexanes to provide the title compound as a light yellow oil, which solidified upon standing.

Example 80D

Trans {4-[4-(7-amino-3-phenylpyrazolo[1,5-a]pyrimidin-6-yl)phenyl]cyclohexyl}acetic acid Example 80C (40 mg, 0.117 mmol) and 4-phenyl-1H-pyrazol-5-amine (56 mg, 0.351 mmol) were heated (Personal Chemistry Microwave, 150° C., 20 minutes) in toluene (1 mL) and acetic acid (0.5 mL). The solvent was evaporated and the residue was dissolved in methanol (3 mL). Sodium hydroxide (1 mL, 1 N) was added and the solution was heated (50° C.) for 1 hour. The solvent was evaporated and the residue was purified by preparative reverse phase high pressure liquid chromatography (RP-HPLC) using a Zorbax SB-C18 7M 21.2×250 mm column with UV detection analyzed at 220 and 254 nM, and eluted with a solvent system containing component A (water with 0.1% trifluoroacetic acid) and component B (acetonitrile with 0.1% trifluoroacetic acid) with gradient of 5-95% of component B over 30 minutes at 15 mL/minute unless otherwise noted. After evaporation, the title compound was isolated as a solid. $^1$H NMR (300 MHz, methanol-d$_4$) δ ppm 1.02-1.41 (m, 2 H), 1.13-1.32 (m, 2 H), 1.45-1.73 (m, 2 H), 1.73-2.09 (m, J=12.21 Hz, 5 H), 2.24 (d, J=7.12 Hz, 1 H), 2.60 (t, J=12.21 Hz, 1 H), 2.73 (s, 3 H), 7.25-7.30 (m, 1 H), 7.41-7.50 (m, 6 H), 7.88 (s, 1 H), 7.91 (s, 1 H), 8.15 (s, 1 H), 8.46 (s, 1 H), MS (ESI) m/z 247.3 [M+H].

Example 81

{4-[4-(7-amino-5-methyl[1,2,4]triazolo[1,5-a]pyrimidin-6-yl)phenyl]cyclohexyl}acetic acid Example 81A ethyl {4-[4-(7-amino-5-methyl[1,2,4]triazolo[1,5-a]pyrimidin-6-yl)phenyl]cyclohexyl}acetate 6-Iodo-5-methyl-[1,2,4]triazolo[1,5-a]pyrimidin-7-amine (205 mg, 0.745 mmol), Example 77E (308 mg, 0.745 mmol). [1.1'-bis(diphenylphosphino)ferrocene]dichloropalladium (II) (128 mg, 0.149 mmol), sodium carbonate (174 mg, 1.64 mL), and 1,2-dimethoxyethane:ethanol:N,N-dimethylformamide:water (1.75:0.5:0.75:0.3 mL) were mixed in a microwave reaction tube and heated to 110° C. (Personal Chemistry Microwave) for 15 minutes. The mixture was filtered through a plug of Celite and the filtrate was purified by reverse-phase HPLC (using a Zorbax SB-C18 7M 21.2×250 mm column with UV detection analyzed at 220 and 254 nM, and eluted with a solvent system containing component A (water with 0.1% trifluoroacetic acid) and component B (acetonitrile with 0.1% trifluoroacetic acid) with gradient of 5-95% of component B over 30 minutes at 15 mL/minute) to provide the title compound.

Example 81B

{4-[4-(7-amino-5-methyl[1,2,4]triazolo[1,5-a]pyrimidin-6-yl)phenyl]cyclohexyl}acetic acid Example 81A was dissolved in methanol. Sodium hydroxide (excess, 1 N) was added and the solution was heated (50° C.) for 1 hour. The solvent was evaporated and the residue was purified by preparative reverse phase high pressure liquid chromatography (RP-HPLC) using a Zorbax SB-C18 7M 21.2×250 mm column with UV detection analyzed at 220 and 254 mM, and eluted with a solvent system containing component A (water with 0.1% trifluoroacetic acid) and component B (acetonitrile with 0.1% trifluoroacetic acid) with gradient of 5-95% of component B over 30 minutes at 15 mL/minute unless otherwise noted. After evaporation, the title compound was isolated as a ~7:3/trans:cis mixture. $^1$H NMR (400 MHz, methanol-d$_4$) δ ppm 8.53 (s, 1 H), 7.43-7.53 (m, 2 H), 7.27-7.34 (m, 2 H), 2.60-2.65 (m, 1 H), 2.48 and 2.25 (d, J=7.1 Hz, 2H), 2.30 (s, 3H), 1.96-1.98 (m, 3.3 H), 1.76-1.79 (m, 2.3 H), 1.58-1.64 (m, 1.7H), 1.20-1.28 (m, 1.7H), MS (ESI) m/z 366 (M+H)$^+$.

Example 82

Trans (4-{4-[7-amino-2-(methylthio)[1,2,4]triazolo[1,5-a]pyrimidin-6-yl]phenyl}cyclohexyl)acetic acid Example 80C (40 mg, 0.117 mmol) and 3-(methylthio)-1H-1,2,4-triazol-5-amine (50 mg, 0.35 mmol) were heated (Personal Chemistry Microwave 150° C., 20 minutes) in toluene (1 mL) and acetic acid (0.5 mL). The solvent vas evaporated and the residue was dissolved in methanol (3 mL). Sodium hydroxide (1 mL, 1 N) was added and the solution was heated (50° C.) for one hour. The solvent was evaporated and the residue was purified by preparative reverse phase high pressure liquid chromatography (RP-HPLC) using a Zorbax SB-C18 7M 21.2×250 mm column with UV detection analyzed at 220 and 254 nM, and eluted with a solvent system containing component A (water with 0.1% trifluoroacetic acid) and component B (acetonitrile with 0.1% trifluoroacetic acid) with gradient of 5-95% of component B over 30 minutes at 15 mL/minute unless otherwise noted. After evaporation the title compound was isolated as a solid. $^1$H NMR (300 MHz, methanol-$d_4$) δ ppm 1.16-1.31 (m, 2 H), 1.71-1.81 (m, J=3.73 Hz, 2 H), 1.89-2.01 (m, J=11.87 Hz, 4 H), 2.20-2.28 (m, 2 H), 2.44-2.50 (m, 2 H), 2.68-2.71 (m, 1 H), 2.73 (s, 3 H), 7.31-7.41 (m, 3 H), 7.33-7.41 (m, 1 H), 7.44 (d, J=6.78 Hz, 2 H), 8.18 (d, J=1.70 Hz, 1 H), MS (ESI) m/z 278.2 [M+H].

Example 83

Trans {4-[4-(7-amino-2-thien-2-ylpyrazolo[1,5-a]pyrimidin-6-yl)phenyl]cyclohexyl}acetic acid Example 80C (40 mg, 0.117 mmol) and 3-(thiophen-2-yl)-1H-pyrazol-5-amine (60 mg, 0.35 mmol) were heated (Personal Chemistry Microwave 150° C. 20 minutes) in toluene (1 mL) and acetic acid (0.5 mL). The solvent was then evaporated and the residue was dissolved in methanol (3 mL), sodium hydroxide (1 mL, 1 N) was added and the solution was heated (50° C.) for one hour. The solvent was evaporated and the residue was purified by preparative reverse phase high pressure liquid chromatography (RP-HPLC) using a Zorbax SB-C18 7M 21.2×250 mm column with UV detection analyzed at 220 and 254 nM, and eluted with a solvent system containing component A (water with 0.1% trifluoroacetic acid) and component B (acetonitrile with 0.1% trifluoroacetic acid) with gradient of 5-95% of component B over 30 minutes at 15 mL/min unless otherwise noted. Alter evaporation the title compound was isolated as a solid. $^1$H NMR (300 MHz, methanol-$d_4$) δ ppm 1.09-1.38 (m, 2 H), 1.41-1.73 (m, 2 H), 1.78-2.05 (m, J=12.21 Hz, 5 H), 2.25 (d, J=6.78 Hz, 2 H), 2.48-2.69 (m, 1 H), 7.20 (dd, J=5.09, 3.73 Hz, 1 H), 7.36-7.53 (m, 5 H), 7.61 (dd, J=5.09, 1.02 Hz, 1 H), 7.77 (dd, J=3.73, 1.02 Hz, 1 H), 8.16 (s, 1 H), MS (ESI) m/z 433.3 [M+H].

Example 84

Trans {4-[4-(7-amino-2-cyclopropylpyrazolo[1,5-a]pyrimidin-6-yl)phenyl]cyclohexyl}acetic acid Example 80C (40 mg, 0.117 mmol) and 3-cyclopropyl-1H-pyrazol-5-amine (42 mg, 0.35 mmol) were heated (Personal Chemistry Microwave 150° C., 20 minutes) in toluene (1 mL) and acetic acid (0.5 mL). The solvent was then evaporated and the residue dissolved in methanol (3 mL). Sodium hydroxide (1 mL, 1 N) was added and the solution was heated (50° C.) for one hour. The solvent was evaporated and the residue was purified by preparative reverse phase high pressure liquid chromatography (RP-HPLC) using a Zorbax SB-C18 7M 21.2×250 mm column with UV detection analyzed at 220 and 254 nM, and eluted with a solvent system containing component A (water with 0.1% trifluoroacetic acid) and component B (acetonitrile with 0.1% trifluoroacetic acid) with gradient of 5-95% of component B over 30 minutes at 15 mL/minute unless otherwise noted. After evaporation the title compound was isolated as a solid. $^1$H NMR (300 MHz, methanol-$d_4$) δ ppm 0.96-1.09 (m, 2 H), 1.10-1.19 (m, 2 H), 1.17-1.38 (m, 2 H), 1.49-1.69 (m, 2 H), 1.70-2.05 (m, 5 H), 2.22 (none, 1 H), 2.09-2.35 (m, 3 H), 2.49-2.71 (m, 1 H), 6.28 (s, 1 H), 7.27-7.61 (m, 4 H), 8.09 (s, 1 H), MS (ESI) m/z 391.3 [M+H].

Example 85

Trans {4-[4-(7-amino[1,2,4]triazolo[1,5-a]pyrimidin-6-yl)phenyl]cyclohexyl}acetic acid Example 80C (57 mg, 0.167 mmol) and 1H-1,2,4-triazol-5-amine (42 mg, 0.50 mmol) were heated (Personal Chemistry Microwave 150° C. 20 minutes) in toluene (1 mL) and acetic acid (0.5 mL). The solvent was evaporated and the residue was dissolved in methanol (3 mL). Sodium hydroxide (1 mL, 1 N) was added and the solution was heated (50° C.) for one hour. The solvent was evaporated and the residue was purified by preparative reverse phase high pressure liquid chromatography (RP-HPLC) using a Zorbax SB-C18 7M 21.2×250 mm column with UV detection analyzed at 220 and 254 nM, and eluted with a solvent system containing component A (water with 0.1% trifluoroacetic acid) and component B (acetonitrile with 0.1% trifluoroacetic acid) with gradient of 5-95% of component B over 30 minutes at 15 mL/minute unless otherwise noted. After evaporation the title compound was isolated as a solid. $^1$H NMR (300 MHz, methanol-$d_4$) δ ppm 1.02-1.38 (m, 2 H) 1.50-1.72 (m, 2 H) 1.79-2.08 (m, 7 H) 2.25 (d, J=7.12 Hz, 2 H) 2.51-2.80 (m, J=23.57, 11.02 Hz, 1 H), 7.45 (s, 2 H), 8.34 (s, 1 H), 8.72 (s, 1 H). MS (ESI) m/z 352.2 [M+H].

Example 86

Trans ethyl {4-[4-(5-aminoimidazo[1,2-a]pyrimidin-6-yl)phenyl]cyclohexyl}acetate Example 80C (57 mg, 0.167 mmol), 2-aminoimidazole sulfate (130 mg, 0.50 mmol), and sodium acetate (0.2 g) were heated (Personal Chemistry Microwave 150° C., 20 minutes) in N,N-dimethylformamide (2 mL). The solvent was evaporated and the residue was purified by preparative reverse phase high pressure liquid chromatography (RP-HPLC) using a Zorbax SB-C18 7M 21.2×250 mm column with UV detection analyzed at 220 and 254 nM, and eluted with a solvent system containing component A (water with 0.1% trifluoroacetic acid) and component B (acetonitrile with 0.1% trifluoroacetic acid) with gradient of 5-95% of component B over 30 minutes at 15 mL/minute unless otherwise noted. After evaporation the title compound was isolated as a solid. $^1$H NMR (300 MHz, methanol-$d_4$) δ ppm 1.09-1.37 (m, 5 H), 1.48-1.70 (m, 2 H), 1.78-2.05 (m, 7 H), 2.27 (d, J=6.78 Hz, 2 H), 2.51-2.69 (m, J=12.21, 12.21 Hz, 1 H), 4.14 (q, J=7.12 Hz, 2 H), 7.43 (s, 4 H), 7.93 (d, J=2.71 Hz, 1 H), 8.07 (d, J=2.71 Hz, 1 H), 8.31 (s, 1 H). MS (ESI) m/z 379.2 [M+H].

Example 87

Trans (4-{4-[7-amino-2-(4-fluorophenyl)pyrazolo[1,5-a]pyrimidin-6-yl]phenyl}cyclohexyl)acetic acid Example 80C (57 mg, 0.167 mmol) and 3-(4-fluorophenyl)-1H-pyrazol-5-amine (90 mg, 0.50 mmol) were heated (Personal Chemistry Microwave, 150° C. 20 minutes) in toluene (1 mL) and acetic acid (0.5 mL). The solvent was then evaporated and the residue dissolved in methanol (3 mL). Sodium hydroxide (1 mL, 1 N) was added and the solution was heated (50° C.) for one hour. The solvent was evaporated and the residue was purified by preparative reverse phase high pressure liquid chromatography (RP-HPLC) using a Zorbax SB-C18 7M 21.2×250 mm column with UV detection analyzed at 220 and 254 nM, and eluted with a solvent system containing component A (water with 0.1% trifluoroacetic acid) and component B (acetonitrile with 0.1% trifluoroacetic acid) with gradient of 5-95% of component B over 30 minutes at 15 mL/minute unless otherwise noted. After evaporation the title compound was isolated as a solid. $^1$H NMR (300 MHz, methanol-$d_4$) δ ppm 1.03-1.37 (m, 2 H), 1.48-1.72 (m, 2 H), 1.70-2.06 (m, 7 H), 2.25 (d, J=7.12 Hz, 2 H), 2.53-2.74 (m, J=11.70, 11.70 Hz, 1 H), 6.93 (s, 1 H), 7.25 (t, J=8.82 Hz, 2 H), 7.36-7.58 (m, 4 H), 8.01-8.27 (m, 4 H). MS (ESI) m/z 445.3 [M+H].

Example 88

Trans {4-[4-(7-amino-2-methylpyrazolo[1,5-a]pyrimidin-6-yl)phenyl]cyclohexyl}acetic acid Example 80C (57 mg, 0.167 mmol) and 3-methyl-1H-pyrazol-5-amine (50 mg, 0.50 mmol) were heated (Personal Chemistry Microwave 150° C., 20 minutes) in toluene (1 mL) and acetic acid (0.5 mL). The solvent was then evaporated and the residue dissolved in methanol (3 mL). Sodium hydroxide (1 mL, 1 N) was added and the solution was heated (50° C.) for one hour. The solvent was evaporated and the residue was purified by preparative reverse phase high pressure liquid chromatography (RP-HPLC) using a Zorbax SB-C18 7M 21.2×250 mm column with UV detection analyzed at 220 and 254 nM, and eluted with a solvent system containing component A (water with 0.1% trifluoroacetic acid) and component B (acetonitrile with 0.1% trifluoroacetic acid) with gradient of 5-95% of component B over 30 minutes at 15 mL/minute unless otherwise noted. After evaporation the title compound was isolated as a solid. $^1$H NMR (300 MHz, methanol-$d_4$) δ ppm 1.04-1.36 (m, 2 H), 1.49-1.69 (m, J=12.66, 12.66, 12.66 Hz, 2H), 1.68-2.08 (m, 7 H), 2.24 (d, J=7.12 Hz, 2 H), 2.53 (s, 3 H), 2.55-2.77 (m, 1 H), 6.40 (s, 1H), 7.12-7.65 (m, 4 H), 8.12 (s, 1 H). MS (ESI) m/z 365.2 [M+H].

Example 89

Trans {4-[4-(7-amino-2-hydroxypyrazolo[1,5-a]pyrimidin-6-yl)phenyl]cyclohexyl}acetic acid Example 80C (57 mg, 0.167 mmol) and 5-amino-1H-pyrazol-3-ol (50 mg, 0.50 mmol) were heated (Personal Chemistry Microwave 150° C. 20 minutes) in toluene (1 mL) and acetic acid (0.5 mL). The solvent was then evaporated and the residue dissolved in methanol (3 mL). Sodium hydroxide (1 mL, 1 N) was added and the solution was heated (50° C.) for one hour. The solvent was evaporated and the residue was purified by preparative reverse phase high pressure liquid chromatography (RP-HPLC) using a Zorbax SB-C18 7M 21.2×250 mm column with UV detection analyzed at 220 and 254 nM, and eluted with a solvent system containing component A (water with 0.1% trifluoroacetic acid) and component B (acetonitrile with 0.1% trifluoroacetic acid) with gradient of 5-95% of component B over 30 minutes at 15 mL/minute unless otherwise noted. After evaporation the title compound was isolated as a solid. $^1$H NMR (300 MHz, methanol-$d_4$) δ ppm 1.02-1.41 (m, 2 H), 1.13-1.32 (m, 2 H), 1.45-1.73 (m, 2 H), 1.73-2.09 (m, J=12.21 Hz, 5 H), 2.24 (d, J=7.12 Hz, 1 H), 2.60 (t, J=12.21 Hz, 1 H), 6.52 (d, J=2.03 Hz, 1H), 7.38-7.51 (m, 4 H), 8.22 (s, 1 H). MS (ESI) m/z 367.2 [M+H].

Example 90

Trans 2-{4-[4-(7-aminopyrazolo[1,5-a]pyrimidin-6-yl)phenyl]cyclohexyl}-N-methylacetamide To a dry N,N-dimethylformamide solution (2 mL) of Example 92 (40 mg, 0.114 mmol) and N,N-Diisopropylethylamine (0.05 mL, 0.25 mmol) was added O-(7-azabenzotriazol-1-yl)-N,N,N',N'-tetramethyluronium hexafluorophosphate (56 mg, 0.148 mmol). The resulting solution was stirred for 1 hour before a solution of methylamine (0.5 mL, 2 M in tetrahydrofuran) was added. The resulting solution was stirred for another 1 hour before the solvent was evaporated and the residue was purified by preparative reverse phase high pressure liquid chromatography (RP-HPLC) using a Zorbax SB-C18 7M 21.2×250 mm column with UV detection analyzed at 220 and 254 nM, and eluted with a solvent system containing component A (water with 0.1% trifluoroacetic acid) and component B (acetonitrile with 0.1% trifluoroacetic acid) with gradient of 5-95% of component B over 30 minutes at 15 mL/minute unless otherwise noted. After evaporation the title compound was isolated as a solid. $^1$H NMR (300 MHz, methanol-$d_4$) δ ppm 1.02-1.41 (m, 2 H), 1.13-1.32 (m, 2 H), 1.45-1.73 (m, 2 H), 1.73-2.09 (m, J=12.21 Hz, 5 H), 2.24 (d, J=7.12 Hz, 1 H), 2.60 (t, J=12.21 Hz, 1 H), 2.73 (s, 3 H), 6.52 (d, J=2.03 Hz, 1 H), 7.38-7.51 (m, 4 H), 8.16 (s, 1 H), 8.20 (d, J=2.37 Hz, 1 H), MS (ESI) m/z 350.2 [M+H].

Example 91

Trans 2-{4-[4-(7-aminopyrazolo[1,5-a]pyrimidin-6-yl)phenyl]cyclohexyl}acetamide

To a dry N,N-dimethylformamide solution (2 mL) of Example 92 (40 mg, 0.114 mmol) and N,N-Diisopropylethylamine (0.05 mL, 0.25 mmol) was added O-(7-azabenzotriazol-1-yl)-N,N,N',N'-tetramethyluronium hexafluorophosphate (56 mg, 0.148 mmol). The resulting solution was stirred for 1 hour before a solution of ammonia (0.5 mL, 2 M in isopropanol) was added. The resulting solution was stirred for another 1 hour before the solvent was evaporated and the residue was purified by preparative reverse phase high pressure liquid chromatography (RP-HPLC) using a Zorbax SB-C18 7M 21.2×250 mm column with UV detection analyzed at 220 and 254 nM, and eluted with a solvent system containing component A (water with 0.1% trifluoroacetic acid) and component B (acetonitrile with 0.1% trifluoroacetic acid) with gradient of 5-95% of component B over 30 minutes at 15 mL/minute unless otherwise noted. After evaporation the title compound was isolated as a solid. $^1$H NMR (300 MHz, methanol-$d_4$) δ ppm 1.02-1.41 (m, 2 H), 1.13-1.32 (m, 2 H), 1.45-1.73 (m, 2 H), 1.73-2.09 (m, J=12.21 Hz, 5 H), 2.24 (d, J=7.12 Hz, 1 H), 2.60 (t, J=12.21 Hz, 1 H), 6.52 (d, J=2.03 Hz, 1 H), 7.38-7.51 (m, 4H), 8.16 (s, 1 H), 8.20 (d, J=2.37 Hz, 1 H), MS (ESI) m/z 350.2 [M+H].

Example 92

Trans {4-[4-(7-aminopyrazolo[1,5-a]pyrimidin-6-yl)phenyl]cyclohexyl}acetic acid

Example 80C (57 mg, 0.167 mmol) and 1H-pyrazol-5-amine (42 mg, 0.50 mmol) were heated (Personal Chemistry Microwave 150° C. 20 minutes) in toluene (1 mL) and acetic acid (0.5 mL). The solvent was then evaporated and the residue dissolved in methanol (3 mL). Sodium hydroxide (1 mL, 1 N) was added and the solution was heated (50° C.) for one hour. The solvent was evaporated and the residue was purified by preparative reverse phase high pressure liquid chromatography (RP-HPLC) using a Zorbax SB-C18 7M 21.2×250 mm column with UV detection analyzed at 220 and 254 nM, and eluted with a solvent system containing component A (water with 0.1% trifluoroacetic acid) and component B (acetonitrile with 0.1% trifluoroacetic acid) with gradient of 5-95% of component B over 30 minutes at 15 mL/minute unless otherwise noted. After evaporation the title compound was isolated as a solid. $^1$H NMR (300 MHz, methanol-$d_4$) δ ppm 1.02-1.41 (m 2 H), 1.13-1.32 (m, 2 H), 1.45-1.73 (m, 2 H), 1.73-2.09 (m, J=12.21 Hz, 5 H), 2.24 (d, J=7.12 Hz, 1 H), 2.60 (t, J=12.21 Hz, 1 H), 6.52 (d, J=2.03 Hz, 1H), 7.38-7.51 (m, 4 H), 8.16 (s, 1 H), 8.20 (d, J=2.37 Hz, 1 H). MS (ESI) m/z 351.2 [M+H].

Example 93

{4-[5-(5-{[2-(trifluoromethoxy)benzyl]oxy}-1H-pyrazol-3-yl)pyridin-2-yl]cyclohexyl}acetic acid Example 93A methyl 6-(1,4-dioxaspiro[4,5]dec-7-en-8-yl)nicotinate Methyl 6-bromonicotinate (2.11 g, 9.78 mmol), 1,4-dioxaspiro[4,5]dec-7-en-8-ylboronic acid (2 g, 10.86 mmol), palladium(II) acetate (109 mg, 0.48 mmol), dicyclohexyl(2',6'-dimethoxybiphenyl-2-yl)phosphine (0.40 g, 0.97 mmol) and potassium phosphate (6.2 g, 29.1 mmol) were placed in a Schlenk tube and the tube was placed under vacuum and filled with argon. Dioxane (30 mL) and water (4 mL) were added and the tube was heated (80° C.) overnight. The mixture was partitioned with ether and water and the organic phase was washed with brine, dried (magnesium sulfate), filtered and evaporated. The residue was purified by silica gel chromatography using 30% ethyl acetate in hexanes to provide the title compound as a slightly yellow oil, which solidified upon standing.

Example 93B methyl 6-(1,4-dioxaspiro[4,5]decan-8-yl)nicotinate

Palladium hydroxide on carbon (1 g, 20 wt % Pd) was added to a solution of Example 93A (2.66 g, 9.66 mmol) in methanol (40 mL) and ethyl acetate (10 mL). The mixture was placed under vacuum and filled with hydrogen (balloon) and allowed to stir for 3 hours before it was filtered through a pad of Celite using methanol to rinse. The solvent was evaporated and the product was dissolved in dichloromethane and dried over $Na_2SO_4$. After filtration and concentration, the title compound was isolated as a slightly yellow solid and used in the following step without further purification.

Example 93C tert-butyl 3-(6-(1,4-dioxaspiro[4,5]decan-8-yl)pyridin-3-yl)-3-oxopropanoate Tert-butyl acetate (2.40 mL, 17.82 mmol) was added to a stirred and cooled (−78° C.) solution of lithium hexamethyldisilazide (17.8 mL, 1 M in tetrahydrofuran) in dry tetrahydrofuran (10 mL). After 30 minutes of stirring at −78° C., a solution of Example 93B (2.47 g, 8.9 mmol) in tetrahydrofuran was added dropwise into the solution. The resulting mixture was stirred for another hour before it was quenched with ammonium chloride and allowed to warm to room temperature. The mixture was partitioned with ether and water and the phases were separated. The organic phase was washed with brine, dried (magnesium sulfate), filtered and concentrated. The residue was purified by silica gel chromatography using 30% ethyl acetate in hexanes to provide the title compound as a yellow oil.

Example 93D 3-(6-(1,4-dioxaspiro[4,5]decan-8-yl)pyridin-3-yl)-1H-pyrazol-5-ol

Hydrazine hydrate (5 mL) was added to a solution of Example 93C (1.07 g, 2.96 mmol) in dioxane (10 mL). The resulting solution was refluxed for 3 hours before it was cooled and partitioned with tetrahydrofuran and brine. The aqueous phase was acidified with 6 N hydrochloric acid to pH 2 and extracted repeatedly with a tetrahydrofuran/ethyl acetate mixture. The combined organic phases were dried (magnesium sulfate), filtered, and concentrated. The crude product was recrystallized from ethyl acetate and hexane to provide a light brown solid.

Example 93E 2-(1,4-dioxaspiro[4,5]decan-8-yl)-5-(5-(2-(trifluoromethoxy)benzyloxy)-1H-pyrazol-3-yl)pyridine 1-(bromomethyl)-2-(trifluoromethoxy)benzene (0.4 g, 1.57 mmol) was added dropwise to a stirred solution of Example 93D (0.43 g, 1.42 mmol) and potassium carbonate (0.16 g, 1.13 mmol) in refluxing dry acetone (7 mL). The resulting solution was heated (50° C.) for another 1 hour before the solvent was evaporated and the residue was partitioned using brine and ethyl acetate. The organic phase was dried (magnesium sulfate), filtered, and concentrated. The residue was purified by silica gel chromatography using 0 to 100% ethyl acetate in hexanes to provide the title compound as a yellow oil.

Example 93F 4-(5-(5-(2-(trifluoromethoxy)benzyloxy)-1H-pyrazol-3-yl)pyridin-2-yl)cyclohexanone Indium chloride (0.11 g, 0.536 mmol) was added to a solution of Example 93E (0.255 g, 0.536 mmol) in methanol (3 ml) and water (3 mL). The resulting solution was heated (85° C.) for 5 hours before the methanol was evaporated. The residue was partitioned with ethyl acetate and water, and the organic phase was washed with brine, dried (magnesium sulfate), filtered, and concentrated. The crude product was used in the following step without further purification.

Example 93G ethyl 2-(4-(5-(5-(2-(trifluoromethoxy)benzyloxy)-1H-pyrazol-3-yl)pyridin-2-yl)cyclohexylidene)acetate Methyl 2-(dimethoxyphosphoryl)acetate (0.76 ml, 3.77 mmol) was added dropwise to a stirred and cooled (0° C.) suspension of sodium hydride (0.15 g, 3.76 mmol) in dry N,N-dimethylformamide (10 mL). After 30 minutes of stirring at room temperature, a N,N-dimethylformamide solution of Example 93F (0.748 g, 1.71 mmol) was added to 0° C. After the addition, the solution was allowed to warm to room temperature and stir overnight. The reaction was quenched with saturated ammonium chloride solution and extracted with ethyl acetate. The combined organic phases were washed with brine, dried (magnesium sulfate), filtered, and concentrated. The residue was purified by silica gel chroma-

Example 93H

{4-[5-(5-{[2-(trifluoromethoxy)benzyl]oxy}-1H-pyrazol-3-yl)pyridin-2-yl]cyclohexyl}acetic acid Example 93G (0.439 g, 0.87 mmol) was stirred in the presence of palladium hydroxide on carbon (0.1 g, 20 wt % Pd) and hydrogen (balloon) in methanol (10 mL) for 5 hours. The mixture was filtered, concentrated, and the residue dissolved in methanol (10 mL) and 1 N sodium hydroxide (3 mL) and stirred at 50° C. for 2 hours. The methanol was evaporated and the mixture was acidified (pH 2) and extracted with ethyl acetate. The combined organic phases were dried (magnesium sulfate), filtered and evaporated. The residue was purified by silica gel chromatography using 0 to 15% methanol in dichloromethane to provide the title compound as an oil. $^1$H NMR (500 MHz, methanol-$d_4$) δ ppm 1.18-1.37 (m, 2 H), 1.60-2.14 (m, 8 H), 2.22-2.29 (m, 1 H), 2.28-2.37 (m, 1 H), 2.47 (d, J=7.63 Hz, 1 H), 2.80-3.13 (m, 1 H), 5.31 (s, 2 H), 6.33 (s, 1 H), 7.28-7.52 (m, 5 H), 7.66 (do J=7.63 Hz, 1 H), 7.81 (dd, J=12.66, 8.39 Hz, 1 H). MS (ESI) m/z 476.2 [M+H].

Example 94

Trans {4-[4-(7-amino-5-methylpyrazolo[1,5-a]pyrimidin-6-yl)phenyl]cyclohexyl}acetic acid $^1$H NMR (500 MHz, DMSO-$d_6$) δ ppm 1.10-1.21 (m, 2 H), 1.46-1.59 (m, 2 H), 1.62-1.71 (m, 1 H), 1.72-1.80 (m, 1 H), 1.83-1.92 (m, 3 H), 2.09-2.13 (m, 3 H), 2.14-2.18 (m, 2 H), 2.53-2.58 (m, 1 H), 6.32 (d, J=2.14 Hz, 1 H), 6.88 (s, 2 H), 7.17-7.31 (m, 2 H), 7.33-7.45 (m, 2 H), 8.06 (d, J=2.14 Hz, 1 H); 12.0 (s, 1 H); MS (ESI) m/z 365 [M+H]$^+$.

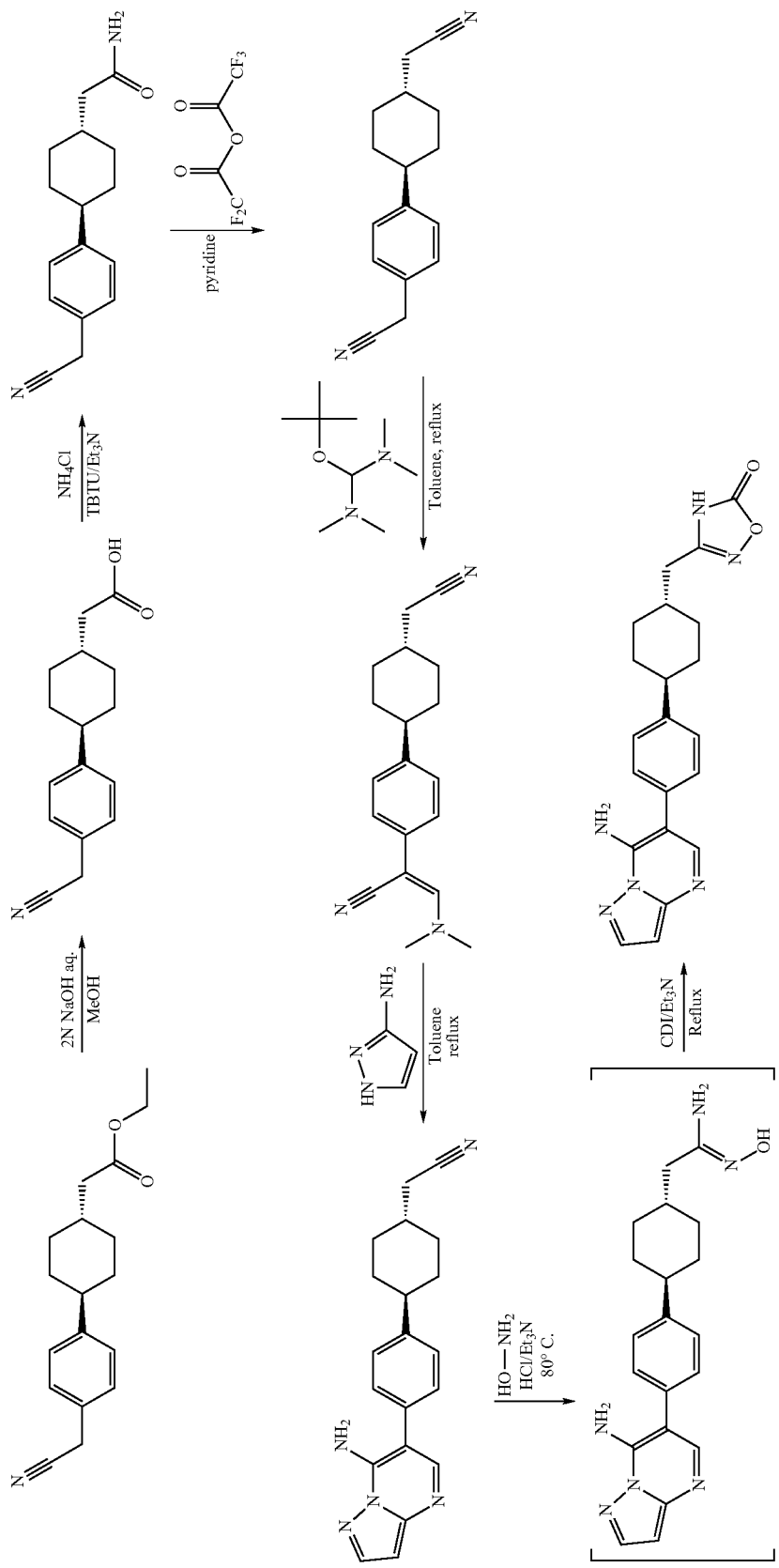

Example 95

Trans 3-({4-[4-(7-aminopyrazolo[1,5-a]pyrimidin-6-yl)phenyl]cyclohexyl}methyl)-1,2,4-oxadiazol-5(4H)-one $^1$H NMR (500 MHz, DMSO-d$_6$) δ ppm 1.12-1.25 (m, 2 H), 1.42-1.56 (m, 2 H), 1.70-1.78 (m, 1 H), 1.79-1.92 (m, 4 H), 2.44 (d, J=7.32 Hz, 2 H), 2.53-2.59 (m, 1 H), 6.44 (d, J=2.44 Hz, 1 H), 7.29-7.49 (m, 6 H), 8.05-8.16 (m, 2 H), 12.0 (s, 1 H); MS (ESI) m/z 391 [M+H]$^+$.

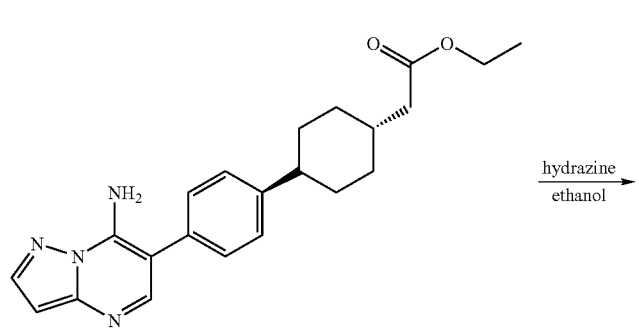
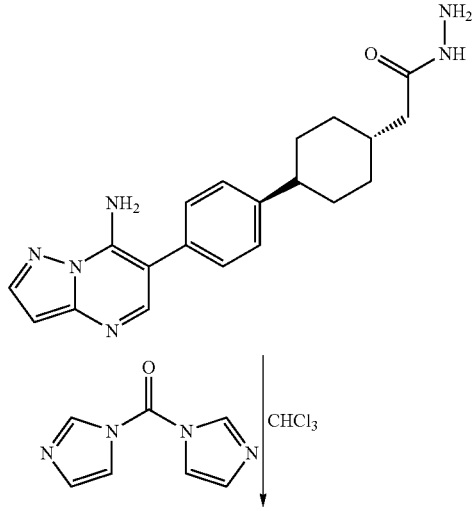
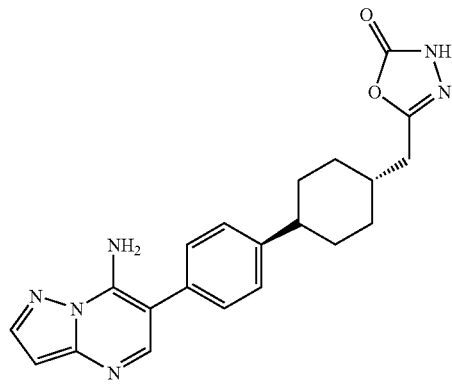

Example 96

Trans 5-({4-[4-(7-aminopyrazolo[1,5-a]pyrimidin-6-yl)phenyl]cyclohexyl}methyl)-1,3,4-oxadiazol-2(3H)-one $^1$H NMR (300 MHz, DMSO-d$_6$) δ ppm 1.06-1.32 (m, 2 H), 1.42-1.60 (m, 2 H), 1.65-1.79 (m, 2 H), 1.77-1.92 (m, 4 H), 2.37-2.47 (m, 1 H), 2.51-2.59 (m, 1 H), 6.44 (d, J=2.37 Hz, 1 H), 7.33-7.48 (m, 6 H), 8.03-8.19 (m, 2 H), 12.1 (s, 1 H); MS (ESI) m/z 391 [M+H]$^+$.

It is understood that the foregoing detailed description and accompanying examples are merely illustrative and are not to be taken as limitations upon the scope of the invention, which is defined solely by the appended claims and their equivalents. Various changes and modifications including, but not limited to, those relating to the chemical structures, substituents, derivatives, intermediates, syntheses, formulations and/or methods of use of the invention, can be made without departing from the spirit and scope thereof.

What we claim is:

1. A compound having formula (I), or a pharmaceutically acceptable salt thereof

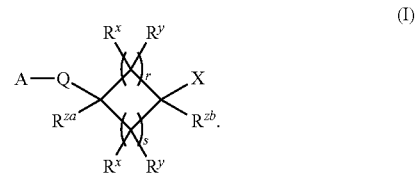

wherein

Q is phenyl or a monocyclic heteroaryl, optionally substituted with 1, 2 or 3 substituents as represented by T, wherein each T is independently alkyl, alkenyl, alkynyl, halogen, —CN, —NO$_2$, —OR$^1$, —OC(O)(R$^2$), —N(R$^w$)(R$^1$), —N(R$^w$)C(O)(R$^1$), —N(R$^w$)—C(O)O(R$^1$), —N(R$^w$)—C(O)N(R$^1$)$_2$, —N(R$^w$)—S(O)$_2$(R$^2$), —C(O)O(R$^1$), —C(O)N(R$^w$)(R$^1$), —C(O)R$^1$, —SR$^1$, —S(O)R$^2$, —S(O)$_2$R$^2$, —S(O)$_2$N(R$^w$)(R$^1$), —(CR$^g$R$^h$)$_t$—CN, —(CR$^g$R$^h$)$_t$—NO$_2$, —(CR$^g$R$^h$)$_t$—OR$^1$, —(CR$^g$R$^h$)$_t$—OC(O)(R$^2$), —(CR$^g$R$^h$)$_t$—N(R$^w$)(R$^1$), —(CR$^g$R$^h$)$_t$—N(R$^w$)C(O)(R$^1$), —(CR$^g$R$^h$)$_t$—N(R$^w$)—C(O)O(R$^1$), —(CR$^g$R$^h$)$_t$—N(R$^w$)—C(O)N(R$^1$)$_2$, —(CR$^g$R$^h$)$_t$—N(R$^w$)—S(O)$_2$(R$^2$), —(CR$^g$R$^h$)$_t$—C(O)O(R$^1$), —(CR$^g$R$^h$)$_t$—C(O)N(R$^w$)(R$^1$), —(CR$^g$R$^h$)$_t$—C(O)R$^1$, —(CR$^g$R$^h$)$_t$—SR$^1$, —(CR$^g$R$^h$)$_t$—S(O)R$^2$, —(CR$^g$R$^h$)$_t$—S(O)$_2$R$^2$, —(CR$^g$R$^h$)$_t$—S(O)$_2$N(R$^w$)(R$^1$) or haloalkyl;

alternatively, two of the adjacent T substituents, together with the carbon atoms to which they are attached, form a monocyclic ring selected from the group consisting of phenyl, heterocycle and heteroaryl, wherein each ring is optionally further substituted with 1, 2 or 3 substituents selected from the group consisting of oxo, alkyl, alkenyl, alkynyl, halogen, —CN, —NO$_2$, —OR$^1$, —OC(O)(R$^2$), —N(R$^w$)(R$^1$), —N(R$^w$)C(O)(R$^1$), —N(R$^w$)—C(O)O(R$^1$), —N(R$^w$)—C(O)N(R$^1$)$_2$, —N(R$^w$)—S(O)$_2$(R$^2$), —C(O)O(R$^1$), —C(O)N(R$^w$)(R$^1$), —C(O)R$^1$, —SR$^1$, —S(O)R$^2$, —S(O)$_2$R$^2$, —S(O)$_2$N(R$^w$)(R$^1$), —(CR$^g$R$^h$)$_t$—CN, —(CR$^g$R$^h$)$_t$—NO$_2$, —(CR$^g$R$^h$)$_t$—OR$^1$, —(CR$^g$R$^h$)$_t$—OC(O)(R$^2$), —(CR$^g$R$^h$)$_t$—N(R$^w$)(R$^1$), —(CR$^g$R$^h$)$_t$—N(R$^w$)C(O)(R$^1$), —(CR$^g$R$^h$)$_t$—N(R$^w$)—C(O)O(R$^1$), —(CR$^g$R$^h$)$_t$—N(R$^w$)—C(O)N(R$^1$)$_2$, —(CR$^g$R$^h$)$_t$—N(R$^w$)—S(O)$_2$(R$^2$), —(CR$^g$R$^h$)$_t$—C(O)O(R$^1$), —(CR$^g$R$^h$)$_t$—C(O)N(R$^w$)(R$^1$), —(CR$^g$R$^h$)$_t$—C(O)R$^1$, —(CR$^g$R$^h$)$_t$—SR$^1$, —(CR$^g$R$^h$)$_t$—S(O)R$^2$, —(CR$^g$R$^h$)$_t$—S(O)$_2$R$^2$, —(CR$^g$R$^h$)$_t$—S(O)$_2$N(R$^w$)(R$^1$), and haloalkyl;

A is formula (a)

(a)

wherein
V$_a$ is N, V$_b$ is C(R$^5$), and V$_c$ is C(R$^6$);
R$^5$ is hydrogen, alkyl, halogen, haloalkyl, —CN, —OR$^b$, —SR$^b$, —S(O)R$^c$, —S(O)$_2$R$^c$, aryl, heteroaryl, cycloalkyl, cycloalkenyl, or heterocycle;
R$^6$ is hydrogen, alkyl, halogen, haloalkyl, aryl, heteroaryl, cycloalkyl, cycloalkenyl, or heterocycle;
R$^7$ is hydrogen, alkyl, halogen, —CN, or haloalkyl;
r and s are independently 1 or 2;
X is X$^1$, —(CR$^k$R$^m$)$_u$—X$^1$, —(CR$^k$R$^m$)$_u$—C(O)—X$^2$, or —C(O)—X$^2$;
X$^1$ at each occurrence is independently heterocycle or heteroaryl;
X$^2$ at each occurrence is independently heteroaryl, heterocycle, —OR$^{11}$, —N(R$^w$)(R$^3$), —N(R$^w$)—(CR″R$^q$)$_w$—C(O)OR$^{11}$, —N(R$^w$)—(CR″R$^q$)$_w$—OR$^{11}$, or —N(R$^w$)—(CR″R$^q$)$_w$—S(O)$_2$R$^{12}$;
R$^{11}$, at each occurrence, is independently hydrogen, alkyl, haloalkyl, arylalkyl, or heteroarylalkyl;
R$^{12}$, at each occurrence, is alkyl, haloalkyl, arylalkyl, or heteroarylalkyl;

wherein the cycloalkenyl, cycloalkyl, heterocycle, heteroaryl, aryl, the aryl moiety of the arylalkyl, and the heteroaryl moiety of the heteroarylalkyl as represented by X$^1$, X$^2$, R$^5$, R$^6$, R$^{11}$ and R$^{12}$, are each optionally further substituted with 1, 2, 3, 4 or 5 substituents selected from the group consisting of alkyl, alkenyl, alkynyl, halogen, oxo, ethylenedioxy, methylenedioxy, —CN, —NO$_2$, —OR$^1$, —OC(O)(R$^2$), —N(R$^w$)(R$^1$), —N(R$^w$)C(O)(R$^1$), —N(R$^w$)—C(O)O(R$^1$), —N(R$^w$)—S(O)$_2$(R$^2$), —C(O)O(R$^1$), —C(O)N(R$^w$)(R$^1$), —C(O)R$^1$, —SR$^1$, —S(O)R$^2$, —S(O)$_2$R$^2$, —S(O)$_2$N(R$^w$)(R$^1$), —(CR$^g$R$^h$)$_v$—CN, —(CR$^g$R$^h$)$_v$—NO$_2$, —(CR$^g$R$^h$)$_v$—OR$^1$, —(CR$^g$R$^h$)$_v$—OC(O)(R$^2$), —(CR$^g$R$^h$)$_v$—N(R$^w$)(R$^1$), —(CR$^g$R$^h$)$_v$—N(R$^w$)C(O)(R$^1$), —(CR$^g$R$^h$)$_v$—N(R$^w$)—C(O)O(R$^1$), —(CR$^g$R$^h$)$_v$—N(R$^w$)—S(O)$_2$(R$^2$), —(CR$^g$R$^h$)$_v$—C(O)O(R$^1$), —(CR$^g$R$^h$)$_v$—C(O)N(R$^w$)(R$^1$), —(CR$^g$R$^h$)$_v$—C(O)R$^1$, —(CR$^g$R$^h$)$_v$—SR$^1$, —(CR$^g$R$^h$)$_v$—S(O)R$^2$, —(CR$^g$R$^h$)$_v$—S(O)$_2$R$^2$—(CR$^g$R$^h$)$_v$—S(O)$_2$N(R$^w$)(R$^1$), and haloalkyl;

t, u, v and w, at each occurrence, are each independently 1, 2, 3, 4, 5, or 6;

R$^3$ is hydrogen, alkyl, haloalkyl, —OH, —S(O)$_2$R$^1$, —C(O)OR$^1$, heterocycle or heteroaryl, wherein the heteroaryl is connected to the nitrogen atom through the ring carbon atom, and the heterocycle and heteroaryl are optionally further substituted with 1 or 2 substituents selected from the group consisting of alkyl, halogen, haloalkyl, —C(O)OR$^1$, —OR$^1$, and —N(R$^w$)(R$^1$);

R$^b$, R$^x$, R$^y$, R$^{za}$, R$^{zb}$, R$^w$, R$^gR^h$, R$^k$, R$^m$, R$^n$, R$^q$ and R$^1$, at each occurrence, are independently hydrogen, alkyl, or haloalkyl; and R$^c$ and R$^2$, at each occurrence, are independently alkyl or haloalkyl.

2. The compound of claim 1 having formula (I), or a pharmaceutically acceptable salt thereof, wherein X is —(CR$^k$R$^m$)$_u$—C(O)—X$^2$ or C(O)—X$^2$.

3. The compound of claim 1 having formula (I), or a pharmaceutically acceptable salt thereof, wherein X is —(CR$^k$R$^m$)$_u$—C(O)—X$^2$, and Q is phenyl, optionally further substituted with 1, 2, or 3 T.

4. The compound of claim 1 having formula (I), or a pharmaceutically acceptable salt thereof, wherein
X is —(CR$^k$R$^m$)$_u$—C(O)—X$^2$, Q is phenyl, optionally further substituted with 1, 2, or 3 T;
r and s are 2, and
A is formula (a).

5. A compound selected from the group consisting of
Trans {4-[4-(7-amino-2-thien-2-ylpyrazolo[1,5-a]pyrimidin-6-yl)phenyl]cyclohexyl}acetic acid;
Trans {4-[4-(7-amino-2-cyclopropylpyrazolo[1,5-a]pyrimidin-6-yl)phenyl]cyclohexyl}acetic acid;
Trans (4-{4-[7-amino-2-(4-fluorophenyl)pyrazolo[1,5-a]pyrimidin-6-yl]phenyl}cyclohexyl)acetic acid;
Trans {4-[4-(7-amino-2-methylpyrazolo[1,5-a]pyrimidin-6-yl)phenyl]cyclohexyl}acetic acid;
Trans {4-[4-(7-amino-2-hydroxypyrazolo[1,5-a]pyrimidin-6-yl)phenyl]cyclohexyl}acetic acid;
Trans 2-{4-[4-(7-aminopyrazolo[1,5-a]pyrimidin-6-yl)phenyl]cyclohexyl}-N-methylacetamide;
Trans 2-{4-[4-(7-aminopyrazolo[1,5-a]pyrimidin-6-yl)phenyl]cyclohexyl}acetamide;
Trans {4-[4-(7-aminopyrazolo[1,5-a]pyrimidin-6-yl)phenyl]cyclohexyl}acetic acid;
Trans {4-[4-(7-amino-5-methylpyrazolo[1,5-a]pyrimidin-6-yl)phenyl]cyclohexyl}acetic acid;

Trans 3-({4-[4-(7-aminopyrazolo[1,5-a]pyrimidin-6-yl)phenyl]cyclohexyl}methyl)-1,2,4-oxadiazol-5(4H)-one; and Trans 5-({4-[4-(7-aminopyrazolo[1,5-a]pyrimidin-6-yl)phenyl]cyclohexyl}methyl)-1,3,4-oxadiazol-2(3H)-one;

or a pharmaceutically acceptable salt thereof.

6. A pharmaceutical composition comprising a therapeutically effective amount of a compound of claim 1 in combination with a pharmaceutically acceptable carrier.

7. A pharmaceutical composition comprising a therapeutically effective amount of a compound of claim 1 or a pharmaceutically acceptable salt thereof, one or more pharmaceutical agents selected from the group consisting of fenofibrate, rimonabant, sibutramine, orlistat, a statin, and nicotinic acid, in combination with a pharmaceutically acceptable carrier.

8. The compound of claim 1 having formula (IIa), or a pharmaceutically acceptable salt thereof,

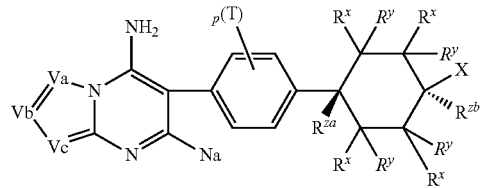

(IIa)

wherein p is 0, 1, 2, or 3; and $V_a$, $V_b$, $V_c$, $R^7$, T, $R^x$, $R^y$, $R^{za}$, $R^{zb}$ and X are as defined in claim 1.

* * * * *